United States Patent
Erker et al.

(10) Patent No.: US 6,486,277 B1
(45) Date of Patent: Nov. 26, 2002

(54) ZWITTERIONIC TRANSITION METAL COMPOUND WHICH CONTAINS BORON

(75) Inventors: Gerhard Erker, Münster (DE); Gerald Kehr, Münster (DE); Jörg Schottek, Frankfurt (DE); Roland Kratzer, Kriftel (DE)

(73) Assignee: Targor GmbH, Mainz (DE)

( * ) Notice: Subject to any disclaimer, the term of this patent is extended or adjusted under 35 U.S.C. 154(b) by 0 days.

(21) Appl. No.: 09/622,205

(22) PCT Filed: Dec. 9, 1999

(86) PCT No.: PCT/EP99/09682

§ 371 (c)(1), (2), (4) Date: Aug. 14, 2000

(87) PCT Pub. No.: WO00/35973

PCT Pub. Date: Jun. 22, 2000

(30) Foreign Application Priority Data

Dec. 12, 1998 (DE) .......................................... 198 57 377
Jan. 28, 1999 (DE) .......................................... 199 03 306

(51) Int. Cl.$^7$ .............................. C08F 4/64; C08F 4/52; C07F 17/00
(52) U.S. Cl. ........................ 526/134; 526/126; 526/160; 526/161; 526/172; 526/943; 502/117; 502/152; 556/53

(58) Field of Search ............................... 526/134, 126, 526/161, 160, 172; 502/117, 152; 556/53

(56) References Cited

U.S. PATENT DOCUMENTS

| | | | | |
|---|---|---|---|---|
| 5,541,349 A | * | 7/1996 | Wilson et al. | 556/10 |
| 5,792,819 A | * | 8/1998 | Erker et al. | 522/134 |
| 6,245,706 B1 | * | 6/2001 | Hlatky et al. | 502/152 |

OTHER PUBLICATIONS

Chang et al., "Chemistry" Third Edition, McGraw Hill, p. 10, 1988.*

Yang, J. Am. Chem. Soc., 113, 1991, p. 3623–3625.

* cited by examiner

*Primary Examiner*—David W. Wu
*Assistant Examiner*—R. Rabago
(74) *Attorney, Agent, or Firm*—Keil & Weinkauf

(57) ABSTRACT

A boron-containing zwitterionic neutral transition metal compound which can advantageously be used for the polymerization of olefins is described. Here, the use of aluminoxanes, such as methylaluminoxane (MAO), as a cocatalyst can be dispensed with and a high catalyst activity and a good polymer morphology can nevertheless be achieved.

7 Claims, No Drawings

ZWITTERIONIC TRANSITION METAL COMPOUND WHICH CONTAINS BORON

The present invention describes a zwitterionic neutral transition metal compound which can advantageously be used for the polymerization of olefins. It is thereby possible to dispense with the use of aluminoxanes, such as methylaluminoxane (MAO), as a cocatalyst and nevertheless to achieve a high catalyst activity and good polymer morphology.

The role of cationic complexes in the Ziegler-Natta polymerization with metallocenes is generally recognized (H. H. Brintzinger, D. Fischer, R. Mülhaupt, R. Rieger, R. Waymouth, Angew. Chem. 107, (1995) 1255–1283).

MAO, an effective cocatalyst, has the disadvantage that it has to be used in a large excess. The preparation of cationic alkyl complexes is opening up a route with MAO-free catalysts having comparable activity, it being possible to use the cocatalyst in an approximately stoichiometric amount.

The synthesis of cation-like metallocene polymerization catalysts is described in J. Am. Chem. Soc. 113 1991, 3623. A process for the preparation of salts of the formula $LMX^+ XA^-$ according to the principle described above is claimed in EP 520 732.

EP 558158 describes zwitterionic catalyst systems which are prepared from metallocenedialkyl compounds and salts of the form $[R_3NH]^+ [B(C_6H_5)_4]^-$. The reaction of such a salt with, for example, $Cp_2ZrMe_2$ gives a zirconocenemethyl cation as an intermediate by protolysis with methane elimination. Said cation reacts via C—H activation to give the zwitterion $Cp_2Zr^+$—(m—$C_6H_4$)—$BPh_3^-$. The Zr atom is covalently bonded to a carbon atom of the phenyl ring and stabilized via agostic hydrogen bonds.

U.S. Pat. No. 5,348,299 describes zwitterionic catalyst systems which are prepared from metallocenedialkyl compounds and salts of the form $[R_3NH]^+ [B(C_6F_5)_4]^-$ by protolysis. The C—H activation as a secondary reaction is absent.

EP 426 637 uses a process in which the Lewis acid $CPh_3^+$ cation is used for abstracting the methyl group from the metal center. $B(C_6F_5)_4^-$, too, acts as a weakly coordinating anion. Here, metallocenes with $Cp_2MR_2$ in which the alkyl radicals R are cyclically bonded to one another are also used, e.g. $Cp_2Zr(2,3$-dimethyl-1,3-butadiene). Salts of the form $[Cp_2Zr$—R—$RH]^+[B(C_6F_5)_4]^-$ form by protolysis.

EP 0687682 describes specific zwitterionic transition metal catalyst systems which are prepared from metallocenebutadiene compounds and a Lewis acid, such as tris(pentafluorophenyl)borane. These zwitterionic compounds prepared in this manner have polymerization activities comparable with metallocene compounds which are activated by MAO.

The zwitterionic compounds described in EP 0687682 have the disadvantage that they become detached from the support surface in the heterogenization required for the industrial use of metallocene catalysts, during the metering of the catalyst system into the reactor. This leads to a homogeneous polymerization in some cases. In addition, the heterogenization of these catalyst systems leads to low polymerization activity.

It is an object of the present invention to provide a transition metal compound which avoids the disadvantages of the prior art. We have found that this object is achieved by specific zwitterionic transition metal compounds. The present invention therefore relates to a zwitterionic transition metal compound of the formula I

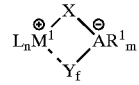

I where
L are identical or different π-ligands or electron donors which may be bonded to one another,
N is 1, 2, 3 or 4,
M is a metal atom of group IIIb, IVb, Vb or VIb of the Periodic Table of the Elements,
X is a heteroatom, an aromatic or nonaromatic heterocyclic structure or a hydrocarbon group of 1–40 carbon atoms,
Y is a $C_1$–$C_{40}$-hydrocarbon radical which may be halogenated, preferably perhalogenated, with halogens, such as fluorine, chlorine, bromine or iodine, in particular a halogenated, especially perhalogenated, $C_1$–$C_{30}$-alkyl group, such as trifluoromethyl, pentachloroethyl, heptafluoroisopropyl or monofluoroisobutyl, or a halogenated $C_6$–$C_{30}$-aryl group, such as pentafluorophenyl, 2,4,6-trifluorophenyl, heptachloronaphthyl, heptafluoronaphthyl, heptafluorotolyl, 3,5-bis(trifluoromethyl)phenyl, 2,4,6-tris(trifluoromethyl)phenyl, nonafluorobiphenyl or 4-trifluoromethyl)phenyl; Y is also preferably a radical such as phenyl, naphthyl, anisyl, methyl, ethyl, isopropyl, butyl, tolyl, biphenyl, 2,3-dimethylphenyl or an allyl radical of at least 3 carbon atoms;
f is 0 or 1,
A is a metal atom of group Ib, IIb, IIIa, IVa, Va, VIb, VIIb or VIIIb of the Periodic Table of the Elements,
$R^1$ is a $C_1$–$C_{40}$-hydrocarbon radical which may be halogenated, preferably perhalogenated, with halogens, such as fluorine, chlorine, bromine or iodine, in particular a halogenated, especially perhalogenated, $C_1$–$C_{30}$-alkyl group, such as trifluoromethyl, pentachloroethyl, heptafluoroisopropyl or monofluoroisobutyl, or a halogenated $C_6$–$C_{30}$-aryl group, such as pentafluorophenyl, 2,4,6-trifluorophenyl, heptachloronaphthyl, heptafluoronaphthyl, heptafluorotolyl, 3,5-bis(trifluoromethyl)phenyl, 2,4,6-tris(trifluoromethyl)phenyl, nonafluorobiphenyl or 4-(trifluoromethyl)phenyl; $R^1$ is also preferably a radical such as phenyl, naphthyl, anisyl, methyl, ethyl, isopropyl, butyl, tolyl, biphenyl or 2,3-dimethylphenyl;
m is 1, 2, 3, 4 or 5.

The metal atoms $M^1$ and A are linked to one another by a covalent or coordinate bond via the structural element X.

Where Y is an allyl unit, the bond from Y to the metal atom M may be a σ-allyl or a-allyl bond, an additional bridging is effected via the structural element X which links the metal atoms $M^1$ and A to one another by a covalent or coordinate bond. This structural element X is preferably a heteroatom, a heterocyclic structure or a hydrocarbon group of 1–40 carbon atoms. If X is a heterocyclic structure containing double bonds, the bond from X to the metal atom M may be a coordinate bond.

Preferred π-ligands are unsubstituted or substituted cyclopentadienyl groups which are identical or different and constitute a substituted or unsubstituted cyclopentadienyl, indenyl or fluorenyl group, where two radicals L may be linked to one another via a bridge Z.

A heteroatom is understood as meaning any atom of the Periodic Table of the Elements, with the exception of carbon and hydrogen. O, S and N are preferred.

Heterocyclic structures may be, inter alia, substituted or unsubstituted pyrrolidines, pyrroles, indoles, imidazoles, isoindoles or benzimidazoles.

Hydrocarbon groups X may be saturated or unsaturated, linear or branched, e.g. $C_4$–$C_{12}$-heteroaryl, $C_1$–$C_{20}$-heteroalkyl, $C_1$–$C_{20}$-alkyl, $C_6$–$C_{14}$-aryl, $C_2$–$C_{10}$-alkenyl, $C_7$–$C_{40}$-arylalkyl, $C_7$–$C_{40}$-alkylaryl or $C_8$–$C_{40}$-arylalkyl. Unsubstituted and substituted heteroaryl and heteroalkyl groups which may also have aromatic structural elements are preferred.

n may preferably be from 1 to 4.

Particularly preferred compounds of the formula I are those in which

M is a metal atom of group IVb of the Periodic Table of the Elements, such as titanium, zirconium or hafnium, n is 2 or 3, L is a preferably substituted cyclopentadienyl ring, in particular substituted in the 1, 3-, 1, 2-, or 1, 2, 4-position by $C_1$–$C_{20}$-carbon-containing groups, such as $C_1$–$C_{10}$-alkyl or $C_6$–$C_{20}$-aryl, or a preferably substituted indenyl ring, in particular substituted in the 2, 4-, 2, 4, 5-, 2, 4, 6-, 2, 4, 7- or 2, 4, 5, 6-position by $C_1$–$C_{20}$-carbon-containing groups, such as $C_1$–$C_{10}$-alkyl or $C_6$–$C_{20}$-aryl, it also being possible for two or more substituents of the indenyl ring together to form a ring system; these cyclopentadienyl and indenyl ring may be unbridged or bridged by Z; bridging by two radicals L in the 1-position is particularly preferred;

Z are bridging groups of the formula $M^2R^2R^3$, where $M^2$ is carbon, silicon, germanium or tin and $R^2$ and $R^3$ are identical or different $C_1$–$C_{20}$-hydrocarbon-containing groups, such as $C_1$–$C_{10}$-alkyl, $C_6$–$C_{14}$-aryl or trimethylsilyl; $M^2$ is preferably $CH_2$, $CH_2CH_2$, $CH(CH_3)CH_2$, $CH(C_4H_9)C(CH_3)_2$, $C(CH)_2$, $(CH_3)_2Si$, $(CH_3)_2Ge$, $(CH_3)_2Sn$, $(C_6H_5)_2Si$, $(C_6H_5)(CH_3)Si$, $Si(CH_3)(SiR^4R^5R^6)$, $(C_6H_5)_2Ge$, $(C_6H_5)_2Sn$, $(CH_2)_4Si$, $CH_2Si(CH_3)_2$, o—$C_6H_4$ 2,2'-$(C_6H_4)_2$; $R^4R^5R^6$ are identical or different $C_1$–$C_{20}$-hydrocarbon-containing groups, such as $C_1$–$C_{10}$-alkyl or $C_6$–$C_{14}$-aryl; Z may furthermore link two or more identical or different groups $L_nM^+$—X—A—$R^1_m$ to one another, where Z may be $CR^2R^3$ or $SiR^2R^3$ or is $Si(CR^2R^3)i$—Si, which link two fragments $L_nM^+$—X—A—$(R^1_m)$—Y to one another, i being from 0 to 10, preferably 6;

X may be an aromatic or nonaromatic heterocyclic structure or a heteroalkyl group;

Y is not present when f=0,

A is a metal of group Ib, IIb, IIIa, IVa, Va, or Vb, $R^1$ are identical or different and are each a perfluorinated alkyl or aryl group and m is 2, 3 or 4.

Very particularly preferred compounds of the formula I are those in which

M is zirconium, n is 3,

L are identical or different and are each a substituted cyclopentadienyl group, such as 2-methylcyclopentadienyl, 1,3-methylcyclopentadienyl, 2-n-propylcyclopentadienyl or pentamethylcyclopentadienyl, or an alkyl group, such as methyl, where two radicals L are linked to one another via a bridge Z, Z being a substituted carbon or silicon atom, X is an unsaturated heterocyclic structure with N as a heteroatom, which is bonded to M by a coordinate bond, Y is not present when f=0, A is a boron atom, $R^1$ are identical and are each a pentafluorophenyl group and m is 3.

When f=1, the preferred compound is one of the formula II

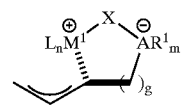

where

M is a metal atom of group IVb of the Periodic Table of the Elements, such as titanium, zirconium or hafnium, n is 2, L is a preferably substituted cyclopentadienyl ring, in particular substituted in the 1, 3-, 1, 2-, or 1, 2, 4-position by $C_1$–$C_{20}$-carbon-containing groups, such as $C_1$–$C_{10}$-alkyl or $C_6$–$C_{20}$-aryl, or a preferably substituted indenyl ring, in particular substituted in the 2-, 4-, 2, 4, 5-, 2, 4, 6-, 2, 4, 7- or 2, 4, 5, 6-position by $C_1$–$C_{20}$-carbon-containing groups, such as $C_1$–$C_{10}$-alkyl or $C_6$–$C_{20}$-aryl, it also being possible for two or more substituents of the indenyl ring together to form a ring system; these cyclopentadienyl and indenyl rings may be unbridged or bridged by Z; bridging by two radicals L in the 1-position is particularly preferred;

Z are bridging groups of the formula $M^2R^2R^3$, where $M^2$ is carbon, silicon, germanium or tin and $R^2$ and $R^3$ are identical or different $C_1$–$C_{20}$-carbon-containing groups, such as $C_1$–$C_{10}$-alkyl, $C_6$–$C_{14}$-aryl or trimethylsilyl; $M^2$ is preferably $CH_2$, $CH_2CH_2$, $CH(CH_3)CH_2$, $CH(C_4H_9)C(CH_3)_2$, $C(CH)_2$, $(CH_3)_2Si$, $(CH_3)_2Ge$, $(CH_3)_2Sn$, $(C_6H_5)_2Si$, $(C_6H_5)(CH_3)Si$, $Si(CH_3)(SiR^4R^5R^6)$, $(C_6H_5)_2Ge$, $(C_6H_5)_2Sn$, $(CH_2)_4Si$, $CH_2Si(CH_3)_2$, o—$C_6H_4$ or 2,2'-$(C_6H_4)_2$; $R^4R^5R^6$ are identical or different $C_1$–$C_{20}$-hydrocarbon-containing groups, such as $C_1$–$C_{10}$-alkyl or $C_6$–$C_{14}$-aryl; Z may furthermore link two or more identical or different groups $L_nM^+$—X—A—$R^1_m$ to one another, where Z may be $CR^2R^3$ or $SiR^2R^3$ or is $Si(CR^2R^3)i$—Si, which link two fragments $L_nM^+$—X—A—$(R^1_m)$—Y to one another, i being from 0 to 10, preferably 6;

X may be an aromatic or nonaromatic heterocyclic structure or a heteroalkyl group; X may furthermore form a three- to five-membered alkyl chain which is saturated or unsaturated, Y is of the formula

g is an integer from 0 to 37, it also being possible for individual hydrogen atoms to be substituted by alkyl groups, A is a metal of group Ib, IIb, IIIa, IVa, Va or Vb, $R^1$ are identical or different and are each a perfluorinated alkyl or aryl group and m is 2, 3 or 4.

Very particularly preferred compounds of the formula II are those in which

M is zirconium, n is 3,

L are identical or different and are each a substituted cyclopentadienyl group, such as 2-methylcyclopentadienyl, 1,3-methylcyclopentadienyl, 2-n-propylcyclopentadienyl or pentamethylcyclopentadienyl, or an alkyl group, such as methyl, where two radicals L are linked to one another via a bridge Z, Z being a substituted carbon or silicon atom, X is an unsaturated heterocyclic structure with N as a heteroatom, which is bonded to M by a coordinate bond, g is a saturated or unsaturated alkyl chain with g=1, whose hydrogen atoms may also be substituted by alkyl groups, A is a boron atom, $R^1$ are identical and are each a pentafluorophenyl group and m is 3.

Examples of novel compounds of the formula I are:
bis(cyclopentadienyl)methylzirconiummethylbis(pentafluorophenyl)pyrrolylborate bis(methylcyclopentadienyl)methylzirconiummethylbis(pentafluorophenyl)pyrrolylborate bis(pentamethylcyclopentadienyl)methylzirconiummethylbis(pentafluorophenyl)pyrrolylborate bis(n-butylcyclopentadienyl)methylzirconiummethylbis(pentafluorophenyl)pyrrolylborate bis(indenyl)methylzirconiummethylbis(pentafluorophenyl)pyrrolylborate bis(2-methylindenyl)methylzirconiummethylbis(pentafluorophenyl)pyrrolylborate bis(2-methylbenzindenyl)methylzirconiummethylbis(pentafluorophenyl)pyrrolylborate (tert-butylamido)dimethyl(tetramethyl-$\eta^5$-cyclopentadienyl)silanemethylzirconiummethylbis(pentafluorophenyl)pyrrolylborate dimethylsilanediylbis(indenyl)methylzirconiummethylbis(pentafluorophenyl)pyrrolylborate dimethylsilanediylbis(2-methylindenyl)methylzirconiummethylbis(pentafluorophenyl)pyrrolylborate dimethylsilanediylbis(2-methylbenzindenyl)methylzirconiummethylbis(pentafluorophenyl)pyrrolylborate dimethylsilanediylbis(4-phenylindenyl)methylzirconiummethylbis(pentafluorophenyl)pyrrolylborate dimethylsilanediylbis(4-naphthylindenyl)methylzirconiummethylbis(pentafluorophenyl)pyrrolylborate dimethylsilanediylbis(2-methyl-4-(1-naphthyl)indenyl)methylzirconiummethylbis(pentafluorophenyl)pyrrolylborate dimethylsilanediylbis(2-methyl-4-(2-naphthyl)indenyl)methylzirconiummethylbis(pentafluorophenyl)pyrrolylborate dimethylsilanediylbis(2-methyl-4-phenylindenyl)methylzirconiummethylbis(pentafluorophenyl)pyrrolylborate dimethylsilanediylbis(2-methyl-4-tert-butylindenyl)methylzirconiummethylbis(pentafluorophenyl)pyrrolylborate dimethylsilanediylbis(2-methyl-4-isopropylindenyl)methylzirconiummethylbis(pentafluorophenyl)pyrrolylborate dimethylsilanediylbis(2-methyl-4-(1-naphtyl)indenyl)methylzirconiummethylbis(pentafluorophenyl)pyrrolylborate dimethylsilanediylbis(2-methyl-4-ethylindenyl)methylzirconiummethylbis(pentafluorophenyl)pyrrolylborate dimethylsilanediylbis(2-methyl-4-(acenaphthyl)indenyl)methylzirconiummethylbis(pentafluorophenyl)pyrrolylborate dimethylsilanediylbis(2,4-dimethylindenyl)methylzirconiummethylbis-(pentafluorophenyl)pyrrolylborate dimethylsilanediylbis(2-ethylindenyl)methylzirconiummethylbis(pentafluorophenyl)pyrrolylborate dimethylsilanediylbis(2-ethyl-4-ethylindenyl)methylzirconiummethylbis(pentafluorophenyl)pyrrolylborate dimethylsilanediylbis(2-ethyl-4-phenylindenyl)methylzirconiummethylbis(pentafluorophenyl)pyrrolylborate dimethylsilanediylbis(2-methyl-4-(4'-tert-butylphenyl)indenyl)methylzirconiummethylbis(pentafluorophenyl)pyrrolylborate dimethylsilanediylbis(2-methyl-4-(4'-methylphenyl)indenyl)methylzirconiummethylbis(pentafluorophenyl)pyrrolylborate dimethylsilanediylbis(2-methyl-4-(4'-ethylphenyl)indenyl)methylzirconiummethylbis(pentafluorophenyl)pyrrolylborate dimethylsilanediylbis(2-methyl-4-(4'-n-propylphenyl)indenyl)methylzirconiummethylbis(pentafluorophenyl)pyrrolylborate dimethylsilanediylbis(2-methyl-4-(4'-iso-propylphenyl)indenyl)methylzirconiummethylbis(pentafluorophenyl)pyrrolylborate dimethylsilanediylbis(2-methyl-4-(4'-n-butylphenyl)indenyl)methylzirconiummethylbis(pentafluorophenyl)pyrrolylborate dimethylsilanediylbis(2-methyl-4-(4'-hexylphenyl)indenyl)methylzirconiummethylbis(pentafluorophenyl)pyrrolylborate dimethylsilanediylbis(2-methyl-4-(4'-sec-butylphenyl)indenyl)methylzirconiummethylbis(pentafluorophenyl)pyrrolylborate dimethylsilanediylbis(2-ethyl-4-(4'-tert-butylphenyl)indenyl)methylzirconiummethylbis(pentafluorophenyl)pyrrolylborate dimethylsilanediylbis(2-ethyl-4-(4'-methylphenyl)indenyl)methylzirconiummethylbis(pentafluorophenyl)pyrrolylborate dimethylsilanediylbis(2-ethyl-4-(4'-ethylphenyl)indenyl)methylzirconiummethylbis(pentafluorophenyl)pyrrolylborate dimethylsilanediylbis(2-ethyl-4-(4'-n-propylphenyl)indenyl)methylzirconiummethylbis(pentafluorophenyl)pyrrolylborate dimethylsilanediylbis(2-ethyl-4-(4'-isopropylphenyl)indenyl)methylzirconiummethylbis(pentafluorophenyl)pyrrolylborate dimethylsilanediylbis(2-ethyl-4-(4'-n-butylphenyl)indenyl)methylzirconiummethylbis(pentafluorophenyl)pyrrolylborate dimethylsilanediylbis(2-ethyl-4-(4'-hexylphenyl)indenyl)methylzirconiummethylbis(pentafluorophenyl)pyrrolylborate dimethylsilanediylbis(2-ethyl-4-(4'-sec-butylphenyl)indenyl)methylzirconiummethylbis(pentafluorophenyl)pyrrolylborate dimethylsilanediylbis(2-n-propyl-4-(4'-tert-butylphenyl)indenyl)methylzirconiummethylbis(pentafluorophenyl)pyrrolylborate dimethylsilanediylbis(2-n-propyl-4-(4'-methylphenyl)indenyl)methylzirconiummethylbis(pentafluorophenyl)pyrrolylborate
dimethylsilanediylbis(2-n-propyl-4-(4'-ethylphenyl)indenyl)methylzirconiummethylbis(pentafluorophenyl)pyrrolylborate
dimethylsilanediylbis(2-n-propyl-4-(4'-n-propylphenyl)indenyl)methylzirconiummethylbis(pentafluorophenyl)pyrrolylborate
dimethylsilanediylbis(2-n-propyl-4-(4'-isopropylphenyl)indenyl)methylzirconiummethylbis(pentafluorophenyl)pyrrolylborate
dimethylsilanediylbis(2-n-propyl-4-(4'-n-butylphenyl)indenyl)methylzirconiummethylbis(pentafluorophenyl)pyrrolylborate
dimethylsilanediylbis(2-n-propyl-4-(4'-hexylphenyl)indenyl)methylzirconiummethylbis(pentafluorophenyl)pyrrolylborate
dimethylsilanediylbis(2-n-propyl-4-(4'-sec-butylphenyl)indenyl)methylzirconiummethylbis(pentafluorophenyl)pyrrolylborate
dimethylsilanediylbis(2-n-butyl-4-(4'-tert-butylphenyl)indenyl)methylzirconiummethylbis(pentafluorophenyl)pyrrolylborate
dimethylsilanediylbis(2-n-butyl-4-(4'-methylphenyl)indenyl)methylzirconiummethylbis(pentafluorophenyl)pyrrolylborate
dimethylsilanediylbis(2-n-butyl-4-(4'-ethylphenyl)indenyl)methylzirconiummethylbis(pentafluorophenyl)pyrrolylborate
dimethylsilanediylbis(2-n-butyl-4-(4'-n-propylphenyl)indenyl)methylzirconiummethylbis(pentafluorophenyl)pyrrolylborate
dimethylsilanediylbis(2-n-butyl-4-(4'-isopropylphenyl)indenyl)methylzirconiummethylbis(pentafluorophenyl)pyrrolylborate
dimethylsilanediylbis(2-n-butyl-4-(4'-n-butylphenyl)indenyl)methylzirconiummethylbis(pentafluorophenyl)pyrrolylborate
dimethylsilanediylbis(2-n-butyl-4-(4'-hexylphenyl)indenyl)methylzirconiummethylbis(pentafluorophenyl)pyrrolylborate
dimethylsilanediylbis(2-n-butyl-4-(4'-sec-butylphenyl)indenyl)methylzirconiummethylbis(pentafluorophenyl)pyrrolylborate
dimethylsilanediylbis(2-n-hexyl-4-(4'-tert-butylphenyl)indenyl)methylzirconiummethylbis(pentafluorophenyl)pyrrolylborate
dimethylsilanediylbis(2-n-hexyl-4-(4'-methylphenyl)indenyl)methylzirconiummethylbis(pentafluorophenyl)pyrrolylborate
dimethylsilanediylbis(2-n-hexyl-4-(4'-ethylphenyl)indenyl)methylzirconiummethylbis(pentafluorophenyl)pyrrolylborate
dimethylsilanediylbis(2-n-hexyl-4-(4'-n-propylphenyl)indenyl)methylzirconiummethylbis(pentafluorophenyl)pyrrolylborate
dimethylsilanediylbis(2-n-hexyl-4-(4'-isopropylphenyl)indenyl)methylzirconiummethylbis(pentafluorophenyl)pyrrolylborate
dimethylsilanediylbis(2-n-hexyl-4-(4'-n-butylphenyl)indenyl)methylzirconiummethylbis(pentafluorophenyl)pyrrolylborate
dimethylsilanediylbis(2-n-hexyl-4-(4'-hexylphenyl)indenyl)methylzirconiummethylbis(pentafluorophenyl)pyrrolylborate
dimethylsilanediylbis(2-n-hexyl-4-(4'-sec-butylphenyl)indenyl)methylzirconiummethylbis(pentafluorophenyl)pyrrolylborate
dimethylsilanediylbis(2-methyl-4,5-benzoindenyl)methylzirconiummethylbis(pentafluorophenyl)pyrrolylborate
dimethylsilanediylbis(2-methyl-4,6-diisopropylindenyl)methylzirconiummethylbis(pentafluorophenyl)pyrrolylborate
dimethylsilanediylbis(2,4,6-trimethylindenyl)methylzirconiummethylbis(pentafluorophenyl)pyrrolylborate
dimethylsilanediylbis(2,5,6-trimethylindenyl)methylzirconiummethylbis(pentafluorophenyl)pyrrolylborate
dimethylsilanediylbis(2,4,7-trimethylindenyl)methylzirconiummethylbis(pentafluorophenyl)pyrrolylborate
dimethylsilanediylbis(2-methyl-5-isobutylindenyl)methylzirconiummethylbis(pentafluorophenyl)pyrrolylborate
dimethylsilanediylbis(2-methyl-5-tert-butylindenyl)methylzirconiummethylbis(pentafluorophenyl)pyrrolylborate
methyl(phenyl)silanediylbis(indenyl)methylzirconiummethylbis(pentafluorophenyl)pyrrolylborate
methyl(phenyl)silanediylbis(2-methylindenyl)methylzirconiummethylbis(pentafluorophenyl)pyrrolylborate
methyl(phenyl)silanediylbis(2-methylbenzindenyl)methylzirconiummethylbis(pentafluorophenyl)pyrrolylborate
methyl(phenyl)silanediylbis(4-phenylindenyl)methylzirconiummethylbis(pentafluorophenyl)pyrrolylborate
methyl(phenyl)silanediylbis(4-naphthylindenyl)methylzirconiummethylbis(pentafluorophenyl)pyrrolylborate
methyl(phenyl)silanediylbis(2-methyl-4-(1-naphthyl)indenyl)methylzirconiummethylbis(pentafluorophenyl)pyrrolylborate
methyl(phenyl)silanediylbis(2-methyl-4-(2-naphthyl)indenyl)methylzirconiummethylbis(pentafluorophenyl)pyrrolylborate
methyl(phenyl)silanediylbis(2-methyl-4-phenylindenyl)methylzirconiummethylbis(pentafluorophenyl)pyrrolylborate
methyl(phenyl)silanediylbis(2-methyl-4-tert-butylindenyl)methylzirconiummethylbis(pentafluorophenyl)pyrrolylborate
methyl(phenyl)silanediylbis(2-methyl-4-isopropylindenyl)methylzirconiummethylbis(pentafluorophenyl)pyrrolylborate
methyl(phenyl)silanediylbis(2-methyl-4-(1-naphthyl)indenyl)methylzirconiummethylbis(pentafluorophenyl)pyrrolylborate
methyl(phenyl)silanediylbis(2-methyl-4-ethylindenyl)methylzirconiummethylbis(pentafluorophenyl)pyrrolylborate
methyl(phenyl)silanediylbis(2-methyl-4-(acenaphthyl)indenyl)methylzirconiummethylbis(pentafluorophenyl)pyrrolylborate
methyl(phenyl)silanediylbis(2,4-dimethylindenyl)methylzirconiummethylbis(pentafluorophenyl)pyrrolylborate
methyl(phenyl)silanediylbis(2-ethylindenyl)methylzirconiummethylbis(pentafluorophenyl)pyrrolylborate
methyl(phenyl)silanediylbis(2-ethyl-4-ethylindenyl)methylzirconiummethylbis(pentafluorophenyl)pyrrolylborate
methyl(phenyl)silanediylbis(2-ethyl-4-phenylindenyl)methylzirconiummethylbis(pentafluorophenyl)pyrrolylborate
methyl(phenyl)silanediylbis(2-methyl-4,5-benzoindenyl)methylzirconiummethylbis(pentafluorophenyl)pyrrolylborate
methyl(phenyl)silanediylbis(2-methyl-4,6-diisopropylindenyl)methylzirconiummethylbis(pentafluorophenyl)pyrrolylborate
methyl(phenyl)silanediylbis(2,4,6- trimethylindenyl)methylzirconiummethylbis(pentafluorophenyl)pyrrolylborate methyl(phenyl)silanediylbis(2,5,6-trimethylindenyl)methylzirconiummethylbis(pentafluorophenyl)pyrrolylborate methyl(phenyl)silanediylbis(2,4,7-trimethylindenyl)methylzirconiummethylbis(pentafluorophenyl)pyrrolylborate methyl(phenyl)silanediylbis(2-methyl-5-isobutylindenyl)methylzirconiummethylbis(pentafluorophenyl)pyrrolylborate methyl(phenyl)silanediylbis(2-methyl-5-tert-butylindenyl)methylzirconiummethylbis(pentafluorophenyl)pyrrolylborate diphenylmethylene(fluorenyl)(cyclopentadienyl)methylzirconiummethylbis(pentafluorophenyl)pyrrolylborate dimethylmethylene(fluorenyl)(cyclopentadienyl)methylzirconiummethylbis(pentafluorophenyl)pyrrolylborate methylphenylmethylene(fluorenyl)(cyclopentadienyl)methylzirconiummethylbis(pentafluorophenyl)pyrrolylborate dimethylsilanediyl(3-tert-butylcyclopentadienyl)(fluorenyl)methylzirconiummethylbis(pentafluorophenyl)pyrrolylborate diphenylsilanediyl(3-(trimethyl)cyclopentadienyl)(fluorenyl)methylzirconiummethylbis(pentafluorophenyl)pyrrolylborate ethylenebis(indenyl)methylzirconiummethylbis(pentafluorophenyl)pyrrolylborate ethylenebis(2-methylindenyl)methylzirconiummethylbis(pentafluorophenyl)pyrrolylborate ethylenebis(2-methyl-4-phenylindenyl)methylzirconiummethylbis(pentafluorophenyl)pyrrolylborate ethylenebis(2-methyl-4,5-benzindenyl)methylzirconiummethylbis(pentafluorophenyl)pyrrolylborate ethylenebis(2-methyl-4,6-diisopropylindenyl)methylzirconiummethylbis(pentafluorophenyl)pyrrolylborate 1,6-{bis[methylsilylbis(2-methyl-4-phenylindenyl)methylzirconiummethylbis(pentafluorophenyl)pyrrolylborate}hexane 1,6-{bis[methylsilylbis(2-ethyl-4-phenylindenyl)methylzirconiummethylbis(pentafluorophenyl)pyrrolylborate}hexane 1,6-{bis[methylsilylbis(2-methyl-4-naphthylphenylindenyl)methylzirconiummethylbis(pentafluorophenyl)pyrrolylborate}hexane 1,6-{bis[methylsilylbis(2-methyl-4,5-benzoindenyl)methylzirconiummethylbis(pentafluorophenyl)pyrrolylborate}hexane 1,6-{bis[methylsilyl(2-methyl-4-phenylindenyl)(2-methylindenylmethylzirconiummethylbis(pentafluorophenyl)pyrrolylborate}hexane 1,6-{bis[methylsilylbis(2-methyl-4-phenylindenyl)methylzirconiummethylbis(pentafluorophenyl)pyrrolylborate}ethane 1,6-{bis[methylsilylbis(2-ethyl-4-phenylindenyl)methylzirconiummethylbis(pentafluorophenyl)pyrrolylborate}ethane 1,6-{bis[methylsilylbis(2-methyl-4-naphthylphenylindenyl)methylzirconiummethylbis(pentafluorophenyl)pyrrolylborate}ethane 1,6-{bis[methylsilylbis(2-methyl-4,5-benzoindenyl)methylzirconiummethylbis(pentafluorophenyl)pyrrolylborate}ethane 1,6-{bis[methylsilyl(2-methyl-4-phenylindenyl)(2-methylindenylmethylzirconiummethylbis(pentafluorophenyl)pyrrolylborate}ethane tri(cyclopentadienyl)zirconiummethylbis(pentafluorophenyl)pyrrolylborate tri(methylcyclopentadienyl)zirconiummethylbis(pentafluorophenyl)pyrrolylborate tri(pentamethylcyclopentadienyl)zirconiummethylbis(pentafluorophenyl)pyrrolylborate tri(n-butylcyclopentadienyl)zirconiummethylbis(pentafluorophenyl)pyrrolylborate bis(cyclopentadienyl)methylzirconiummethylbis(pentafluorophenyl)imidazolylborate bis(methylcyclopentadienyl)methylzirconiummethylbis(pentafluorophenyl)imidazolylborate bis(pentamethylcyclopentadienyl)methylzirconiummethylbis(pentafluorophenyl)imidazolylborate bis(n-butylcyclopentadienyl)methylzirconiummethylbis(pentafluorophenyl)imidazolylborate bis(indenyl)methylzirconiummethylbis(pentafluorophenyl)imidazolylborate bis(2-methylindenyl)methylzirconiummethylbis(pentafluorophenyl)imidazolylborate bis(2-methylbenzindenyl)methylzirconiummethylbis(pentafluorophenyl)imidazolylborate (tert-butylamido)dimethyl(tetramethyl-$\eta^5$-cyclopentadienyl)silanemethylzirconiummethylbis(pentafluorophenyl)imidazolylborate dimethylsilanediylbis(indenyl)methylzirconiummethylbis(pentafluorophenyl)imidazolylborate dimethylsilanediylbis(2-methylindenyl)methylzirconiummethylbis(pentafluorophenyl)imidazolylborate dimethylsilanediylbis(2-methylbenzindenyl)methylzirconiummethylbis(pentafluorophenyl)imidazolylborate dimethylsilanediylbis(4-phenylindenyl)methylzirconiummethylbis(pentafluorophenyl)imidazolylborate dimethylsilanediylbis(4-naphthylindenyl)methylzirconiummethylbis(pentafluorophenyl)imidazolylborate dimethylsilanediylbis(2-methyl-4-(1-naphthyl)indenyl)methylzirconiummethylbis(pentafluorophenyl)imidazolylborate dimethylsilanediylbis(2-methyl-4-(2-naphthyl)indenyl)methylzirconiummethylbis(pentafluorophenyl)imidazolylborate dimethylsilanediylbis(2-methyl-4-phenylindenyl)methylzirconiummethylbis(pentafluorophenyl)imidazolylborate dimethylsilanediylbis(2-methyl-4-tert-butylindenyl)methylzirconiummethylbis(pentafluorophenyl)imidazolylborate dimethylsilanediylbis(2-methyl-4-isopropylindenyl)methylzirconiummethylbis(pentafluorophenyl)imidazolylborate dimethylsilanediylbis(2-methyl-4-(1-naphthyl)indenyl)methylzirconiummethylbis(pentafluorophenyl)imidazolylborate dimethylsilanediylbis(2-methyl-4-ethylindenyl)methylzirconiummethylbis(pentafluorophenyl)imidazolylborate dimethylsilanediylbis(2-methyl-4-(acenaphthyl)indenyl)methylzirconiummethylbis(pentafluorophenyl)imidazolylborate dimethylsilanediylbis(2,4-dimethylindenyl)methylzirconiummethylbis(pentafluorophenyl)imidazolylborate dimethylsilanediylbis(2-ethylindenyl)methylzirconiummethylbis(pentafluorophenyl)imidazolylborate dimethylsilanediylbis(2-ethyl-4-ethylindenyl)methylzirconiummethylbis(pentafluorophenyl)imidazolylborate dimethylsilanediylbis(2-ethyl-4-phenylindenyl)methylzirconiummethylbis(pentafluorophenyl)imidazolylborate dimethylsilanediylbis(2-methyl-4-(4'-tert-butylphenyl)indenyl)methylzirconiummethylbis(pentafluorophenyl)imidazolylborate dimethylsilanediylbis(2-methyl-4-(4'-methylphenyl)

indenyl)methylzirconiummethylbis(pentafluorophenyl)imidazolylborate
dimethylsilanediylbis(2-methyl-4-(4'-ethylphenyl)indenyl)methylzirconiummethylbis(pentafluorophenyl)imidazolylborate
dimethylsilanediylbis(2-methyl-4-(4'-n-propylphenyl)indenyl)methylzirconiummethylbis(pentafluorophenyl)imidazolylborate
dimethylsilanediylbis(2-methyl-4-(4'-isopropylphenyl)indenyl)methylzirconiummethylbis(pentafluorophenyl)imidazolylborate
dimethylsilanediylbis(2-methyl-4-(4'-n-butylphenyl)indenyl)methylzirconiummethylbis(pentafluorophenyl)imidazolylborate
dimethylsilanediylbis(2-methyl-4-(4'-hexylphenyl)indenyl)methylzirconiummethylbis(pentafluorophenyl)imidazolylborate
dimethylsilanediylbis(2-methyl-4-(4'-sec-butylphenyl)indenyl)methylzirconiummethylbis(pentafluorophenyl)imidazolylborate
dimethylsilanediylbis(2-ethyl-4-(4'-tert-butylphenyl)indenyl)methylzirconiummethylbis(pentafluorophenyl)imidazolylborate
dimethylsilanediylbis(2-ethyl-4-(4'-methylphenyl)indenyl)methylzirconiummethylbis(pentafluorophenyl)imidazolylborate
dimethylsilanediylbis(2-ethyl-4-(4'-ethylphenyl)indenyl)methylzirconiummethylbis(pentafluorophenyl)imidazolylborate
dimethylsilanediylbis(2-ethyl-4-(4'-n-propylphenyl)indenyl)methylzirconiummethylbis(pentafluorophenyl)imidazolylborate
dimethylsilanediylbis(2-ethyl-4-(4'-isopropylphenyl)indenyl)methylzirconiummethylbis(pentafluorophenyl)imidazolylborate
dimethylsilanediylbis(2-ethyl-4-(4'-n-butylphenyl)indenyl)methylzirconiummethylbis(pentafluorophenyl)imidazolylborate
dimethylsilanediylbis(2-ethyl-4-(4'-hexylphenyl)indenyl)methylzirconiummethylbis(pentafluorophenyl)imidazolylborate
dimethylsilanediylbis(2-ethyl-4-(4'-sec-butylphenyl)indenyl)methylzirconiummethylbis(pentafluorophenyl)imidazolylborate
dimethylsilanediylbis(2-n-propyl-4-(4'-tert-butylphenyl)indenyl)methylzirconiummethylbis(pentafluorophenyl)imidazolylborate
dimethylsilanediylbis(2-n-propyl-4-(4'-methylphenyl)indenyl)methylzirconiummethylbis(pentafluorophenyl)imidazolylborate
dimethylsilanediylbis(2-n-propyl-4-(4'-ethylphenyl)indenyl)methylzirconiummethylbis(pentafluorophenyl)imidazolylborate
dimethylsilanediylbis(2-n-propyl-4-(4'-n-propylphenyl)indenyl)methylzirconiummethylbis(pentafluorophenyl)imidazolylborate
dimethylsilanediylbis(2-n-propyl-4-(4'-isopropylphenyl)indenyl)methylzirconiummethylbis(pentafluorophenyl)imidazolylborate
dimethylsilanediylbis(2-n-propyl-4-(4'-n-butylphenyl)indenyl)methylzirconiummethylbis(pentafluorophenyl)imidazolylborate
dimethylsilanediylbis(2-n-propyl-4-(4'-hexylphenyl)indenyl)methylzirconiummethylbis(pentafluorophenyl)imidazolylborate
dimethylsilanediylbis(2-n-propyl-4-(4'-sec-butylphenyl)indenyl)methylzirconiummethylbis(pentafluorophenyl)imidazolylborate
dimethylsilanediylbis(2-n-butyl-4-(4'-tert-butylphenyl)indenyl)methylzirconiummethylbis(pentafluorophenyl)imidazolylborate
dimethylsilanediylbis(2-n-butyl-4-(4'-methylphenyl)indenyl)methylzirconiummethylbis(pentafluorophenyl)imidazolylborate
dimethylsilanediylbis(2-n-butyl-4-(4'-ethylphenyl)indenyl)methylzirconiummethylbis(pentafluorophenyl)imidazolylborate
dimethylsilanediylbis(2-n-butyl-4-(4'-n-propylphenyl)indenyl)methylzirconiummethylbis(pentafluorophenyl)imidazolylborate
dimethylsilanediylbis(2-n-butyl-4-(4'-isopropylphenyl)indenyl)methylzirconiummethylbis(pentafluorophenyl)imidazolylborate
dimethylsilanediylbis(2-n-butyl-4-(4'-n-butylphenyl)indenyl)methylzirconiummethylbis(pentafluorophenyl)imidazolylborate
dimethylsilanediylbis(2-n-butyl-4-(4'-hexylphenyl)indenyl)methylzirconiummethylbis(pentafluorophenyl)imidazolylborate
dimethylsilanediylbis(2-n-butyl-4-(4'-sec-butylphenyl)indenyl)methylzirconiummethylbis(pentafluorophenyl)imidazolylborate
dimethylsilanediylbis(2-n-hexyl-4-(4'-tert-butylphenyl)indenyl)methylzirconiummethylbis(pentafluorophenyl)imidazolylborate
dimethylsilanediylbis(2-n-hexyl-4-(4'-methylphenyl)indenyl)methylzirconiummethylbis(pentafluorophenyl)imidazolylborate
dimethylsilanediylbis(2-n-hexyl-4-(4'-ethylphenyl)indenyl)methylzirconiummethylbis(pentafluorophenyl)imidazolylborate
dimethylsilanediylbis(2-n-hexyl-4-(4'-n-propylphenyl)indenyl)methylzirconiummethylbis(pentafluorophenyl)imidazolylborate
dimethylsilanediylbis(2-n-hexyl-4-(4'-isopropylphenyl)indenyl)methylzirconiummethylbis(pentafluorophenyl)imidazolylborate
dimethylsilanediylbis(2-n-hexyl-4-(4'-n-butylphenyl)indenyl)methylzirconiummethylbis(pentafluorophenyl)imidazolylborate
dimethylsilanediylbis(2-n-hexyl-4-(4'-hexylphenyl)indenyl)methylzirconiummethylbis(pentafluorophenyl)imidazolylborate
dimethylsilanediylbis(2-n-hexyl-4-(4'-sec-butylphenyl)indenyl)methylzirconiummethylbis(pentafluorophenyl)imidazolylborate
dimethylsilanediylbis(2-methyl-4,5-benzoindenyl)methylzirconiummethylbis(pentafluorophenyl)imidazolylborate
dimethylsilanediylbis(2-methyl-4,6-diisopropylindenyl)methylzirconiummethylbis(pentafluorophenyl)imidazolylborate
dimethylsilanediylbis(2,4,6-trimethylindenyl)methylzirconiummethylbis(pentafluorophenyl)imidazolylborate
dimethylsilanediylbis(2,5,6-trimethylindenyl)methylzirconiummethylbis(pentafluorophenyl)imidazolylborate
dimethylsilanediylbis(2,4,7-trimethylindenyl)methylzirconiummethylbis(pentafluorophenyl)imidazolylborate
dimethylsilanediylbis(2-methyl-5-isobutylindenyl)methylzirconiummethylbis(pentafluorophenyl)imidazolylborate
dimethylsilanediylbis(2-methyl-5-tert-butylindenyl)methylzirconiummethylbis(pentafluorophenyl)imidazolylborate methyl(phenyl)silanediylbis(indenyl)

methylzirconiummethylbis(pentafluorophenyl) imidazolylborate methyl(phenyl)silanediylbis(2-methylindenyl)methylzirconiummethylbis(pentafluorophenyl)imidazolylborate methyl(phenyl)silanediylbis(2-methylbenzindenyl) methylzirconiummethylbis(pentafluorophenyl) imidazolylborate methyl(phenyl)silanediylbis(4-phenylindenyl)methylzirconiummethylbis(pentafluorophenyl)imidazolylborate methyl(phenyl)silanediylbis(4-naphthylindenyl) methylzirconiummethylbis(pentafluorophenyl) imidazolylborate methyl(phenyl)silanediylbis(2-methyl-4-(1-naphthyl)indenyl) methylzirconiummethylbis(pentafluorophenyl) imidazolylborate methyl(phenyl)silanediylbis(2-methyl-4-(2-naphthyl)indenyl) methylzirconiummethylbis(pentafluorophenyl) imidazolylborate methyl(phenyl)silanediylbis(2-methyl-4-phenylindenyl)methylzirconiummethylbis(pentafluorophenyl)imidazolylborate methyl(phenyl) silanediylbis(2-methyl-4-tert-butylindenyl) methylzirconiummethylbis(pentafluorophenyl) imidazolylborate methyl(phenyl)silanediylbis(2-methyl-4-isopropylindenyl)methylzirconiummethylbis(pentafluorophenyl)imidazolylborate methyl(phenyl) silanediylbis(2-methyl-4-(1-naphthyl)indenyl) methylzirconiummethylbis(pentafluorophenyl) imidazolylborate methyl(phenyl)silanediylbis(2-methyl-4-ethylindenyl)methylzirconiummethylbis(pentafluorophenyl)imidazolylborate methyl(phenyl) silanediylbis(2-methyl-4-(acenaphthyl)indenyl) methylzirconiummethylbis(pentafluorophenyl) imidazolylborate methyl(phenyl)silanediylbis(2,4-dimethylindenyl)methylzirconiummethylbis(pentafluorophenyl)imidazolylborate methyl(phenyl) silanediylbis(2-ethylindenyl) methylzirconiummethylbis(pentafluorophenyl) imidazolylborate methyl(phenyl)silanediylbis(2-ethyl-4-ethylindenyl)methylzirconiummethylbis(pentafluorophenyl)imidazolylborate methyl(phenyl) silanediylbis(2-ethyl-4-phenylindenyl) methylzirconiummethylbis(pentafluorophenyl) imidazolylborate methyl(phenyl)silanediylbis(2-methyl-4,5-benzoindenyl)methylzirconiummethylbis(pentafluorophenyl)imidazolylborate methyl(phenyl) silanediylbis(2-methyl-4,6-diisopropylindenyl) methylzirconiummethylbis(pentafluorophenyl) imidazolylborate methyl(phenyl)silanediylbis(2,4,6-trimethylindenyl)methylzirconiummethylbis(pentafluorophenyl)imidazolylborate methyl(phenyl) silanediylbis(2,5,6-trimethylindenyl) methylzirconiummethylbis(pentafluorophenyl) imidazolylborate methyl(phenyl)silanediylbis(2,4,7-trimethylindenyl)methylzirconiummethylbis(pentafluorophenyl)imidazolylborate methyl(phenyl) silanediylbis(2-methyl-5-isobutylindenyl) methylzirconiummethylbis(pentafluorophenyl) imidazolylborate methyl(phenyl)silanediylbis(2-methyl-5-tert-butylindenyl)methylzirconiummethylbis(pentafluorophenyl)imidazolylborate diphenylmethylene(fluorenyl)(cyclopentadienyl) methylzirconiummethylbis(pentafluorophenyl) imidazolylborate dimethylmethylene(fluorenyl)(cyclopentadienyl)methylzirconiummethylbis(pentafluorophenyl)imidazolylborate methylphenylmethylene(fluorenyl)(cyclopentadienyl) methylzirconiummethylbis(pentafluorophenyl) imidazolylborate dimethylsilanediyl(3-tert-butylcyclopentadienyl)(fluorenyl) methylzirconiummethylbis(pentafluorophenyl) imidazolylborate diphenylsilanediyl(3-(trimethyl)cyclopentadienyl)(fluorenyl) methylzirconiummethylbis(pentafluorophenyl) imidazolylborate ethylenebis(indenyl) methylzirconiummethylbis(pentafluorophenyl) imidazolylborate ethylenebis(2-methylindenyl) methylzirconiummethylbis(pentafluorophenyl) imidazolylborate ethylenebis(2-methyl-4-phenylindenyl)methylzirconiummethylbis(pentafluorophenyl)imidazolylborate ethylenebis(2-methyl-4,5-benzindenyl)methylzirconiummethylbis(pentafluorophenyl)imidazolylborate ethylenebis(2-methyl-4,6-diisopropylindenyl) methylzirconiummethylbis(pentafluorophenyl) imidazolylborate 1,6-{bis[methylsilylbis(2-methyl-4-phenylindenyl)methylzirconiummethylbis(pentafluorophenyl)imidazolylborate}hexane 1,6-{bis(methylsilylbis(2-ethyl-4-phenylindenyl) methylzirconiummethylbis(pentafluorophenyl) imidazolylborate}hexane 1,6-{bis[methylsilylbis(2-methyl-4-naphthylphenylindenyl) methylzirconiummethylbis(pentafluorophenyl) imidazolylborate}hexane 1,6-{bis[methylsilylbis(2-methyl-4,5-benzoindenyl)methylzirconiummethylbis(pentafluorophenyl)imidazolylborate}hexane 1,6-{bis[methylsilyl(2-methyl-4-phenylindenyl)(2-methylindenylmethylzirconiummethylbis(pentafluorophenyl)imidazolylborate}hexane 1,6-{bis[methylsilylbis(2-methyl-4-phenylindenyl) methylzirconiummethylbis(pentafluorophenyl) imidazolylborate}ethane 1,6-{bis[methylsilylbis(2-ethyl-4-phenylindenyl)methylzirconiummethylbis(pentafluorophenyl)imidazolylborate}ethane 1,6-{bis[methylsilylbis(2-methyl-4-naphthylphenylindenyl) methylzirconiummethylbis(pentafluorophenyl) imidazolylborate}ethane 1,6-{bis[methylsilylbis(2-methyl-4,5-benzoindenyl)methylzirconiummethylbis(pentafluorophenyl)imidazolylborate}ethane 1,6-{bis[methylsilyl(2-methyl-4-phenylindenyl)(2-methylindenylmethylzirconiummethylbis(pentafluorophenyl)imidazolylborate}ethane tri(cyclopentadienyl)zirconiummethylbis(pentafluorophenyl)imidazolylborate tri(methylcyclopentadienyl)zirconiummethylbis(pentafluorophenyl)imidazolylborate tri(pentamethylcyclopentadienyl)zirconiummethylbis(pentafluorophenyl)imidazolylborate tri(n-butylcyclopentadienyl)zirconiummethylbis(pentafluorophenyl)imidazolylborate bis(cyclopentadienyl)methylzirconiurmnethylbis(pentafluorophenyl)isoindolylborate bis(methylcyclopentadienyl)methylzirconiummethylbis(pentafluorophenyl)isoindolylborate bis(pentamethylcyclopentadienyl)methylzirconiummethylbis(pentafluorophenyl)isoindolylborate bis(n-butyl-cyclopentadienyl) methylzirconiummethylbis(pentafluorophenyl) isoindolylborate bis(indenyl) methylzirconiummethylbis(pentafluorophenyl) isoindolylborate bis(2-methylindenyl) methylzirconiummethylbis(pentafluorophenyl) isoindolylborate bis(2-methylbenzindenyl) methylzirconiummethylbis(pentafluorophenyl) isoindolylborate (tert-butylamido)dimethyl (tetramethyl-η⁵-cyclopentadienyl)silanemethylzirconiummethylbis(pentafluorophenyl)isoindolylborate dimethylsilanediylbis(indenyl)methylzirconiummethylbis(pentafluorophenyl)isoindolylborate dimethylsilanediylbis(2-methylindenyl)methylzirconiummethylbis(pentafluorophenyl)isoindolylborate dimethylsilanediylbis(2-methylbenzindenyl)methylzirconiummethylbis(pentafluorophenyl)isoindolylborate dimethylsilanediylbis(4-phenylindenyl)methylzirconiummethylbis(pentafluorophenyl)isoindolylborate dimethylsilanediylbis(4-naphthylindenyl)methylzirconiummethylbis(pentafluorophenyl)isoindolylborate dimethylsilanediylbis(2-methyl-4-(1-naphthyl)indenyl)methylzirconiummethylbis(pentafluorophenyl)isoindolylborate dimethylsilanediylbis(2-methyl-4-(2-naphthyl)indenyl)methylzirconiummethylbis(pentafluorophenyl)isoindolylborate dimethylsilanediylbis(2-methyl-4-phenylindenyl)methylzirconiummethylbis(pentafluorophenyl)isoindolylborate dimethylsilanediylbis(2-methyl-4-tert-butylindenyl)methylzirconiummethylbis(pentafluorophenyl)isoindolylborate dimethylsilanediylbis(2-methyl-4-isopropylindenyl)methylzirconiummethylbis(pentafluorophenyl)isoindolylborate dimethylsilanediylbis(2-methyl-4-(1-naphthyl)indenyl)methylzirconiummethylbis(pentafluorophenyl)isoindolylborate dimethylsilanediylbis(2-methyl-4-ethylindenyl)methylzirconiummethylbis(pentafluorophenyl)isoindolylborate dimethylsilanediylbis(2-methyl-4-(acenaphthyl)indenyl)methylzirconiummethylbis(pentafluorophenyl)isoindolylborate dimethylsilanediylbis(2,4-dimethylindenyl)methylzirconiummethylbis(pentafluorophenyl)isoindolylborate dimethylsilanediylbis(2-ethylindenyl)methylzirconiummethylbis(pentafluorophenyl)isoindolylborate dimethylsilanediylbis(2-ethyl-4-ethylindenyl)methylzirconiummethylbis(pentafluorophenyl)isoindolylborate dimethylsilanediylbis(2-ethyl-4-phenylindenyl)methylzirconiummethylbis(pentafluorophenyl)isoindolylborate dimethylsilanediylbis(2-methyl-4-(4'-tert-butylphenyl)indenyl)methylzirconiummethylbis(pentafluorophenyl)isoindolylborate dimethylsilanediylbis(2-methyl-4-(4'-methylphenyl)indenyl)methylzirconiummethylbis(pentafluorophenyl)isoindolylborate dimethylsilanediylbis(2-methyl-4-(4'-ethylphenyl)indenyl)methylzirconiummethylbis(pentafluorophenyl)isoindolylborate dimethylsilanediylbis(2-methyl-4-(4'-n-propylphenyl)indenyl)methylzirconiummethylbis(pentafluorophenyl)isoindolylborate dimethylsilanediylbis(2-methyl-4-(4'-isopropylphenyl)indenyl)methylzirconiummethylbis(pentafluorophenyl)isoindolylborate dimethylsilanediylbis(2-methyl-4-(4'-n-butylphenyl)indenyl)methylzirconiummethylbis(pentafluorophenyl)isoindolylborate dimethylsilanediylbis(2-methyl-4-(4'-hexylphenyl)indenyl)methylzirconiummethylbis(pentafluorophenyl)isoindolylborate dimethylsilanediylbis(2-methyl-4-(4'-sec-butylphenyl)indenyl)methylzirconiummethylbis(pentafluorophenyl)isoindolylborate dimethylsilanediylbis(2-ethyl-4-(4'-tert-butylphenyl)indenyl)methylzirconiummethylbis(pentafluorophenyl)isoindolylborate dimethylsilanediylbis(2-ethyl-4-(4'-methylphenyl)indenyl)methylzirconiummethylbis(pentafluorophenyl)isoindolylborate dimethylsilanediylbis(2-ethyl-4-(4'-ethylphenyl)indenyl)methylzirconiummethylbis(pentafluorophenyl)isoindolylborate dimethylsilanediylbis(2-ethyl-4-(4'-n-propylphenyl)indenyl)methylzirconiummethylbis(pentafluorophenyl)isoindolylborate dimethylsilanediylbis(2-ethyl-4-(4'-isopropylphenyl)indenyl)methylzirconiummethylbis(pentafluorophenyl)isoindolylborate dimethylsilanediylbis(2-ethyl-4-(4'-n-butylphenyl)indenyl)methylzirconiummethylbis(pentafluorophenyl)isoindolylborate dimethylsilanediylbis(2-ethyl-4-(4'-hexylphenyl)indenyl)methylzirconiummethylbis(pentafluorophenyl)isoindolylborate dimethylsilanediylbis(2-ethyl-4-(4'-sec-butylphenyl)indenyl)methylzirconiummethylbis(pentafluorophenyl)isoindolylborate dimethylsilanediylbis(2-n-propyl-4-(4'-tert-butylphenyl)indenyl)methylzirconiummethylbis(pentafluorophenyl)isoindolylborate dimethylsilanediylbis(2-n-propyl-4-(4'-methylphenyl)indenyl)methylzirconiummethylbis(pentafluorophenyl)isoindolylborate dimethylsilanediylbis(2-n-propyl-4-(4'-ethylphenyl)indenyl)methyl zirconiummethylbis(pentafluorophenyl)isoindolylborate dimethylsilanediylbis(2-n-propyl-4-(4'-n-propylphenyl)indenylmethylzirconiummethylbis(pentafluorophenyl)isoindolylborate dimethylsilanediylbis(2-n-propyl-4-(4'-isopropylphenyl)indenyl)methylzirconiummethylbis(pentafluorophenyl)isoindolylborate dimethylsilanediylbis(2-n-propyl-4-(4'-n-butylphenyl)indenyl)methylzirconiummethylbis(pentafluorophenyl)isoindolylborate dimethylsilanediylbis(2-n-propyl-4-(4'-hexylphenyl)indenyl)methylzirconiummethylbis(pentafluorophenyl)isoindolylborate dimethylsilanediylbis(2-n-propyl-4-(4'-sec-butylphenyl)indenyl)methylzirconiummethylbis(pentafluorophenyl)isoindolylborate dimethylsilanediylbis(2-n-butyl-4-(4'-tert-butylphenyl)indenyl)methylzirconiummethylbis(pentafluorophenyl)isoindolylborate dimethylsilanediylbis(2-n-butyl-4-(4'-methylphenyl)indenyl)methylzirconiummethylbis(pentafluorophenyl)isoindolylborate dimethylsilanediylbis(2-n-butyl-4-(4'-ethylphenyl)indenyl)methylzirconiummethylbis(pentafluorophenyl)isoindolylborate dimethylsilanediylbis(2-n-butyl-4-(4'-n-propylphenyl)indenyl)methylzirconiummethylbis(pentafluorophenyl)isoindolylborate dimethylsilanediylbis(2-n-butyl-4-(4'-isopropylphenyl)indenyl)methylzirconiummethylbis(pentafluorophenyl)isoindolylborate dimethylsilanediylbis(2-n-butyl-4-(4'-n-butylphenyl)indenyl)methylzirconiummethylbis(pentafluorophenyl)isoindolylborate dimethylsilanediylbis(2-n-butyl-4-(4'-hexylphenyl)
indenyl)methylzirconiummethylbis
(pentafluorophenyl)isoindolylborate
dimethylsilanediylbis(2-n-butyl-4-(4'-sec-butylphenyl)
indenyl)methylzirconiummethylbis
(pentafluorophenyl)isoindolylborate
dimethylsilanediylbis(2-n-hexyl-4-(4'-tert-
butylphenyl)indenyl)methylzirconiummethylbis
(pentafluorophenyl)isoindolylborate
dimethylsilanediylbis(2-n-hexyl-4-(4'-methylphenyl)
indenyl)methylzirconiummethylbis
(pentafluorophenyl)isoindolylborate
dimethylsilanediylbis(2-n-hexyl-4-(4'-ethylphenyl)
indenyl)methylzirconiummethylbis
(pentafluorophenyl)isoindolylborate
dimethylsilanediylbis(2-n-hexyl-4-(4'-n-propylphenyl)
indenyl)methylzirconiummethylbis
(pentafluorophenyl)isoindolylborate
dimethylsilanediylbis(2-n-hexyl-4-(4'-
isopropylphenyl)indenyl)methylzirconiummethylbis
(pentafluorophenyl)isoindolylborate
dimethylsilanediylbis(2-n-hexyl-4-(4'-n-butylphenyl)
indenyl)methylzirconiummethylbis
(pentafluorophenyl)isoindolylborate
dimethylsilanediylbis(2-n-hexyl-4-(4'-hexylphenyl)
indenyl)methylzirconiummethylbis
(pentafluorophenyl)isoindolylborate
dimethylsilanediylbis(2-n-hexyl-4-(4'-sec-
butylphenyl)indenyl)methylzirconiummethylbis
(pentafluorophenyl)isoindolylborate
dimethylsilanediylbis(2-methyl-4,5-benzoindenyl)
methylzirconiummethylbis(pentafluorophenyl)
isoindolylborate dimethylsilanediylbis(2-methyl-4,6-
diisopropylindenyl)methylzirconiummethylbis
(pentafluorophenyl)isoindolylborate
dimethylsilanediylbis(2,4,6-trimethylindenyl)
methylzirconiummethylbis(pentafluorophenyl)
isoindolylborate dimethylsilanediylbis(2,5,6-
trimethylindenyl)methylzirconiummethylbis
(pentafluorophenyl)isoindolylborate
dimethylsilanediylbis(2,4,7-trimethylindenyl)
methylzirconiummethylbis(pentafluorophenyl)
isoindolylborate dimethylsilanediylbis(2-methyl-5-
isobutylindenyl)methylzirconiummethylbis
(pentafluorophenyl)isoindolylborate
dimethylsilanediylbis(2-methyl-5-tert-butylindenyl)
methylzirconiummethylbis(pentafluorophenyl)
isoindolylborate methyl(phenyl)silanediylbis(indenyl)
methylzirconiummethylbis(pentafluorophenyl)
isoindolylborate methyl(phenyl)silanediylbis(2-
methylindenyl)methylzirconiummethyl-bis
(pentafluorophenyl)isoindolylborate methyl(phenyl)
silanediylbis(2-methylbenzindenyl)
methylzirconiummethylbis(pentafluorophenyl)
isoindolylborate methyl(phenyl)silanediylbis(4-
phenylindenyl)methylzirconiummethylbis
(pentafluorophenyl)isoindolylborate methyl(phenyl)
silanediylbis(4-naphthylindenyl)
methylzirconiummethylbis(pentafluorophenyl)
isoindolylborate methyl(phenyl)silanediylbis(2-
methyl-4-(1-naphthyl)indenyl)
methylzirconiummethylbis(pentafluorophenyl)
isoindolylborate methyl(phenyl)silanediylbis(2-
methyl-4-(2-naphthyl)indenyl)
methylzirconiummethylbis(pentafluorophenyl)
isoindolylborate methyl(phenyl)silanediylbis(2-
methyl-4-phenylindenyl)methylzirconiummethylbis
(pentafluorophenyl)isoindolylborate methyl(phenyl)
silanediylbis(2-methyl-4-tert-butylindenyl)
methylzirconiummethylbis(pentafluorophenyl)
isoindolylborate methyl(phenyl)silanediylbis(2-
methyl-4-isopropylindenyl)methylzirconiummethylbis
(pentafluorophenyl)isoindolylborate methyl(phenyl)
silanediylbis(2-methyl-4-(1-naphthyl)indenyl)
methylzirconiummethylbis(pentafluorophenyl)
isoindolylborate methyl(phenyl)silanediylbis(2-
methyl-4-ethylindenyl)methylzirconiummethylbis
(pentafluorophenyl)isoindolylborate methyl(phenyl)
silanediylbis(2-methyl-4-(acenaphthyl)indenyl)
methylzirconiummethylbis(pentafluorophenyl)
isoindolylborate methyl(phenyl)silanediylbis(2,4-
dimethylindenyl)methylzirconium methylbis
(pentafluorophenyl)isoindolylborate methyl(phenyl)
silanediylbis(2-ethylindenyl)
methylzirconiummethylbis(pentafluorophenyl)
isoindolylborate methyl(phenyl)silanediylbis(2-ethyl-
4-ethylindenyl)methylzirconiummethylbis
(pentafluorophenyl)isoindolylborate methyl(phenyl)
silanediylbis(2-ethyl-4-phenylindenyl)
methylzirconiummethylbis(pentafluorophenyl)
isoindolylborate methyl(phenyl)silanediylbis(2-
methyl-4,5-benzoindenyl)methylzirconiummethylbis
(pentafluorophenyl)isoindolylborate methyl(phenyl)
silanediylbis(2-methyl-4,6-diisopropylindenyl)
methylzirconiummethylbis(pentafluorophenyl)
isoindolylborate methyl(phenyl)silanediylbis(2,4,6-
trimethylindenyl)methylzirconiummethylbis
(pentafluorophenyl)isoindolylborate methyl(phenyl)
silanediylbis(2,5,6-trimethylindenyl)
methylzirconiummethylbis(pentafluorophenyl)
isoindolylborate methyl(phenyl)silanediylbis(2,4,7-
trimethylindenyl)methylzirconiummethylbis
(pentafluorophenyl)isoindolylborate methyl(phenyl)
silanediylbis(2-methyl-5-isobutylindenyl)
methylzirconiummethylbis(pentafluorophenyl)
isoindolylborate methyl(phenyl)silanediylbis(2-
methyl-5-tert-butylindenyl)methylzirconiummethylbis
(pentafluorophenyl)isoindolylborate
diphenylmethylene(fluorenyl)(cyclopentadienyl)
methylzirconiummethylbis(pentafluorophenyl)
isoindolylborate dimethylmethylene(fluorenyl)
(cyclopentadienyl)methylzirconiummethylbis
(pentafluorophenyl)isoindolylborate
methylphenylmethylene(fluorenyl)(cyclopentadienyl)
methylzirconiummethylbis(pentafluorophenyl)
isoindolylborate dimethylsilanediyl(3-tert-
butylcyclopentadienyl)(fluorenyl)
methylzirconiummethylbis(pentafluorophenyl)
isoindolylborate diphenylsilanediyl(3-(trimethyl)
cyclopentadienyl)(fluorenyl)
methylzirconiummethylbis(pentafluorophenyl)
isoindolylborate ethylenebis(indenyl)
methylzirconiummethylbis(pentafluorophenyl)
isoindolylborate ethylenebis(2-methylindenyl)
methylzirconiummethylbis(pentafluorophenyl)
isoindolylborate ethylenebis(2-methyl-4-
phenylindenyl)methylzirconiummethylbis
(pentafluorophenyl)isoindolylborate ethylenebis(2-
methyl-4,5-benzindenyl)methylzirconiummethylbis
(pentafluorophenyl)isoindolylborate ethylenebis(2-
methyl-4,6-diisopropylindenyl)
methylzirconiummethylbis(pentafluorophenyl)
isoindolylborate 1,6-{bis[methylsilylbis(2-methyl-4-
phenylindenyl)methylzirconiummethylbis (pentafluorophenyl)isoindolylborate}hexane 1,6-{bis[methylsilylbis(2-ethyl-4-phenylindenyl)methylzirconiummethylbis(pentafluorophenyl)isoindolylborate}hexane 1,6-{bis[methylsilylbis(2-methyl-4-naphthylphenylindenyl)methylzirconiummethylbis(pentafluorophenyl)isoindolylborate}hexane 1,6-{bis[methylsilylbis(2-methyl-4,5-benzoindenyl)methylzirconiummethylbis(pentafluorophenyl)isoindolylborate}hexane 1,6-{bis[methylsilyl(2-methyl-4-phenylindenyl)(2-methylindenylmethylzirconiummethylbis(pentafluorophenyl)isoindolylborate}hexane 1,6-{bis[methylsilylbis(2-methyl-4-phenylindenyl)methylzirconiummethylbis(pentafluorophenyl)isoindolylborate}ethane 1,6-{bis[methylsilylbis(2-ethyl-4-phenylindenyl)methylzirconiummethylbis(pentafluorophenyl)isoindolylborate}ethane 1,6-{bis[methylsilylbis(2-methyl-4-naphthylphenylindenyl)methylzirconiummethylbis(pentafluorophenyl)isoindolylborate}ethane 1,6-{bis(methylsilylbis(2-methyl-4,5-benzoindenyl)methylzirconiummethylbis(pentafluorophenyl)isoindolylborate}ethane 1,6-{bis[methylsilyl(2-methyl-4-phenylindenyl)(2-methylindenylmethylzirconiummethylbis(pentafluorophenyl)isoindolylborate}ethane tri(cyclopentadienyl)zirconiummethylbis(pentafluorophenyl)isoindolylborate tri(methylcyclopentadienyl)zirconiummethylbis(pentafluorophenyl)isoindolylborate tri(pentamethylcyclopentadienyl)zirconiummethylbis(pentafluorophenyl)isoindolylborate tri(n-butylcyclopentadienyl)zirconiummethylbis(pentafluorophenyl)isoindolylborate bis(cyclopentadienyl)methylzirconiummethylbis(pentafluorophenyl)benzimidazolylborate bis(methylcyclopentadienyl)methylzirconiummethylbis(pentafluorophenyl)benzimidazolylborate bis(pentamethylcyclopentadienyl)methylzirconiummethylbis(pentafluorophenyl)benzimidazolylborate bis(n-butylcyclopentadienyl)methylzirconiummethylbis(pentafluorophenyl)benzimidazolylborate bis(indenyl)methylzirconiummethylbis(pentafluorophenyl)benzimidazolylborate bis(2-methylindenyl)methylzirconiummethylbis(pentafluorophenyl)benzimidazolylborate bis(2-methylbenzindenyl)methylzirconiummethylbis(pentafluorophenyl)benzimidazolylborate (tert-butylamido)dimethyl(tetramethyl-η$^5$-cyclopentadienyl)silanemethylzirconiummethylbis(pentafluorophenyl)benzimidazolylborate dimethylsilanediylbis(indenyl)methylzirconiummethylbis(pentafluorophenyl)benzimidazolylborate dimethylsilanediylbis(2-methylindenyl)methylzirconiummethylbis(pentafluorophenyl)benzimidazolylborate dimethylsilanediylbis(2-methylbenzindenyl)methylzirconiummethylbis(pentafluorophenyl)benzimidazolylborate dimethylsilanediylbis(4-phenylindenyl)methylzirconiummethylbis(pentafluorophenyl)benzimidazolylborate dimethylsilanediylbis(4-naphthylindenyl)methylzirconiummethylbis(pentafluorophenyl)benzimidazolylborate dimethylsilanediylbis(2-methyl-4-(1-naphthyl)indenyl)methylzirconiummethylbis(pentafluorophenyl)benzimidazolylborate dimethylsilanediylbis(2-methyl-4-(2-naphthyl)indenyl)methylzirconiummethylbis(pentafluorophenyl)benzimidazolylborate dimethylsilanediylbis(2-methyl-4-phenylindenyl)methylzirconiummethylbis(pentafluorophenyl)benzimidazolylborate dimethylsilanediylbis(2-methyl-4-tert-butylindenyl)methylzirconiummethylbis(pentafluorophenyl)benzimidazolylborate dimethylsilanediylbis(2-methyl-4-isopropylindenyl)methylzirconiummethylbis(pentafluorophenyl)benzimidazolylborate dimethylsilanediylbis(2-methyl-4-(1-naphthyl)indenyl)methylzirconiummethylbis(pentafluorophenyl)benzimidazolylborate dimethylsilanediylbis(2-methyl-4-ethylindenyl)methylzirconiummethylbis(pentafluorophenyl)benzimidazolylborate dimethylsilanediylbis(2-methyl-4-(acenaphthyl)indenyl)methylzirconiummethylbis(pentafluorophenyl)benzimidazolylborate dimethylsilanediylbis(2,4-dimethylindenyl)methylzirconiummethylbis(pentafluorophenyl)benzimidazolylborate dimethylsilanediylbis(2-ethylindenyl)methylzirconiummethylbis(pentafluorophenyl)benzimidazolylborate dimethylsilanediylbis(2-ethyl-4-ethylindenyl)methylzirconiummethylbis(pentafluorophenyl)benzimidazolylborate dimethylsilanediylbis(2-ethyl-4-phenylindenyl)methylzirconiummethylbis(pentafluorophenyl)benzimidazolylborate dimethylsilanediylbis(2-methyl-4-(4'-tert-butylphenyl)indenyl)methylzirconiummethylbis(pentafluorophenyl)benzimidazolylborate dimethylsilanediylbis(2-methyl-4-(4'-methylphenyl)indenyl)methylzirconiummethylbis(pentafluorophenyl)benzimidazolylborate dimethylsilanediylbis(2-methyl-4-(4'-ethylphenyl)indenyl)methylzirconiummethylbis(pentafluorophenyl)benzimidazolylborate dimethylsilanediylbis(2-methyl-4-(4'-n-propylphenyl)indenyl)methylzirconiummethylbis(pentafluorophenyl)benzimidazolylborate dimethylsilanediylbis(2-methyl-4-(4'-isopropylphenyl)indenyl)methylzirconiummethylbis(pentafluorophenyl)benzimidazolylborate dimethylsilanediylbis(2-methyl-4-(4'-n-butylphenyl)indenyl)methylzirconiummethylbis(pentafluorophenyl)benzimidazolylborate dimethylsilanediylbis(2-methyl-4-(4'-hexylphenyl)indenyl)methylzirconiummethylbis(pentafluorophenyl)benzimidazolylborate dimethylsilanediylbis(2-methyl-4-(4'-sec-butylphenyl)indenyl)methylzirconiummethylbis(pentafluorophenyl)benzimidazolylborate dimethylsilanediylbis(2-ethyl-4-(4'-tert-butylphenyl)indenyl)methylzirconiummethylbis(pentafluorophenyl)benzimidazolylborate dimethylsilanediylbis(2-ethyl-4-(4'-methylphenyl)indenyl)methylzirconiummethylbis(pentafluorophenyl)benzimidazolylborate dimethylsilanediylbis(2-ethyl-4-(4'-ethylphenyl)indenyl)methylzirconiummethylbis(pentafluorophenyl)benzimidazolylborate dimethylsilanediylbis(2-ethyl-4-(4'-n-propylphenyl)indenyl)methylzirconiummethylbis(pentafluorophenyl)benzimidazolylborate dimethylsilanediylbis(2-ethyl-4-(4'-isopropylphenyl)indenyl)methylzirconiummethylbis(pentafluorophenyl)benzimidazolylborate dimethylsilanediylbis(2-ethyl-4-(4'-n-butylphenyl)indenyl)methylzirconiummethylbis (pentafluorophenyl)benzimidazolylborate
dimethylsilanediylbis(2-ethyl-4-(4'-hexylphenyl)
indenyl)methylzirconiummethylbis
(pentafluorophenyl)benzimidazolylborate
dimethylsilanediylbis(2-ethyl-4-(4'-sec-butylphenyl)
indenyl)methylzirconiummethylbis
(pentafluorophenyl)benzimidazolylborate
dimethylsilanediylbis(2-n-propyl-4-(4'-tert-butylphenyl)indenyl)methylzirconiummethylbis
(pentafluorophenyl)benzimidazolylborate
dimethylsilanediylbis(2-n-propyl-4-(4'-methylphenyl)
indenyl)methylzirconiummethylbis
(pentafluorophenyl)benzimidazolylborate
dimethylsilanediylbis(2-n-propyl-4-(4'-ethylphenyl)
indenyl)methylzirconiummethylbis
(pentafluorophenyl)benzimidazolylborate
dimethylsilanediylbis(2-n-propyl-4-(4'-n-propylphenyl)indenyl)methylzirconiummethylbis
(pentafluorophenyl)benzimidazolylborate
dimethylsilanediylbis(2-n-propyl-4-(4'-isopropylphenyl)indenyl)methylzirconiummethylbis
(pentafluorophenyl)benzimidazolylborate
dimethylsilanediylbis(2-n-propyl-4-(4'-n-butylphenyl)
indenyl)methylzirconiummethylbis
(pentafluorophenyl)benzimidazolylborate
dimethylsilanediylbis(2-n-propyl-4-(4'-hexylphenyl)
indenyl)methylzirconiummethylbis
(pentafluorophenyl)benzimidazolylborate
dimethylsilanediylbis(2-n-propyl-4-(4'-sec-butylphenyl)indenyl)methylzirconiummethylbis
(pentafluorophenyl)benzimidazolylborate
dimethylsilanediylbis(2-n-butyl-4-(4'-tert-butylphenyl)
indenyl)methylzirconiummethylbis
(pentafluorophenyl)benzimidazolylborate
dimethylsilanediylbis(2-n-butyl-4-(4'-methylphenyl)
indenyl)methylzirconiummethylbis
(pentafluorophenyl)benzimidazolylborate
dimethylsilanediylbis(2-n-butyl-4-(4'-ethylphenyl)
indenyl)methylzirconiummethylbis
(pentafluorophenyl)benzimidazolylborate
dimethylsilanediylbis(2-n-butyl-4-(4'-n-propylphenyl)
indenyl)methylzirconiummethylbis
(pentafluorophenyl)benzimidazolylborate
dimethylsilanediylbis(2-n-butyl-4-(4'-isopropylphenyl)indenyl)methylzirconiummethylbis
(pentafluorophenyl)benzimidazolylborate
dimethylsilanediylbis(2-n-butyl-4-(4'-n-butylphenyl)
indenyl)methylzirconiummethylbis
(pentafluorophenyl)benzimidazolylborate
dimethylsilanediylbis(2-n-butyl-4-(4'-hexylphenyl)
indenyl)methylzirconiummethylbis
(pentafluorophenyl)benzimidazolylborate
dimethylsilanediylbis(2-n-butyl-4-(4'-sec-butylphenyl)
indenyl)methylzirconiummethylbis
(pentafluorophenyl)benzimidazolylborate
dimethylsilanediylbis(2-n-hexyl-4-(4'-tert-butylphenyl)indenyl)methylzirconiummethylbis
(pentafluorophenyl)benzimidazolylborate
dimethylsilanediylbis(2-n-hexyl-4-(4'-methylphenyl)
indenyl)methylzirconiummethylbis
(pentafluorophenyl)benzimidazolylborate
dimethylsilanediylbis(2-n-hexyl-4-(4'-ethylphenyl)
indenyl)methylzirconiummethylbis
(pentafluorophenyl)benzimidazolylborate
dimethylsilanediylbis(2-n-hexyl-4-(4'-n-propylphenyl)
indenyl)methylzirconiummethylbis
(pentafluorophenyl)benzimidazolyllborate
dimethylsilanediylbis(2-n-hexyl-4-(4'-isopropylphenyl)indenyl)methylzirconiummethylbis
(pentafluorophenyl)benzimidazolylborate
dimethylsilanediylbis(2-n-hexyl-4-(4'-n-butylphenyl)
indenyl)methylzirconiummethylbis
(pentafluorophenyl)benzimidazolylborate
dimethylsilanediylbis(2-n-hexyl-4-(4'-hexylphenyl)
indenyl)methylzirconiummethylbis
(pentafluorophenyl)benzimidazolylborate
dimethylsilanediylbis(2-n-hexyl-4-(4'-sec-butylphenyl)indenyl)methylzirconiummethylbis
(pentafluorophenyl)benzimidazolylborate
dimethylsilanediylbis(2-methyl-4,5-benzoindenyl)
methylzirconiummethylbis(pentafluorophenyl)
benzimidazolylborate dimethylsilanediylbis(2-methyl-4,6-diisopropylindenyl)methylzirconiummethylbis
(pentafluorophenyl)benzimidazolylborate
dimethylsilanediylbis(2,4,6-trimethylindenyl)
methylzirconiummethylbis(pentafluorophenyl)
benzimidazolylborate dimethylsilanediylbis(2,5,6-trimethylindenyl)methylzirconiummethylbis
(pentafluorophenyl)benzimidazolylborate
dimethylsilanediylbis(2,4,7-trimethylindenyl)
methylzirconiummethylbis(pentafluorophenyl)
benzimidazolylborate dimethylsilanediylbis(2-methyl-5-isobutylindenyl)methylzirconiummethylbis
(pentafluorophenyl)benzimidazolylborate
dimethylsilanediylbis(2-methyl-5-tert-butylindenyl)
methylzirconiummethylbis(pentafluorophenyl)
benzimidazolylborate methyl(phenyl)silanediylbis
(indenyl)methylzirconiummethylbis
(pentafluorophenyl)benzimidazolylborate methyl
(phenyl)silanediylbis(2-methylindenyl)
methylzirconiummethylbis(pentafluorophenyl)
benzimidazolylborate methyl(phenyl)silanediylbis(2-methylbenzindenyl)methylzirconiummethylbis
(pentafluorophenyl)benzimidazolylborate methyl
(phenyl)silanediylbis(4-phenylindenyl)
methylzirconiummethylbis(pentafluorophenyl)
benzimidazolylborate methyl(phenyl)silanediylbis(4-naphthylindenyl)methylzirconiummethylbis
(pentafluorophenyl)benzimidazolylborate methyl
(phenyl)silanediylbis(2-methyl-4-(1-naphthyl)indenyl)
methylzirconiummethylbis(pentafluorophenyl)
benzimidazolylborate methyl(phenyl)silanediylbis(2-methyl-4-(2-naphthyl)indenyl)
methylzirconiummethylbis(pentafluorophenyl)
benzimidazolylborate methyl(phenyl)silanediylbis(2-methyl-4-phenylindenyl)methylzirconiummethylbis
(pentafluorophenyl)benzimidazolylborate methyl
(phenyl)silanediylbis(2-methyl-4-tert-butylindenyl)
methylzirconiummethylbis(pentafluorophenyl)
benzimidazolylborate methyl(phenyl)silanediylbis(2-methyl-4-isopropylindenyl)methylzirconiummethylbis
(pentafluorophenyl)benzimidazolylborate methyl
(phenyl)silanediylbis(2-methyl-4-(1-naphthyl)indenyl)
methylzirconiummethylbis(pentafluorophenyl)
benzimidazolylborate methyl(phenyl)silanediylbis(2-methyl-4-ethylindenyl)methylzirconiummethylbis
(pentafluorophenyl)benzimidazolylborate methyl
(phenyl)silanediylbis(2-methyl-4-(acenaphthyl)
indenyl)methylzirconiummethylbis
(pentafluorophenyl)benzimidazolylborate methyl
(phenyl)silanediylbis(2,4-dimethylindenyl)
methylzirconiummethylbis(pentafluorophenyl)
benzimidazolylborate methyl(phenyl)silanediylbis(2-ethylindenyl)methylzirconiummethylbis (pentafluorophenyl)benzimidazolylborate methyl(phenyl)silanediylbis(2-ethyl-4-ethylindenyl)methylzirconiummethylbis(pentafluorophenyl)benzimidazolylborate methyl(phenyl)silanediylbis(2-ethyl-4-phenylindenyl)methylzirconiummethylbis(pentafluorophenyl)benzimidazolylborate methyl(phenyl)silanediylbis(2-methyl-4,5-benzoindenyl)methylzirconiummethylbis(pentafluorophenyl)benzimidazolylborate methyl(phenyl)silanediylbis(2-methyl-4,6-diisopropylindenyl)methylzirconiummethylbis(pentafluorophenyl)benzimidazolylborate methyl(phenyl)silanediylbis(2,4,6-trimethylindenyl)methylzirconiummethylbis(pentafluorophenyl)benzimidazolylborate methyl(phenyl)silanediylbis(2,5,6-trimethylindenyl)methylzirconiummethylbis(pentafluorophenyl)benzimidazolylborate methyl(phenyl)silanediylbis(2,4,7-trimethylindenyl)methylzirconiummethylbis(pentafluorophenyl)benzimidazolylborate methyl(phenyl)silanediylbis(2-methyl-5-isobutylindenyl)methylzirconiummethylbis(pentafluorophenyl)benzimidazolylborate methyl(phenyl)silanediylbis(2-methyl-5-tert-butylindenyl)methylzirconiummethylbis(pentafluorophenyl)benzimidazolylborate diphenylmethylene(fluorenyl)(cyclopentadienyl)methylzirconiummethylbis(pentafluorophenyl)benzimidazolylborate dimethylmethylene(fluorenyl)(cyclopentadienyl)methylzirconiummethylbis(pentafluorophenyl)benzimidazolylborate methylphenylmethylene(fluorenyl)(cyclopentadienyl)methylzirconiummethylbis(pentafluorophenyl)benzimidazolylborate dimethylsilanediyl(3-tert-butylcyclopentadienyl)(fluorenyl)methylzirconiummethylbis(pentafluorophenyl)benzimidazolylborate diphenylsilanediyl(3-(trimethyl)cyclopentadienyl)(fluorenyl)methylzirconiummethylbis(pentafluorophenyl)benzimidazolylborate ethylenebis(indenyl)methylzirconiummethylbis(pentafluorophenyl)benzimidazolylborate ethylenebis(2-methylindenyl)methylzirconiummethylbis(pentafluorophenyl)benzimidazolylborate ethylenebis(2-methyl-4-phenylindenyl)methylzirconiummethylbis(pentafluorophenyl)benzimidazolylborate ethylenebis(2-methyl-4,5-benzindenyl)methylzirconiummethylbis(pentafluorophenyl)benzimidazolylborate ethylenebis(2-methyl-4,6-diisopropylindenyl)methylzirconiummethylbis(pentafluorophenyl)benzimidazolylborate 1,6-{bis[methylsilylbis(2-methyl-4-phenylindenyl)methylzirconiummethylbis(pentafluorophenyl)benzimidazolylborate}hexane 1,6-{bis[methylsilylbis(2-ethyl-4-phenylindenyl)methylzirconiummethylbis(pentafluorophenyl)benzimidazolylborate}hexane 1,6-{bis[methylsilylbis(2-methyl-4-naphthylphenylindenyl)methylzirconiummethylbis(pentafluorophenyl)benzimidazolylborate}hexane 1,6-{bis[methylsilylbis(2-methyl-4,5-benzoindenyl)methylzirconiummethylbis(pentafluorophenyl)benzimidazolylborate}hexane 1,6-{bis[methylsilyl(2-methyl-4-phenylindenyl)(2-methylindenylmethylzirconiummethylbis(pentafluorophenyl)benzimidazolylborate}hexane 1,6-{bis[methylsilylbis(2-methyl-4-phenylindenyl)methylzirconiummethylbis(pentafluorophenyl)benzimidazolylborate}ethane 1,6-{bis[methylsilylbis(2-ethyl-4-phenylindenyl)methylzirconiummethylbis(pentafluorophenyl)benzimidazolylborate}ethane 1,6-{bis[methylsilylbis(2-methyl-4-naphthylphenylindenyl)methylzirconiummethylbis(pentafluorophenyl)benzimidazolylborate}ethane 1,6-{bis[methylsilylbis(2-methyl-4,5-benzoindenyl)methylzirconiummethylbis(pentafluorophenyl)benzimidazolylborate}ethane 1,6-{bis[methylsilyl(2-methyl-4-phenylindenyl)(2-methylindenylmethylzirconiummethylbis(pentafluorophenyl)benzimidazolylborate}ethane tri(cyclopentadienyl)zirconiummethylbis(pentafluorophenyl)benzimidazolylborate tri(methylcyclopentadienyl)zirconiummethylbis(pentafluorophenyl)benzimidazolylborate tri(pentamethylcyclopentadienyl)zirconiummethylbis(pentafluorophenyl)benzimidazolylborate tri(n-butylcyclopentadienyl)zirconiummethylbis(pentafluorophenyl)benzimidazolylborate bis(cyclopentadienyl)methylzirconiummethylbis(pentafluorophenyl)indolylborate bis(methylcyclopentadienyl)methylzirconiummethylbis(pentafluorophenyl)indolylborate bis(pentamethylcyclopentadienyl)methylzirconiummethylbis(pentafluorophenyl)indolylborate bis(n-butylcyclopentadienyl)methylzirconiummethylbis(pentafluorophenyl)indolylborate bis(indenyl)methylzirconiummethylbis(pentafluorophenyl)indolylborate bis(2-methylindenyl)methylzirconiummethylbis(pentafluorophenyl)indolylborate bis(2-methylbenzindenyl)methylzirconiummethylbis(pentafluorophenyl)indolylborate (tert-butylamido)dimethyl(tetramethyl-$\eta^5$-cyclopentadienyl)silanemethylzirconiummethylbis(pentafluorophenyl)indolylborate dimethylsilanediylbis(indenyl)methylzirconiummethylbis(pentafluorophenyl)indolylborate dimethylsilanediylbis(2-methylindenyl)methylzirconiummethylbis(pentafluorophenyl)indolylborate dimethylsilanediylbis(2-methylbenzindenyl)methylzirconiummethylbis(pentafluorophenyl)indolylborate dimethylsilanediylbis(4-phenylindenyl)methylzirconiummethylbis(pentafluorophenyl)indolylborate dimethylsilanediylbis(4-naphthylindenyl)methylzirconiummethylbis(pentafluorophenyl)indolylborate dimethylsilanediylbis(2-methyl-4-(1-naphthyl)indenyl)methylzirconiummethylbis(pentafluorophenyl)indolylborate dimethylsilanediylbis(2-methyl-4-(2-naphthyl)indenyl)methylzirconiummethylbis(pentafluorophenyl)indolylborate dimethylsilanediylbis(2-methyl-4-phenylindenyl)methylzirconiummethylbis(pentafluorophenyl)indolylborate dimethylsilanediylbis(2-methyl-4-tert-butylindenyl)methylzirconiummethylbis(pentafluorophenyl)indolylborate dimethylsilanediylbis(2-methyl-4-isopropylindenyl)methylzirconiummethylbis(pentafluorophenyl)indolylborate dimethylsilanediylbis(2-methyl-4-(1-naphthyl)indenyl)methylzirconiummethylbis(pentafluorophenyl)indolylborate dimethylsilanediylbis(2-methyl-4-ethylindenyl)methylzirconiummethylbis(pentafluorophenyl)indolylborate dimethylsilanediylbis(2-methyl-4-(acenaphthyl)indenyl)methylzirconiummethylbis(pentafluorophenyl)indolylborate dimethylsilanediylbis(2,4-dimethylindenyl)methylzirconiummethylbis(pentafluorophenyl)indolylborate dimethylsilanediylbis(2-ethylindenyl)methylzirconiummethylbis(pentafluorophenyl)indolylborate dimethylsilanediylbis(2-ethyl-4-ethylindenyl)methylzirconiummethylbis(pentafluorophenyl)indolylborate dimethylsilanediylbis(2-ethyl-4-phenylindenyl)methylzirconiummethylbis(pentafluorophenyl)indolylborate dimethylsilanediylbis(2-methyl-4-(4'-tert-butylphenyl)indenyl)methylzirconiummethylbis(pentafluorophenyl)indolylborate dimethylsilanediylbis(2-methyl-4-(4'-methylphenyl)indenyl)methylzirconiummethylbis(pentafluorophenyl)indolylborate dimethylsilanediylbis(2-methyl-4-(4'-ethylphenyl)indenyl)methylziconiummethylbis(pentafluorophenyl)indolylborate dimethylsilanediylbis(2-methyl-4-(4'-n-propylphenyl)indenyl)methylzirconiummethylbis(pentafluorophenyl)indolylborate dimethylsilanediylbis(2-methyl-4-(4'-isopropylphenyl)indenyl)methylzirconiummethylbis(pentafluorophenyl)indolylborate dimethylsilanediylbis(2-methyl-4-(4'-n-butylphenyl)indenyl)methylzirconiummethylbis(pentafluorophenyl)indolylborate dimethylsilanediylbis(2-methyl-4-(4'-hexylphenyl)indenyl)methylzirconiummethylbis(pentafluorophenyl)indolylborate dimethylsilanediylbis(2-methyl-4-(4'-sec-butylphenyl)indenyl)methylzirconiummethylbis(pentafluorophenyl)indolylborate dimethylsilanediylbis(2-ethyl-4-(4'-tert-butylphenyl)indenyl)methylzirconiummethylbis(pentafluorophenyl)indolylborate dimethylsilanediylbis(2-ethyl-4-(4'-methylphenyl)indenyl)methylzirconiummethylbis(pentafluorophenyl)indolylborate dimethylsilanediylbis(2-ethyl-4-(4'-ethylphenyl)indenyl)methylzirconiummethylbis(pentafluorophenyl)indolylborate dimethylsilanediylbis(2-ethyl-4-(4'-n-propylphenyl)indenyl)methylzirconiummethylbis(pentafluorophenyl)indolylborate dimethylsilanediylbis(2-ethyl-4-(4'-isopropylphenyl)indenyl)methylzirconiummethylbis(pentafluorophenyl)indolylborate dimethylsilanediylbis(2-ethyl-4-(4'-n-butylphenyl)indenyl)methylzirconiummethylbis(pentafluorophenyl)indolylborate dimethylsilanediylbis(2-ethyl-4-(4'-hexylphenyl)indenyl)methylzirconiummethylbis(pentafluorophenyl)indolylborate dimethylsilanediylbis(2-ethyl-4-(4'-sec-butylphenyl)indenyl)methylzirconiummethylbis(pentafluorophenyl)indolylborate dimethylsilanediylbis(2-n-propyl-4-(4'-tert-butylphenyl)indenyl)methylzirconiummethylbis(pentafluorophenyl)indolylborate dimethylsilanediylbis(2-n-propyl-4-(4'-methylphenyl)indenyl)methylzirconiummethylbis(pentafluorophenyl)indolylborate dimethylsilanediylbis(2-n-propyl-4-(4'-ethylphenyl)indenyl)methylzirconiummethylbis(pentafluorophenyl)indolylborate dimethylsilanediylbis(2-n-propyl-4-(4'-n-propylphenyl)indenyl)methylzirconiummethylbis(pentafluorophenyl)indolylborate dimethylsilanediylbis(2-n-propyl-4-(4'-isopropylphenyl)indenyl)methylzirconiummethylbis(pentafluorophenyl)indolylborate dimethylsilanediylbis(2-n-propyl-4-(4'-n-butylphenyl)indenyl)methylzirconiummethylbis(pentafluorophenyl)indolylborate dimethylsilanediylbis(2-n-propyl-4-(4'-hexylphenyl)indenyl)methylzirconiummethylbis(pentafluorophenyl)indolylborate dimethylsilanediylbis(2-n-propyl-4-(4'-sec-butylphenyl)indenyl)methylzirconiummethylbis(pentafluorophenyl)indolylborate dimethylsilanediylbis(2-n-butyl-4-(4'-tert-butylphenyl)indenyl)methylzirconiummethylbis(pentafluorophenyl)indolylborate dimethylsilanediylbis(2-n-butyl-4-(4'-methylphenyl)indenyl)methylzirconiummethylbis(pentafluorophenyl)indolylborate dimethylsilanediylbis(2-n-butyl-4-(4'-ethylphenyl)indenyl)methylzirconiummethylbis(pentafluorophenyl)indolylborate dimethylsilanediylbis(2-n-butyl-4-(4'-n-propylphenyl)indenyl)methylzirconiummethylbis(pentafluorophenyl)indolylborate dimethylsilanediylbis(2-n-butyl-4-(4'-isopropylphenyl)indenyl)methylzirconiummethylbis(pentafluorophenyl)indolylborate dimethylsilanediylbis(2-n-butyl-4-(4'-n-butylphenyl)indenyl)methylzirconiummethylbis(pentafluorophenyl)indolylborate dimethylsilanediylbis(2-n-butyl-4-(4'-hexylphenyl)indenyl)methylzirconiummethylbis(pentafluorophenyl)indolylborate dimethylsilanediylbis(2-n-butyl-4-(4'-sec-butylphenyl)indenyl)methylzirconiummethylbis(pentafluorophenyl)indolylborate dimethylsilanediylbis(2-n-hexyl-4-(4'-tert-butylphenyl)indenyl)methylzirconiummethylbis(pentafluorophenyl)indolylborate dimethylsilanediylbis(2-n-hexyl-4-(4'-methylphenyl)indenyl)methylzirconiummethylbis(pentafluorophenyl)indolylborate dimethylsilanediylbis(2-n-hexyl-4-(4'-ethylphenyl)indenyl)methylzirconiummethylbis(pentafluorophenyl)indolylborate dimethylsilanediylbis(2-n-hexyl-4-(4'-n-propylphenyl)indenyl)methylzirconiummethylbis(pentafluorophenyl)indolylborate dimethylsilanediylbis(2-n-hexyl-4-(4'-isopropylphenyl)indenyl)methylzirconiummethylbis(pentafluorophenyl)indolylborate dimethylsilanediylbis(2-n-hexyl-4-(4'-n-butylphenyl)indenyl)methylzirconiummethylbis(pentafluorophenyl)indolylborate dimethylsilanediylbis(2-n-hexyl-4-(4'-hexylphenyl)indenyl)methylzirconiummethylbis(pentafluorophenyl)indolylborate dimethylsilanediylbis(2-n-hexyl-4-(4'-sec-butylphenyl)indenyl)methylzirconiummethylbis(pentafluorophenyl)indolylborate dimethylsilanediylbis(2-methyl-4,5-benzoindenyl)methylzirconiummethylbis(pentafluorophenyl)indolylborate dimethylsilanediylbis(2-methyl-4,6-diisopropylindenyl)methylzirconiummethylbis(pentafluorophenyl)indolylborate dimethylsilanediylbis(2,4,6-trimethylindenyl)

methylzirconiummethylbis(pentafluorophenyl)indolylborate dimethylsilanediylbis(2,5,6-trimethlindenyl)methylzirconiummethylbis(pentafluorophenyl)indolylborate dimethylsilanediylbis(2,4,7-trimethylindenyl) methylzirconiummethylbis(pentafluorophenyl)indolylborate dimethylsilanediylbis(2-methyl-5-isobutylindenyl)methylzirconiummethylbis(pentafluorophenyl)indolylborate dimethylsilanediylbis(2-methyl-5-tert-butylindenyl) methylzirconiummethylbis(pentafluorophenyl)indolylborate methyl(phenyl)silanediylbis(indenyl)methylzirconiummethylbis(pentafluorophenyl)indolylborate methyl(phenyl)silanediylbis(2-methylindenyl)methylzirconiummethylbis(pentafluorophenyl)indolylborate methyl(phenyl)silanediylbis(2-methylbenzindenyl) methylzirconiummethylbis(pentafluorophenyl)indolylborate methyl(phenyl)silanediylbis(4-phenylindenyl)methylzirconiummethylbis(pentafluorophenyl)indolylborate methyl(phenyl)silanediylbis(4-naphthylindenyl) methylzirconiummethylbis(pentafluorophenyl)indolylborate methyl(phenyl)silanediylbis(2-methyl-4-(1-naphthyl)indenyl)methylzirconiummethylbis(pentafluorophenyl)indolylborate methyl(phenyl)silanediylbis(2-methyl-4-(2-naphthyl)indenyl)methylzirconiummethylbis(pentafluorophenyl)indolylborate methyl(phenyl)silanediylbis(2-methyl-4-phenylindenyl)methylzirconiummethylbis(pentafluorophenyl)indolylborate methyl(phenyl)silanediylbis(2-methyl-4-tert-butylindenyl)methylzirconiummethylbis(pentafluorophenyl)indolylborate methyl(phenyl)silanediylbis(2-methyl-4-isopropylindenyl)methylzirconiummethylbis(pentafluorophenyl)indolylborate methyl(phenyl)silanediylbis(2-methyl-4-(1-naphthyl)indenyl)methylzirconiummethylbis(pentafluorophenyl)indolylborate methyl(phenyl)silanediylbis(2-methyl-4-ethylindenyl)methylzirconiummethylbis(pentafluorophenyl)indolylborate methyl(phenyl)silanediylbis(2-methyl-4-(acenaphthyl)indenyl)methylzirconiummethylbis(pentafluorophenyl)indolylborate methyl(phenyl)silanediylbis(2,4-dimethylindenyl)methylzirconiummethylbis(pentafluorophenyl)indolylborate methyl(phenyl)silanediylbis(2-ethylindenyl)methylzirconiummethylbis(pentafluorophenyl)indolylborate methyl(phenyl)silanediylbis(2-ethyl-4-ethylindenyl)methylzirconiummethylbis(pentafluorophenyl)indolylborate methyl(phenyl)silanediylbis(2-ethyl-4-phenylindenyl)methylzirconiummethylbis(pentafluorophenyl)indolylborate methyl(phenyl)silanediylbis(2-methyl-4,5-benzoindenyl)methylzirconiummethylbis(pentafluorophenyl)indolylborate methyl(phenyl)silanediylbis(2-methyl-4,6-diisopropylindenyl)methylzirconiummethylbis(pentafluorophenyl)indolylborate methyl(phenyl)silanediylbis(2,4,6-trimethylindenyl)methylzirconiummethylbis(pentafluorophenyl)indolylborate methyl(phenyl)silanediylbis(2,5,6-trimethylindenyl) methylzirconiummethylbis(pentafluorophenyl)indolylborate methyl(phenyl)silanediylbis(2,4,7-trimethylindenyl)methylzirconiummethylbis(pentafluorophenyl)indolylborate methyl(phenyl)silanediylbis(2-methyl-5-isobutylindenyl) methylzirconiummethylbis(pentafluorophenyl)indolylborate methyl(phenyl)silanediylbis(2-methyl-5-tert-butylindenyl)methylzirconiummethylbis(pentafluorophenyl)indolylborate diphenylmethylene(fluorenyl)(cyclopentadienyl)methylzirconiummethylbis(pentafluorophenyl)indolylborate dimethylmethylene(fluorenyl)(cyclopentadienyl)methylzirconiummethylbis(pentafluorophenyl)indolylborate methylphenylmethylene(fluorenyl)(cyclopentadienyl)methylzirconiummethylbis(pentafluorophenyl)indolylborate dimethylsilanediyl(3-tert-butylcyclopentadienyl)(fluorenyl)methylzirconiummethylbis(pentafluorophenyl)indolylborate diphenylsilanediyl(3-(trimethyl)cyclopentadienyl)(fluorenyl)methylzirconiummethylbis(pentafluorophenyl)indolylborate ethylenebis(indenyl)methylzirconiummethylbis(pentafluorophenyl)indolylborate ethylenebis(2-methylindenyl)methylzirconiummethylbis(pentafluorophenyl)indolylborate ethylenebis(2-methyl-4-phenylindenyl)methylzirconiummethylbis(pentafluorophenyl)indolylborate ethylenebis(2-methyl-4,5-benzindenyl)methylzirconiummethylbis(pentafluorophenyl)indolylborate ethylenbis(2-methyl-4,6-diisopropylindenyl)methylzirconiummethylbis(pentafluorophenyl)indolylborate 1,6-{bis[methylsilylbis(2-methyl-4-phenylindenyl)methylzirconiummethylbis(pentafluorophenyl)indolylborate}hexane 1,6-{bis[methylsilylbis(2-ethyl-4-phenylindenyl)methylzirconiummethylbis(pentafluorophenyl)indolylborate}hexane 1,6-{bis(methylsilylbis(2-methyl-4-naphthylphenylindenyl)methylzirconiummethylbis(pentafluorophenyl)indolylborate}hexane 1,6-{bis[methylsilylbis(2-methyl-4,5-benzoindenyl)methylzirconiummethylbis(pentafluorophenyl)indolylborate}hexane 1,6-{bis[methylsilyl(2-methyl-4-phenylindenyl)(2-methylindenyl)methylzirconiummethylbis(pentafluorophenyl)indolylborate}hexane 1,6-{bis(methylsilylbis(2-methyl-4-phenylindenyl)methylzirconiummethylbis(pentafluorophenyl)indolylborate}ethane 1,6-{bis[methylsilylbis(2-ethyl-4-phenylindenyl)methylzirconiummethylbis(pentafluorophenyl)indolylborate}ethane 1,6-{bis[methylsilylbis(2-methyl-4-naphthylphenylindenyl)methylzirconiummethylbis(pentafluorophenyl)indolylborate}ethane 1,6-{bis[methylsilylbis(2-methyl-4,5-benzoindenyl)methylzirconiummethylbis(pentafluorophenyl)indolylborate}ethane 1,6-{bis[methylsilyl(2-methyl-4-phenylindenyl)(2-methylindenylmethylzirconiummethylbis(pentafluorophenyl)indolylborate}ethane tri(cyclopentadienyl)zirconiummethylbis(pentafluorophenyl)indolylborate tri(methylcyclopentadienyl)zirconiummethylbis(pentafluorophenyl)indolylborate tri(pentamethylcyclopentadienyl)zirconiummethylbis(pentafluorophenyl)indolylborate tri(n-butylcyclopentadienyl)zirconiummethylbis(pentafluorophenyl)indolylborate bis(cyclopentadienyl)zirconium$CH_2CHCHCH_2$bis(pentafluorophenyl)pyrrolylborate bis(methylcyclopentadienyl)zirconium$CH_2CHCHCH_2$bis(pentafluorophenyl)pyrrolylborate bis(pentamethylcyclopentadienyl)

zirconiumCH$_2$CHCHCH$_2$bis(pentafluorophenyl)pyrrolylborate bis(n-butylcyclopentadienyl)zirconiumCH$_2$CHCHCH$_2$bis(pentafluorophenyl)pyrrolylborate bis(indenyl)zirconiumCH$_2$CHCHCH$_2$bis(pentafluorophenyl)pyrrolylborate bis(2-methylindenyl)zirconiumCH$_2$CHCHCH$_2$bis(pentafluorophenyl)pyrrolylborate bis(2-methylbenzindenyl)zirconiumCH$_2$CHCHCH$_2$bis(pentafluorophenyl)pyrrolylborate (tert-butylamido)dimethyl(tetramethyl-$\eta^5$-cyclopentadienyl)silanemethylzirconiummethylbis(pentafluorophenyl)pyrrolylborate dimethylsilanediylbis(indenyl)zirconiumCH$_2$CHCHCH$_2$bis(pentafluorophenyl)pyrrolylborate dimethylsilanediylbis(2-methylindenyl)zirconiumCH$_2$CHCHCH$_2$bis(pentafluorophenyl)pyrrolylborate dimethylsilanediylbis(2-methylbenzindenyl)zirconiumCH$_2$CHCHCH$_2$bis(pentafluorophenyl)pyrrolylborate dimethylsilanediylbis(4-phenylindenyl)zirconiumCH$_2$CHCHCH$_2$bis(pentafluorophenyl)pyrrolylborate dimethylsilanediylbis(4-naphthylindenyl)zirconiumCH$_2$CHCHCH$_2$bis(pentafluorophenyl)pyrrolylborate dimethylsilanediylbis(2-methyl-4-(1-naphthyl)indenyl)zirconiumCH$_2$CHCHCH$_2$bis(pentafluorophenyl)pyrrolylborate dimethylsilanediylbis(2-methyl-4-(2-naphthyl)indenyl)zirconiumCH$_2$CHCHCH$_2$bis(pentafluorophenyl)pyrrolylborate dimethylsilanediylbis(2-methyl-4-phenylindenyl)zirconiumCH$_2$CHCHCH$_2$bis(pentafluorophenyl)pyrrolylborate dimethylsilanediylbis(2-methyl-4-tert-butylindenyl)zirconiumCH$_2$CHCHCH$_2$bis(pentafluorophenyl)pyrrolylborate dimethylsilanediylbis(2-methyl-4-isopropylindenyl)zirconiumCH$_2$CHCHCH$_2$bis(pentafluorophenyl)pyrrolylborate dimethylsilanediylbis(2-methyl-4-(1-naphthyl)indenyl)zirconiumCH$_2$CHCHCH$_2$bis(pentafluorophenyl)pyrrolylborate dimethylsilanediylbis(2-methyl-4-ethylindenyl)zirconiumCH$_2$CHCHCH$_2$bis(pentafluorophenyl)pyrrolylborate dimethylsilanediylbis(2-methyl-4-(acenaphthyl)indenyl)zirconiumCH$_2$CHCHCH$_2$bis(pentafluorophenyl)pyrrolylborate dimethylsilanediylbis(2,4-dimethylindenyl)zirconiumCH$_2$CHCHCH$_2$bis(pentafluorophenyl)pyrrolylborate dimethylsilanediylbis(2-ethylindenyl)zirconiumCH$_2$CHCHCH$_2$bis(pentafluorophenyl)pyrrolylborate dimethylsilanediylbis(2-ethyl-4-ethylindenyl)zirconiumCH$_2$CHCHCH$_2$bis(pentafluorophenyl)pyrrolylborate dimethylsilanediylbis(2-ethyl-4-phenylindenyl)zirconiumCH$_2$CHCHCH$_2$bis(pentafluorophenyl)pyrrolylborate dimethylsilanediylbis(2-methyl-4-(4'-tert-butylphenyl)indenyl)zirconiumCH$_2$CHCHCH$_2$bis(pentafluorophenyl)pyrrolylborate dimethylsilanediylbis(2-methyl-4-(4'-methylphenyl)indenyl)zirconiumCH$_2$CHCHCH$_2$bis(pentafluorophenyl)pyrrolylborate dimethylsilanediylbis(2-methyl-4-(4'-ethylphenyl)indenyl)zirconiumCH$_2$CHCHCH$_2$bis(pentafluorophenyl)pyrrolylborate dimethylsilanediylbis(2-methyl-4-(4'-n-propylphenyl)indenyl)zirconiumCH$_2$CHCHCH$_2$bis(pentafluorophenyl)pyrrolylborate dimethylsilanediylbis(2-methyl-4-(4'-isopropylphenyl)indenyl)zirconiumCH$_2$CHCHCH$_2$bis(pentafluorophenyl)pyrrolylborate dimethylsilanediylbis(2-methyl-4-(4'-n-butylphenyl)indenyl)zirconiumCH$_2$CHCHCH$_2$bis(pentafluorophenyl)pyrrolylborate dimethylsilanediylbis(2-methyl-4-(4'-hexylphenyl)indenyl)zirconiumCH$_2$CHCHCH$_2$bis(pentafluorophenyl)pyrrolylborate dimethylsilanediylbis(2-methyl-4-(4'-sec-butylphenyl)indenyl)zirconiumCH$_2$CHCHCH$_2$bis(pentafluorophenyl)pyrrolylborate dimethylsilanediylbis(2-ethyl-4-(4'-tert-butylphenyl)indenyl)zirconiumCH$_2$CHCHCH$_2$bis(pentafluorophenyl)pyrrolylborate dimethylsilanediylbis(2-ethyl-4-(4'-methylphenyl)indenyl)zirconiumCH$_2$CHCHCH$_2$bis(pentafluorophenyl)pyrrolylborate dimethylsilanediylbis(2-ethyl-4-(4'-ethylphenyl)indenyl)zirconiumCH$_2$CHCHCH$_2$bis(pentafluorophenyl)pyrrolylborate dimethylsilanediylbis(2-ethyl-4-(4'-n-propylphenyl)indenyl)zirconiumCH$_2$CHCHCH$_2$bis(pentafluorophenyl)pyrrolylborate dimethylsilanediylbis(2-ethyl-4-(4'-isopropylphenyl)indenyl)zirconiumCH$_2$CHCHCH$_2$bis(pentafluorophenyl)pyrrolylborate dimethylsilanediylbis(2-ethyl-4-(4'-n-butylphenyl)indenyl)zirconiumCH$_2$CHCHCH$_2$bis(pentafluorophenyl)pyrrolylborate dimethylsilanediylbis(2-ethyl-4-(4'-hexylphenyl)indenyl)zirconiumCH$_2$CHCHCH$_2$bis(pentafluorophenyl)pyrrolylborate dimethylsilanediylbis(2-ethyl-4-(4'-sec-butylphenyl)indenyl)zirconiumCH$_2$CHCHCH$_2$bis(pentafluorophenyl)pyrrolylborate dimethylsilanediylbis(2-n-propyl-4-(4'-tert-butylphenyl)indenyl)zirconiumCH$_2$CHCHCH$_2$bis(pentafluorophenyl)pyrrolylborate dimethylsilanediylbis(2-n-propyl-4-(4'-methylphenyl)indenyl)zirconiumCH$_2$CHCHCH$_2$bis(pentafluorophenyl)pyrrolylborate dimethylsilanediylbis(2-n-propyl-4-(4'-ethylphenyl)indenyl)zirconiumCH$_2$CHCHCH$_2$bis(pentafluorophenyl)pyrrolylborate dimethylsilanediylbis(2-n-propyl-4-(4'-n-propylphenyl)indenyl)zirconiumCH$_2$CHCHCH$_2$bis(pentafluorophenyl)pyrrolylborate dimethylsilanediylbis(2-n-propyl-4-(4'-isopropylphenyl)indenyl)zirconiumCH$_2$CHCHCH$_2$bis(pentafluorophenyl)pyrrolylborate dimethylsilanediylbis(2-n-propyl-4-(4'-n-butylphenyl)indenyl)zirconiumCH$_2$CHCHCH$_2$bis(pentafluorophenyl)pyrrolylborate dimethylsilanediylbis(2-n-propyl-4-(4'-hexylphenyl)indenyl)zirconiumCH$_2$CHCHCH$_2$bis(pentafluorophenyl)pyrrolylborate dimethylsilanediylbis(2-n-propyl-4-(4'-sec-butylphenyl)indenyl)zirconiumCH$_2$CHCHCH$_2$bis(pentafluorophenyl)pyrrolylborate dimethylsilanediylbis(2-n-butyl-4-(4'-tert-butylphenyl)indenyl)zirconiumCH$_2$CHCHCH$_2$bis(pentafluorophenyl)pyrrolylborate dimethylsilanediylbis(2-n-butyl-4-(4'-methylphenyl)indenyl)zirconiumCH$_2$CHCHCH$_2$bis(pentafluorophenyl)pyrrolylborate dimethylsilanediylbis(2-n-butyl-4-(4'-ethylphenyl)indenyl)zirconiumCH$_2$CHCHCH$_2$bis (pentafluorophenyl)pyrrolylborate dimethylsilanediylbis(2-n-butyl-4-(4'-n-propylphenyl)indenyl)zirconiumCH$_2$CHCHCH$_2$bis(pentafluorophenyl)pyrrolylborate dimethylsilanediylbis(2-n-butyl-4-(4'-isopropylphenyl)indenyl)zirconiumCH$_2$CHCHCH$_2$bis(pentafluorophenyl)pyrrolylborate dimethylsilanediylbis(2-n-butyl-4-(4'-n-butylphenyl)indenyl)zirconiumCH$_2$CHCHCH$_2$bis(pentafluorophenyl)pyrrolylborate dimethylsilanediylbis(2-n-butyl-4-(4'-hexylphenyl)indenyl)zirconiumCH$_2$CHCHCH$_2$bis(pentafluorophenyl)pyrrolylborate dimethylsilanediylbis(2-n-butyl-4-(4'-sec-butylphenyl)indenyl)zirconiumCH$_2$CHCHCH$_2$bis(pentafluorophenyl)pyrrolylborate dimethylsilanediylbis(2-n-hexyl-4-(4'-tert-butylphenyl)indenyl)zirconiumCH$_2$CHCHCH$_2$bis(pentafluorophenyl)pyrrolylborate dimethylsilanediylbis(2-n-hexyl-4-(4'-methylphenyl)indenyl)zirconiumCH$_2$CHCHCH$_2$bis(pentafluorophenyl)pyrrolylborate dimethylsilanediylbis(2-n-hexyl-4-(4'-ethylphenyl)indenyl)zirconiumCH$_2$CHCHCH$_2$bis(pentafluorophenyl)pyrrolylborate dimethylsilanediylbis(2-n-hexyl-4-(4'-n-propylphenyl)indenyl)zirconiumCH$_2$CHCHCH$_2$bis(pentafluorophenyl)pyrrolylborate dimethylsilanediylbis(2-n-hexyl-4-(4'-isopropylphenyl)indenyl)zirconiumCH$_2$CHCHCH$_2$bis(pentafluorophenyl)pyrrolylborate dimethylsilanediylbis(2-n-hexyl-4-(4'-n-butylphenyl)indenyl)zirconiumCH$_2$CHCHCH$_2$bis(pentafluorophenyl)pyrrolylborate dimethylsilanediylbis(2-n-hexyl-4-(4'-hexylphenyl)indenyl)zirconiumCH$_2$CHCHCH$_2$bis(pentafluorophenyl)pyrrolylborate dimethylsilanediylbis(2-n-hexyl-4-(4'-sec-butylphenyl)indenyl)zirconiumCH$_2$CHCHCH$_2$bis(pentafluorophenyl)pyrrolylborate dimethylsilanediylbis(2-methyl-4,5-benzoindenyl)zirconiumCH$_2$CHCHCH$_2$bis(pentafluorophenyl)pyrrolylborate dimethylsilanediylbis(2-methyl-4,6-diisopropylindenyl)zirconiumCH$_2$CHCHCH$_2$bis(pentafluorophenyl)pyrrolylborate dimethylsilanediylbis(2,4,6-trimethylindenyl)zirconiumCH$_2$CHCHCH$_2$bis(pentafluorophenyl)pyrrolylborate dimethylsilanediylbis(2,5,6-trimethylindenyl)zirconiumCH$_2$CHCHCH$_2$bis(pentafluorophenyl)pyrrolylborate dimethylsilanediylbis(2,4,7-trimethylindenyl)zirconiumCH$_2$CHCHCH$_2$bis(pentafluorophenyl)pyrrolylborate dimethylsilanediylbis(2-methyl-5-isobutylindenyl)zirconiumCH$_2$CHCHCH$_2$bis(pentafluorophenyl)pyrrolylborate dimethylsilanediylbis(2-methyl-5-tert-butylindenyl)zirconiumCH$_2$CHCHCH$_2$bis(pentafluorophenyl)pyrrolylborate methyl(phenyl)silanediylbis(indenyl)zirconiumCH$_2$CHCHCH$_2$bis(pentafluorophenyl)pyrrolylborate methyl(phenyl)silanediylbis(2-methylindenyl)zirconiumCH$_2$CHCHCH$_2$bis(pentafluorophenyl)pyrrolylborate methyl(phenyl)silanediylbis(2-methylbenzindenyl)zirconiumCH$_2$CHCHCH$_2$bis(pentafluorophenyl)pyrrolylborate methyl(phenyl)silanediylbis(4-phenylindenyl)zirconiumCH$_2$CHCHCH$_2$bis(pentafluorophenyl)pyrrolylborate methyl(phenyl)silanediylbis(4-naphthylindenyl)zirconiumCH$_2$CHCHCH$_2$bis(pentafluorophenyl)pyrrolylborate methyl(phenyl)silanediylbis(2-methyl-4-(1-naphthyl)indenyl)zirconiumCH$_2$CHCHCH$_2$bis(pentafluorophenyl)pyrrolylborate methyl(phenyl)silanediylbis(2-methyl-4-(2-naphthyl)indenyl)zirconiumCH$_2$CHCHCH$_2$bis(pentafluorophenyl)pyrrolylborate methyl(phenyl)silanediylbis(2-methyl-4-phenylindenyl)zirconiumCH$_2$CHCHCH$_2$bis(pentafluorophenyl)pyrrolylborate methyl(phenyl)silanediylbis(2-methyl-4-tert-butylindenyl)zirconiumCH$_2$CHCHCH$_2$bis(pentafluorophenyl)pyrrolylborate methyl(phenyl)silanediylbis(2-methyl-4-isopropylindenyl)zirconiumCH$_2$CHCHCH$_2$bis(pentafluorophenyl)pyrrolylborate methyl(phenyl)silanediylbis(2-methyl-4-(1-naphthyl)indenyl)zirconiumCH$_2$CHCHCH$_2$bis(pentafluorophenyl)pyrrolylborate methyl(phenyl)silanediylbis(2-methyl-4-ethylindenyl)zirconiumCH$_2$CHCHCH$_2$bis(pentafluorophenyl)pyrrolylborate methyl(phenyl)silanediylbis(2-methyl-4-(acenaphthyl)indenyl)zirconiumCH$_2$CHCHCH$_2$bis(pentafluorophenyl)pyrrolylborate methyl(phenyl)silanediylbis(2,4-dimethylindenyl)zirconiumCH$_2$CHCHCH$_2$bis(pentafluorophenyl)pyrrolylborate methyl(phenyl)silanediylbis(2-ethylindenyl)zirconiumCH$_2$CHCHCH$_2$bis(pentafluorophenyl)pyrrolylborate methyl(phenyl)silanediylbis(2-ethyl-4-ethylindenyl)zirconiumCH$_2$CHCHCH$_2$bis(pentafluorophenyl)pyrrolylborate methyl(phenyl)silanediylbis(2-ethyl-4-phenylindenyl)zirconiumCH$_2$CHCHCH$_2$bis(pentafluorophenyl)pyrrolylborate methyl(phenyl)silanediylbis(2-methyl-4,5-benzoindenyl)zirconiumCH$_2$CHCHCH$_2$bis(pentafluorophenyl)pyrrolylborate methyl(phenyl)silanediylbis(2-methyl-4,6-diisopropylindenyl)zirconiumCH$_2$CHCHCH$_2$bis(pentafluorophenyl)pyrrolylborate methyl(phenyl)silanediylbis(2,4,6-trimethylindenyl)zirconiumCH$_2$CHCHCH$_2$bis(pentafluorophenyl)pyrrolylborate methyl(phenyl)silanediylbis(2,5,6-trimethylindenyl)zirconiumCH$_2$CHCHCH$_2$bis(pentafluorophenyl)pyrrolylborate methyl(phenyl)silanediylbis(2,4,7-trimethylindenyl)zirconiumCH$_2$CHCHCH$_2$bis(pentafluorophenyl)pyrrolylborate methyl(phenyl)silanediylbis(2-methyl-5-isobutylindenyl)zirconiumCH$_2$CHCHCH$_2$bis(pentafluorophenyl)pyrrolylborate methyl(phenyl)silanediylbis(2-methyl-5-tert-butylindenyl)zirconiumCH$_2$CHCHCH$_2$bis(pentafluorophenyl)pyrrolylborate diphenylmethylene(fluorenyl)(cyclopentadienyl)zirconiumCH$_2$CHCHCH$_2$bis(pentafluorophenyl)pyrrolylborate dimethylmethylene(fluorenyl)(cyclopentadienyl)zirconiumCH$_2$CHCHCH$_2$bis(pentafluorophenyl)pyrrolylborate methylphenylmethylene(fluorenyl)(cyclopentadienyl)zirconiumCH$_2$CHCHCH$_2$bis(pentafluorophenyl)pyrrolylborate dimethylsilanediyl(3-tert-butylcyclopentadienyl)(fluorenyl)zirconiumCH$_2$CHCHCH$_2$bis(pentafluorophenyl)pyrrolylborate diphenylsilanediyl(3-(trimethyl)cyclopentadienyl)(fluorenyl)zirconiumCH$_2$CHCHCH$_2$bis(pentafluorophenyl)pyrrolylborate ethylenebis(indenyl)zirconiumCH$_2$CHCHCH$_2$bis(pentafluorophenyl)pyrrolylborate ethylenebis(2-methylindenyl)zirconiumCH$_2$CHCHCH$_2$bis(pentafluorophenyl)

pyrrolylborate ethylenebis(2-methyl-4-phenylindenyl)zirconiumCH$_2$CHCHCH$_2$bis(pentafluorophenyl)pyrrolylborate ethylenebis(2-methyl-4,5-benzindenyl)zirconiumCH$_2$CHCHCH$_2$bis(pentafluorophenyl)pyrrolylborate ethylenebis(2-methyl-4,6-diisopropylindenyl)zirconiumCH$_2$CHCHCH$_2$bis(pentafluorophenyl)pyrrolylborate 1,6-{bis[methylsilylbis(2-methyl-4-phenylindenyl)zirconiumCH$_2$CHCHCH$_2$bis(pentafluorophenyl)pyrrolylborate}hexane 1,6-{bis[methylsilylbis(2-ethyl-4-phenylindenyl)zirconiumCH$_2$CHCHCH$_2$bis(pentafluorophenyl)pyrrolylborate}hexane 1,6-{bis[methylsilylbis(2-methyl-4-naphthylphenylindenyl)zirconiumCH$_2$CHCHCH$_2$bis(pentafluorophenyl)pyrrolylborate}hexane 1,6-{bis[methylsilylbis(2-methyl-4,5-benzoindenyl)zirconiumCH$_2$CHCHCH$_2$bis(pentafluorophenyl)pyrrolylborate}hexane 1,6-{bis[methylsilyl(2-methyl-4-phenylindenyl)(2-methylindenyl)zirconiumCH$_2$CHCHCH$_2$bis(pentafluorophenyl)pyrrolylborate}hexane 1,6-{bis[methylsilylbis(2-methyl-4-phenylindenyl)zirconiumCH$_2$CHCHCH$_2$bis(pentafluorophenyl)pyrrolylborate}ethane 1,6-{bis[methylsilylbis(2-ethyl-4-phenylindenyl)zirconiumCH$_2$CHCHCH$_2$bis(pentafluorophenyl)pyrrolylborate}ethane 1,6-{bis[methylsilylbis(2-methyl-4-naphthylphenylindenyl)zirconiumCH$_2$CHCHCH$_2$bis(pentafluorophenyl)pyrrolylborate}ethane 1,6-{bis[methylsilylbis(2-methyl-4,5-benzoindenyl)zirconiumCH$_2$CHCHCH$_2$bis(pentafluorophenyl)pyrrolylborate}ethane 1,6-{bis[methylsilyl(2-methyl-4-phenylindenyl)(2-methylindenylzirconiumCH$_2$CHCHCH$_2$bis(pentafluorophenyl)pyrrolylborate}ethane tri(cyclopentadienyl)zirconiummethylbis(pentafluorophenyl)pyrrolylborate tri(methylcyclopentadienyl)zirconiummethylbis(pentafluorophenyl)pyrrolylborate tri(pentamethylcyclopentadienyl)zirconiummethylbis(pentafluorophenyl)pyrrolylborate tri(n-butylcyclopentadienyl)zirconiummethylbis(pentafluorophenyl)pyrrolylborate bis(cyclopentadienyl)zirconiumCH$_2$CHCHCH$_2$bis(pentafluorophenyl)imidazolylborate bis(methylcyclopentadienyl)zirconiumCH$_2$CHCHCH$_2$bis(pentafluorophenyl)imidazolylborate bis(pentamethylcyclopentadienyl)zirconiumCH$_2$CHCHCH$_2$bis(pentafluorophenyl)imidazolylborate bis(n-butylcyclopentadienyl)zirconiumCH$_2$CHCHCH$_2$bis(pentafluorophenyl)imidazolylborate bis(indenyl)zirconiumCH$_2$CHCHCH$_2$bis(pentafluorophenyl)imidazolylborate bis(2-methylindenyl)zirconiumCH$_2$CHCHCH$_2$bis(pentafluorophenyl)imidazolylborate bis(2-methylbenzindenyl)zirconiumCH$_2$CHCHCH$_2$bis(pentafluorophenyl)imidazolylborate (tert-butylamido)dimethyl(tetramethyl-η$^5$-cyclopentadienyl)silanemethylzirconiummethylbis(pentafluorophenyl)imidazolylborate dimethylsilanediylbis(indenyl)zirconiumCH$_2$CHCHCH$_2$bis(pentafluorophenyl)imidazolylborate dimethylsilanediylbis(2-methylindenyl)zirconiumCH$_2$CHCHCH$_2$bis(pentafluorophenyl)imidazolylborate dimethylsilanediylbis(2-methylbenzindenyl)zirconiumCH$_2$CHCHCH$_2$bis(pentafluorophenyl)imidazolylborate dimethylsilanediylbis(4-phenylindenyl)zirconiumCH$_2$CHCHCH$_2$bis(pentafluorophenyl)imidazolylborate dimethylsilanediylbis(4-naphthylindenyl)zirconiumCH$_2$CHCHCH$_2$bis(pentafluorophenyl)imidazolylborate dimethylsilanediylbis(2-methyl-4-(1-naphthyl)indenyl)zirconiumCH$_2$CHCHCH$_2$bis(pentafluorophenyl)imidazolylborate dimethylsilanediylbis(2-methyl-4-(2-naphthyl)indenyl)zirconiumCH$_2$CHCHCH$_2$bis(pentafluorophenyl)imidazolylborate dimethylsilanediylbis(2-methyl-4-phenylindenyl)zirconiumCH$_2$CHCHCH$_2$bis(pentafluorophenyl)imidazolylborate dimethylsilanediylbis(2-methyl-4-tert-butylindenyl)zirconiumCH$_2$CHCHCH$_2$bis(pentafluorophenyl)imidazolylborate dimethylsilanediylbis(2-methyl-4-isopropylindenyl)zirconiumCH$_2$CHCHCH$_2$bis(pentafluorophenyl)imidazolylborate dimethylsilanediylbis(2-methyl-4-(1-naphthyl)indenyl)zirconiumCH$_2$CHCHCH$_2$bis(pentafluorophenyl)imidazolylborate dimethylsilanediylbis(2-methyl-4-ethylindenyl)zirconiumCH$_2$CHCHCH$_2$bis(pentafluorophenyl)imidazolylborate dimethylsilanediylbis(2-methyl-4-(acenaphthyl)indenyl)zirconiumCH$_2$CHCHCH$_2$bis(pentafluorophenyl)imidazolylborate dimethylsilanediylbis(2,4-dimethylindenyl)zirconiumCH$_2$CHCHCH$_2$bis(pentafluorophenyl)imidazolylborate dimethylsilanediylbis(2-ethylindenyl)zirconiumCH$_2$CHCHCH$_2$bis(pentafluorophenyl)imidazolylborate dimethylsilanediylbis(2-ethyl-4-ethylindenyl)zirconiumCH$_2$CHCHCH$_2$bis(pentafluorophenyl)imidazolylborate dimethylsilanediylbis(2-ethyl-4-phenylindenyl)zirconiumCH$_2$CHCHCH$_2$bis(pentafluorophenyl)imidazolylborate dimethylsilanediylbis(2-methyl-4-(4'-tert-butylphenyl)indenyl)zirconiumCH$_2$CHCHCH$_2$bis(pentafluorophenyl)imidazolylborate dimethylsilanediylbis(2-methyl-4-(4'-methylphenyl)indenyl)zirconiumCH$_2$CHCHCH$_2$bis(pentafluorophenyl)imidazolylborate dimethylsilanediylbis(2-methyl-4-(4'-ethylphenyl)indenyl)zirconiumCH$_2$CHCHCH$_2$bis(pentafluorophenyl)imidazolylborate dimethylsilanediylbis(2-methyl-4-(4'-n-propylphenyl)indenyl)zirconiumCH$_2$CHCHCH$_2$bis(pentafluorophenyl)imidazolylborate dimethylsilanediylbis(2-methyl-4-(4'-isopropylphenyl)indenyl)zirconiumCH$_2$CHCHCH$_2$bis(pentafluorophenyl)imidazolylborate dimethylsilanediylbis(2-methyl-4-(4'-n-butylphenyl)indenyl)zirconiumCH$_2$CHCHCH$_2$bis(pentafluorophenyl)imidazolylborate dimethylsilanediylbis(2-methyl-4-(4'-hexylphenyl)indenyl)zirconiumCH$_2$CHCHCH$_2$bis(pentafluorophenyl)imidazolylborate dimethylsilanediylbis(2-methyl-4-(4'-sec-butylphenyl)indenyl)zirconiumCH$_2$CHCHCH$_2$bis(pentafluorophenyl)imidazolylborate dimethylsilanediylbis(2-ethyl-4-(4'-tert-butylphenyl)indenyl)zirconiumCH$_2$CHCHCH$_2$bis(pentafluorophenyl)imidazolylborate dimethylsilanediylbis(2-ethyl-4-(4'-methylphenyl)indenyl)zirconiumCH$_2$CHCHCH$_2$bis(pentafluorophenyl)imidazolylborate dimethylsilanediylbis(2-ethyl-4-(4'-ethylphenyl)indenyl)zirconiumCH$_2$CHCHCH$_2$bis(pentafluorophenyl)imidazolylborate dimethylsilanediylbis(2-ethyl-4-(4'-n-propylphenyl)indenyl)zirconiumCH$_2$CHCHCH$_2$bis(pentafluorophenyl)imidazolylborate
dimethylsilanediylbis(2-ethyl-4-(4'-isopropylphenyl)indenyl)zirconiumCH$_2$CHCHCH$_2$bis(pentafluorophenyl)imidazolylborate
dimethylsilanediylbis(2-ethyl-4-(4'-n-butylphenyl)indenyl)zirconiumCH$_2$CHCHCH$_2$bis(pentafluorophenyl)imidazolylborate
dimethylsilanediylbis(2-ethyl-4-(4'-hexylphenyl)indenyl)zirconiumCH$_2$CHCHCH$_2$bis(pentafluorophenyl)imidazolylborate
dimethylsilanediylbis(2-ethyl-4-(4'-sec-butylphenyl)indenyl)zirconiumCH$_2$CHCHCH$_2$bis(pentafluorophenyl)imidazolylborate
dimethylsilanediylbis(2-n-propyl-4-(4'-tert-butylphenyl)indenyl)zirconiumCH$_2$CHCHCH$_2$bis(pentafluorophenyl)imidazolylborate
dimethylsilanediylbis(2-n-propyl-4-(4'-methylphenyl)indenyl)zirconiumCH$_2$CHCHCH$_2$bis(pentafluorophenyl)imidazolylborate
dimethylsilanediylbis(2-n-propyl-4-(4'-ethylphenyl)indenyl)zirconiumCH$_2$CHCHCH$_2$bis(pentafluorophenyl)imidazolylborate
dimethylsilanediylbis(2-n-propyl-4-(4'-n-propylphenyl)indenyl)zirconiumCH$_2$CHCHCH$_2$bis(pentafluorophenyl)imidazolylborate
dimethylsilanediylbis(2-n-propyl-4-(4'-isopropylphenyl)indenyl)zirconiumCH$_2$CHCHCH$_2$bis(pentafluorophenyl)imidazolylborate
dimethylsilanediylbis(2-n-propyl-4-(4'-n-butylphenyl)indenyl)zirconiumCH$_2$CHCHCH$_2$bis(pentafluorophenyl)imidazolylborate
dimethylsilanediylbis(2-n-propyl-4-(4'-hexylphenyl)indenyl)zirconiumCH$_2$CHCHCH$_2$bis(pentafluorophenyl)imidazolylborate
dimethylsilanediylbis(2-n-propyl-4-(4'-sec-butylphenyl)indenyl)zirconiumCH$_2$CHCHCH$_2$bis(pentafluorophenyl)imidazolylborate
dimethylsilanediylbis(2-n-butyl-4-(4'-tert-butylphenyl)indenyl)zirconiumCH$_2$CHCHCH$_2$bis(pentafluorophenyl)imidazolylborate
dimethylsilanediylbis(2-n-butyl-4-(4'-methylphenyl)indenyl)zirconiumCH$_2$CHCHCH$_2$bis(pentafluorophenyl)imidazolylborate
dimethylsilanediylbis(2-n-butyl-4-(4'-ethylphenyl)indenyl)zirconiumCH$_2$CHCHCH$_2$bis(pentafluorophenyl)imidazolylborate
dimethylsilanediylbis(2-n-butyl-4-(4'-n-propylphenyl)indenyl)zirconiumCH$_2$CHCHCH$_2$bis(pentafluorophenyl)imidazolylborate
dimethylsilanediylbis(2-n-butyl-4-(4'-isopropylphenyl)indenyl)zirconiumCH$_2$CHCHCH$_2$bis(pentafluorophenyl)imidazolylborate
dimethylsilanediylbis(2-n-butyl-4-(4'-n-butylphenyl)indenyl)zirconiumCH$_2$CHCHCH$_2$bis(pentafluorophenyl)imidazolylborate
dimethylsilanediylbis(2-n-butyl-4-(4'-hexylphenyl)indenyl)zirconiumCH$_2$CHCHCH$_2$bis(pentafluorophenyl)imidazolylborate
dimethylsilanediylbis(2-n-butyl-4-(4'-sec-butylphenyl)indenyl)zirconiumCH$_2$CHCHCH$_2$bis(pentafluorophenyl)imidazolylborate
dimethylsilanediylbis(2-n-hexyl-4-(4'-tert-butylphenyl)indenyl)zirconiumCH$_2$CHCHCH$_2$bis(pentafluorophenyl)imidazolylborate
dimethylsilanediylbis(2-n-hexyl-4-(4'-methylphenyl)indenyl)zirconiumCH$_2$CHCHCH$_2$bis(pentafluorophenyl)imidazolylborate
dimethylsilanediylbis(2-n-hexyl-4-(4'-ethylphenyl)indenyl)zirconiumCH$_2$CHCHCH$_2$bis(pentafluorophenyl)imidazolylborate
dimethylsilanediylbis(2-n-hexyl-4-(4'-n-propylphenyl)indenyl)zirconiumCH$_2$CHCHCH$_2$bis(pentafluorophenyl)imidazolylborate
dimethylsilanediylbis(2-n-hexyl-4-(4'-isopropylphenyl)indenyl)zirconiumCH$_2$CHCHCH$_2$bis(pentafluorophenyl)imidazolylborate
dimethylsilanediylbis(2-n-hexyl-4-(4'-n-butylphenyl)indenyl)zirconiumCH$_2$CHCHCH$_2$bis(pentafluorophenyl)imidazolylborate
dimethylsilanediylbis(2-n-hexyl-4-(4'-hexylphenyl)indenyl)zirconiumCH$_2$CHCHCH$_2$bis(pentafluorophenyl)imidazolylborate
dimethylsilanediylbis(2-n-hexyl-4-(4'-sec-butylphenyl)indenyl)zirconiumCH$_2$CHCHCH$_2$bis(pentafluorophenyl)imidazolylborate
dimethylsilanediylbis(2-methyl-4,5-benzoindenyl)zirconiumCH$_2$CHCHCH$_2$bis(pentafluorophenyl)imidazolylborate
dimethylsilanediylbis(2-methyl-4,6-diisopropylindenyl)zirconiumCH$_2$CHCHCH$_2$bis(pentafluorophenyl)imidazolylborate
dimethylsilanediylbis(2,4,6-trimethylindenyl)zirconiumCH$_2$CHCHCH$_2$bis(pentafluorophenyl)imidazolylborate
dimethylsilanediylbis(2,5,6-trimethylindenyl)zirconiumCH$_2$CHCHCH$_2$bis(pentafluorophenyl)imidazolylborate
dimethylsilanediylbis(2,4,7-trimethylindenyl)zirconiumCH$_2$CHCHCH$_2$bis(pentafluorophenyl)imidazolylborate
dimethylsilanediylbis(2-methyl-5-isobutylindenyl)zirconiumCH$_2$CHCHCH$_2$bis(pentafluorophenyl)imidazolylborate
dimethylsilanediylbis(2-methyl-5-tert-butylindenyl)zirconiumCH$_2$CHCHCH$_2$bis(pentafluorophenyl)imidazolylborate
methyl(phenyl)silanediylbis(indenyl)zirconiumCH$_2$CHCHCH$_2$bis(pentafluorophenyl)imidazolylborate
methyl(phenyl)silanediylbis(2-methylindenyl)zirconiumCH$_2$CHCHCH$_2$bis(pentafluorophenyl)imidazolylborate
methyl(phenyl)silanediylbis(2-methylbenzindenyl)zirconiumCH$_2$CHCHCH$_2$bis(pentafluorophenyl)imidazolylborate
methyl(phenyl)silanediylbis(4-phenylindenyl)zirconiumCH$_2$CHCHCH$_2$bis(pentafluorophenyl)imidazolylborate
methyl(phenyl)silanediylbis(4-naphthylindenyl)zirconiumCH$_2$CHCHCH$_2$bis(pentafluorophenyl)imidazolylborate
methyl(phenyl)silanediylbis(2-methyl-4-(1-naphthyl)indenyl)zirconiumCH$_2$CHCHCH$_2$bis(pentafluorophenyl)imidazolylborate
methyl(phenyl)silanediylbis(2-methyl-4-(2-naphthyl)indenyl)zirconiumCH$_2$CHCHCH$_2$bis(pentafluorophenyl)imidazolylborate
methyl(phenyl)silanediylbis(2-methyl-4-phenylindenyl)zirconiumCH$_2$CHCHCH$_2$bis(pentafluorophenyl)imidazolylborate
methyl(phenyl)silanediylbis(2-methyl-4-tert-butylindenyl)zirconiumCH$_2$CHCHCH$_2$bis(pentafluorophenyl)imidazolylborate
methyl(phenyl)silanediylbis(2-methyl-4-isopropylindenyl)zirconiumCH$_2$CHCHCH$_2$bis(pentafluorophenyl)imidazolylborate
methyl(phenyl)silanediylbis(2-methyl-4-(1-naphthyl)indenyl)zirconiumCH$_2$CHCHCH$_2$bis(pentafluorophenyl)imidazolylborate
methyl(phenyl)silanediylbis(2- methyl-4-ethylindenyl)zirconiumCH$_2$CHCHCH$_2$bis(pentafluorophenyl)imidazolylborate methyl(phenyl)silanediylbis(2-methyl-4-(acenaphthyl)indenyl)zirconiumCH$_2$CHCHCH$_2$bis(pentafluorophenyl)imidazolylborate methyl(phenyl)silanediylbis(2,4-dimethylindenyl)zirconiumCH$_2$CHCHCH$_2$bis(pentafluorophenyl)imidazolylborate methyl(phenyl)silanediylbis(2-ethylindenyl)zirconiumCH$_2$CHCHCH$_2$bis(pentafluorophenyl)imidazolylborate methyl(phenyl)silanediylbis(2-ethyl-4-ethylindenyl)zirconiumCH$_2$CHCHCH$_2$bis(pentafluorophenyl)imidazolylborate methyl(phenyl)silanediylbis(2-ethyl-4-phenylindenyl)zirconiumCH$_2$CHCHCH$_2$bis(pentafluorophenyl)imidazolylborate methyl(phenyl)silanediylbis(2-methyl-4,5-benzoindenyl)zirconiumCH$_2$CHCHCH$_2$bis(pentafluorophenyl)imidazolylborate methyl(phenyl)silanediylbis(2-methyl-4,6-diisopropylindenyl)zirconiumCH$_2$CHCHCH$_2$bis(pentafluorophenyl)imidazolylborate methyl(phenyl)silanediylbis(2,4,6-trimethylindenyl)zirconiumCH$_2$CHCHCH$_2$bis(pentafluorophenyl)imidazolylborate methyl(phenyl)silanediylbis(2,5,6-trimethylindenyl)zirconiumCH$_2$CHCHCH$_2$bis(pentafluorophenyl)imidazolylborate methyl(phenyl)silanediylbis(2,4,7-trimethylindenyl)zirconiumCH$_2$CHCHCH$_2$bis(pentafluorophenyl)imidazolylborate methyl(phenyl)silanediylbis(2-methyl-5-isobutylindenyl)zirconiumCH$_2$CHCHCH$_2$bis(pentafluorophenyl)imidazolylborate methyl(phenyl)silanediylbis(2-methyl-5-tert-butylindenyl)zirconiumCH$_2$CHCHCH$_2$bis(pentafluorophenyl)imidazolylborate diphenylmethylene(fluorenyl)(cyclopentadienyl)zirconiumCH$_2$CHCHCH$_2$bis(pentafluorophenyl)imidazolylborate dimethylmethylene(fluorenyl)(cyclopentadienyl)zirconiumCH$_2$CHCHCH$_2$bis(pentafluorophenyl)imidazolylborate methylphenylmethylene(fluorenyl)(cyclopentadienyl)zirconiumCH$_2$CHCHCH$_2$bis(pentafluorophenyl)imidazolylborate dimethylsilanediyl(3-tert-butylcyclopentadienyl)(fluorenyl)zirconiumCH$_2$CHCHCH$_2$bis(pentafluorophenyl)imidazolylborate diphenylsilanediyl(3-(trimethyl)cyclopentadienyl)(fluorenyl)zirconiumCH$_2$CHCHCH$_2$bis(pentafluorophenyl)imidazolylborate ethylenebis(indenyl)zirconiumCH$_2$CHCHCH$_2$bis(pentafluorophenyl)imidazolylborate ethylenebis(2-methylindenyl)zirconiumCH$_2$CHCHCH$_2$bis(pentafluorophenyl)imidazolylborate ethylenebis(2-methyl-4-phenylindenyl)zirconiumCH$_2$CHCHCH$_2$bis(pentafluorophenyl)imidazolylborate ethylenebis(2-methyl-4,5-benzindenyl)zirconiumCH$_2$CHCHCH$_2$bis(pentafluorophenyl)imidazolylborate ethylenebis(2-methyl-4,6-diisopropylindenyl)zirconiumCH$_2$CHCHCH$_2$bis(pentafluorophenyl)imidazolylborate 1,6-{bis[methylsilylbis(2-methyl-4-phenylindenyl)zirconiumCH$_2$CHCHCH$_2$bis(pentafluorophenyl)imidazolylborate}hexane 1,6-{bis[methylsilylbis(2-ethyl-4-phenylindenyl)zirconiumCH$_2$CHCHCH$_2$bis(pentafluorophenyl)imidazolylborate}hexane 1,6-{bis[methylsilylbis(2-methyl-4-naphthylphenylindenyl)zirconiumCH$_2$CHCHCH$_2$bis(pentafluorophenyl)imidazolylborate}hexane 1,6-{bis methylsilylbis(2-methyl-4,5-benzoindenyl)zirconiumCH$_2$CHCHCH$_2$bis(pentafluorophenyl)imidazolylborate}hexane 1,6-{bis[methylsilyl(2-methyl-4-phenylindenyl)(2-methylindenylzirconiumCH$_2$CHCHCH$_2$bis(pentafluorophenyl)imidazolylborate}hexane 1,6-{bis methylsilylbis(2-methyl-4-phenylindenyl)zirconiumCH$_2$CHCHCH$_2$bis(pentafluorophenyl)imidazolylborate}ethane 1,6-{bis(methylsilylbis(2-ethyl-4-phenylindenyl)zirconiumCH$_2$CHCHCH$_2$bis(pentafluorophenyl)imidazolylborate}ethane 1,6-{bis[methylsilylbis(2-methyl-4-naphthylphenylindenyl)zirconiumCH$_2$CHCHCH$_2$bis(pentafluorophenyl)imidazolylborate}ethane 1,6-{bis(methylsilyl-bis(2-methyl-4,5-benzoindenyl)zirconiumCH$_2$CHCHCH$_2$bis(pentafluorophenyl)imidazolylborate}ethane 1,6-{bis[methylsilyl(2-methyl-4-phenylindenyl)(2-methylindenyl)zirconiumCH$_2$CHCHCH$_2$bis(pentafluorophenyl)imidazolylborate}ethane tri(cyclopentadienyl)zirconiummethylbis(pentafluorophenyl)imidazolylborate tri(methylcyclopentadienyl)zirconiummethylbis(pentafluorophenyl)imidazolylborate tri(pentamethylcyclopentadienyl)zirconiummethylbis(pentafluorophenyl)imidazolylborate tri(n-butylcyclopentadienyl)zirconiummethylbis(pentafluorophenyl)imidazolylborate bis(cyclopentadienyl)zirconiumCH$_2$CHCHCH$_2$bis(pentafluorophenyl)isoindolylborate bis(methylcyclopentadienyl)zirconiumCH$_2$CHCHCH$_2$bis(pentafluorophenyl)isoindolylborate bis(pentamethylcyclopentadienyl)zirconiumCH$_2$CHCHCH$_2$bis(pentafluorophenyl)isoindolylborate bis(n-butylcyclopentadienyl)zirconiumCH$_2$CHCHCH$_2$bis(pentafluorophenyl)isoindolylborate bis(indenyl)zirconiumCH$_2$CHCHCH$_2$bis(pentafluorophenyl)isoindolylborate bis(2-methylindenyl)zirconiumCH$_2$CHCHCH$_2$bis(pentafluorophenyl)isoindolylborate bis(2-methylbenzindenyl)zirconiumCH$_2$CHCHCH$_2$bis(pentafluorophenyl)isoindolylborate (tert-butylamido)dimethyl(tetramethyl-$\eta^5$-cyclopentadienyl)silanemethylzirconiummethylbis(pentafluorophenyl)isoindolylborate dimethylsilanediylbis(indenyl)zirconiumCH$_2$CHCHCH$_2$bis(pentafluorophenyl)isoindolylborate dimethylsilanediylbis(2-methylindenyl)zirconiumCH$_2$CHCHCH$_2$bis(pentafluorophenyl)isoindolylborate dimethylsilanediylbis(2-methylbenzindenyl)zirconiumCH$_2$CHCHCH$_2$bis(pentafluorophenyl)isoindolylborate dimethylsilanediylbis(4-phenylindenyl)zirconiumCH$_2$CHCHCH$_2$bis(pentafluorophenyl)isoindolylborate dimethylsilanediylbis(4-naphthylindenyl)zirconiumCH$_2$CHCHCH$_2$bis(pentafluorophenyl)isoindolylborate dimethylsilanediylbis(2-methyl-4-(1-naphthyl)indenyl)zirconiumCH$_2$CHCHCH$_2$bis(pentafluorophenyl)isoindolylborate dimethylsilanediylbis(2-methyl-4-(2-naphthyl)indenyl)zirconiumCH$_2$CHCHCH$_2$bis(pentafluorophenyl)isoindolylborate dimethylsilanediylbis(2-methyl-4-phenylindenyl)zirconiumCH$_2$CHCHCH$_2$bis(pentafluorophenyl)isoindolylborate dimethylsilanediylbis(2-methyl-4-tert-butylindenyl)zirconiumCH$_2$CHCHCH$_2$bis(pentafluorophenyl)isoindolylborate dimethylsilanediylbis(2-methyl-4-isopropylindenyl)zirconiumCH$_2$CHCHCH$_2$bis(pentafluorophenyl)isoindolylborate dimethylsilanediylbis(2-methyl-4-(1- naphthyl)indenyl)zirconiumCH$_2$CHCHCH$_2$bis (pentafluorophenyl)isoindolylborate dimethylsilanediylbis(2-methyl-4-ethylindenyl) zirconiumCH$_2$CHCHCH$_2$bis(pentafluorophenyl) isoindolylborate dimethylsilanediylbis(2-methyl-4-(acenaphthyl)indenyl)zirconiumCH$_2$CHCHCH$_2$bis (pentafluorophenyl)isoindolylborate dimethylsilanediylbis(2,4-dimethylindenyl) zirconiumCH$_2$CHCHCH$_2$bis(pentafluorophenyl) isoindolylborate dimethylsilanediylbis(2-ethylindenyl) zirconiumCH$_2$CHCHCH$_2$bis(pentafluorophenyl) isoindolylborate dimethylsilanediylbis(2-ethyl-4-ethylindenyl)zirconiumCH$_2$CHCHCH$_2$bis (pentafluorophenyl)isoindolylborate dimethylsilanediylbis(2-ethyl-4-phenylindenyl) zirconiumCH$_2$CHCHCH$_2$bis(pentafluorophenyl) isoindolylborate dimethylsilanediylbis(2-methyl-4-(4'-tert-butylphenyl)indenyl)zirconiumCH$_2$CHCHCH$_2$bis (pentafluorophenyl)isoindolylborate dimethylsilanediylbis(2-methyl-4-(4'-methylphenyl) indenyl)zirconiumCH$_2$CHCHCH$_2$bis (pentafluorophenyl)isoindolylborate dimethylsilanediylbis(2-methyl-4-(4'-ethylphenyl) indenyl)zirconiumCH$_2$CHCHCH$_2$bis (pentafluorophenyl)isoindolylborate dimethylsilanediylbis(2-methyl-4-(4'-n-propylphenyl) indenyl)zirconiumCH$_2$CHCHCH$_2$bis (pentafluorophenyl)isoindolylborate dimethylsilanediylbis(2-methyl-4-(4'-isopropylphenyl) indenyl)zirconiumCH$_2$CHCHCH$_2$bis (pentafluorophenyl)isoindolylborate dimethylsilanediylbis(2-methyl-4-(4'-n-butylphenyl) indenyl)zirconiumCH$_2$CHCHCH$_2$bis (pentafluorophenyl)isoindolylborate dimethylsilanediylbis(2-methyl-4-(4'-hexylphenyl) indenyl)zirconiumCH$_2$CHCHCH$_2$bis (pentafluorophenyl)isoindolylborate dimethylsilanediylbis(2-methyl-4-(4'-sec-butylphenyl) indenyl)zirconiumCH$_2$CHCHCH$_2$bis (pentafluorophenyl)isoindolylborate dimethylsilanediylbis(2-ethyl-4-(4'-tert-butylphenyl) indenyl)zirconiumCH$_2$CHCHCH$_2$bis (pentafluorophenyl)isoindolylborate dimethylsilanediylbis(2-ethyl-4-(4'-methylphenyl) indenyl)zirconiumCH$_2$CHCHCH$_2$bis (pentafluorophenyl)isoindolylborate dimethylsilanediylbis(2-ethyl-4-(4'-ethylphenyl) indenyl)zirconiumCH$_2$CHCHCH$_2$bis (pentafluorophenyl)isoindolylborate dimethylsilanediylbis(2-ethyl-4-(4'-n-propylphenyl) indenyl)zirconiumCH$_2$CHCHCH$_2$bis (pentafluorophenyl)isoindolylborate dimethylsilanediylbis(2-ethyl-4-(4'-isopropylphenyl) indenyl)zirconiumCH$_2$CHCHCH$_2$bis (pentafluorophenyl)isoindolylborate dimethylsilanediylbis(2-ethyl-4-(4'-n-butylphenyl) indenyl)zirconiumCH$_2$CHCHCH$_2$bis (pentafluorophenyl)isoindolylborate dimethylsilanediylbis(2-ethyl-4-(4'-hexylphenyl) indenyl)zirconiumCH$_2$CHCHCH$_2$bis (pentafluorophenyl)isoindolylborate dimethylsilanediylbis(2-ethyl-4-(4'-sec-butylphenyl) indenyl)zirconiumCH$_2$CHCHCH$_2$bis (pentafluorophenyl)isoindolylborate dimethylsilanediylbis(2-n-propyl-4-(4'-tert-butylphenyl)indenyl)zirconiumCH$_2$CHCHCH$_2$bis (pentafluorophenyl)isoindolylborate dimethylsilanediylbis(2-n-propyl-4-(4'-methylphenyl) indenyl)zirconiumCH$_2$CHCHCH$_2$bis (pentafluorophenyl)isoindolylborate dimethylsilanediylbis(2-n-propyl-4-(4'-ethylphenyl) indenyl)zirconiumCH$_2$CHCHCH$_2$bis (pentafluorophenyl)isoindolylborate dimethylsilanediylbis(2-n-propyl-4-(4'-n-propylphenyl)indenyl)zirconiumCH$_2$CHCHCH$_2$bis (pentafluorophenyl)isoindolylborate dimethylsilanediylbis(2-n-propyl-4-(4'-isopropylphenyl)indenyl)zirconiumCH$_2$CHCHCH$_2$bis (pentafluorophenyl)isoindolylborate dimethylsilanediylbis(2-n-propyl-4-(4'-n-butylphenyl) indenyl)zirconiumCH$_2$CHCHCH$_2$bis (pentafluorophenyl)isoindolylborate dimethylsilanediylbis(2-n-propyl-4-(4'-hexylphenyl) indenyl)zirconiumCH$_2$CHCHCH$_2$bis (pentafluorophenyl)isoindolylborate dimethylsilanediylbis(2-n-propyl-4-(4'-sec-butylphenyl)indenyl)zirconiumCH$_2$CHCHCH$_2$bis (pentafluorophenyl)isoindolylborate dimethylsilanediylbis(2-n-butyl-4-(4'-tert-butylphenyl) indenyl)zirconiumCH$_2$CHCHCH$_2$bis (pentafluorophenyl)isoindolylborate dimethylsilanediylbis(2-n-butyl-4-(4'-methylphenyl) indenyl)zirconiumCH$_2$CHCHCH$_2$bis (pentafluorophenyl)isoindolylborate dimethylsilanediylbis(2-n-butyl-4-(4'-ethylphenyl) indenyl)zirconiumCH$_2$CHCHCH$_2$bis (pentafluorophenyl)isoindolylborate dimethylsilanediylbis(2-n-butyl-4-(4'-n-propylphenyl) indenyl)zirconiumCH$_2$CHCHCH$_2$bis (pentafluorophenyl)isoindolylborate dimethylsilanediylbis(2-n-butyl-4-(4'-isopropylphenyl)indenyl)zirconiumCH$_2$CHCHCH$_2$bis (pentafluorophenyl)isoindolylborate dimethylsilanediylbis(2-n-butyl-4-(4'-n-butylphenyl) indenyl)zirconiumCH$_2$CHCHCH$_2$bis (pentafluorophenyl)isoindolylborate dimethylsilanediylbis(2-n-butyl-4-(4'-hexylphenyl) indenyl)zirconiumCH$_2$CHCHCH$_2$bis (pentafluorophenyl)isoindolylborate dimethylsilanediylbis(2-n-butyl-4-(4'-sec-butylphenyl) indenyl)zirconiumCH$_2$CHCHCH$_2$bis (pentafluorophenyl)isoindolylborate dimethylsilanediylbis(2-n-hexyl-4-(4'-tert-butylphenyl)indenyl)zirconiumCH$_2$CHCHCH$_2$bis (pentafluorophenyl)isoindolylborate dimethylsilanediylbis(2-n-hexyl-4-(4'-methylphenyl) indenyl)zirconiumCH$_2$CHCHCH$_2$bis (pentafluorophenyl)isoindolylborate dimethylsilanediylbis(2-n-hexyl-4-(4'-ethylphenyl) indenyl)zirconiumCH$_2$CHCHCH$_2$bis (pentafluorophenyl)isoindolylborate dimethylsilanediylbis(2-n-hexyl-4-(4'-n-propylphenyl) indenyl)zirconiumCH$_2$CHCHCH$_2$bis (pentafluorophenyl)isoindolylborate dimethylsilanediylbis(2-n-hexyl-4-(4'-isopropylphenyl)indenyl)zirconiumCH$_2$CHCHCH$_2$bis (pentafluorophenyl)isoindolylborate dimethylsilanediylbis(2-n-hexyl-4-(4'-n-butylphenyl) indenyl)zirconiumCH$_2$CHCHCH$_2$bis (pentafluorophenyl)isoindolylborate dimethylsilanediylbis(2-n-hexyl-4-(4'-hexylphenyl) indenyl)zirconiumCH$_2$CHCHCH$_2$bis (pentafluorophenyl)isoindolylborate dimethylsilanediylbis(2-n-hexyl-4-(4'-secbutylphenyl)indenyl)zirconiumCH$_2$CHCHCH$_2$bis(pentafluorophenyl)isoindolylborate dimethylsilanediylbis(2-methyl-4,5-benzoindenyl)zirconiumCH$_2$CHCHCH$_2$bis(pentafluorophenyl)isoindolylborate dimethylsilanediylbis(2-methyl-4,6-diisopropylindenyl)zirconiumCH$_2$CHCHCH$_2$bis(pentafluorophenyl)isoindolylborate dimethylsilanediylbis(2,4,6-trimethylindenyl)zirconiumCH$_2$CHCHCH$_2$bis(pentafluorophenyl)isoindolylborate dimethylsilanediylbis(2,5,6-trimethylindenyl)zirconiumCH$_2$CHCHCH$_2$bis(pentafluorophenyl)isoindolylborate dimethylsilanediylbis(2,4,7-trimethylindenyl)zirconiumCH$_2$CHCHCH$_2$bis(pentafluorophenyl)isoindolylborate dimethylsilanediylbis(2-methyl-5-isobutylindenyl)zirconiumCH$_2$CHCHCH$_2$bis(pentafluorophenyl)isoindolylborate dimethylsilanediylbis(2-methyl-5-tert-butylindenyl)zirconiumCH$_2$CHCHCH$_2$bis(pentafluorophenyl)isoindolylborate methyl(phenyl)silanediylbis(indenyl)zirconiumCH$_2$CHCHCH$_2$bis(pentafluorophenyl)isoindolylborate methyl(phenyl)silanediylbis(2-methylindenyl)zirconiumCH$_2$CHCHCH$_2$bis(pentafluorophenyl)isoindolylborate methyl(phenyl)silanediylbis(2-methylbenzindenyl)zirconiumCH$_2$CHCHCH$_2$bis(pentafluorophenyl)isoindolylborate methyl(phenyl)silanediylbis(4-phenylindenyl)zirconiumCH$_2$CHCHCH$_2$bis(pentafluorophenyl)isoindolylborate methyl(phenyl)silanediylbis(4-naphthylindenyl)zirconiumCH$_2$CHCHCH$_2$bis(pentafluorophenyl)isoindolylborate methyl(phenyl)silanediylbis(2-methyl-4-(1-naphthyl)indenyl)zirconiumCH$_2$CHCHCH$_2$bis(pentafluorophenyl)isoindolylborate methyl(phenyl)silanediylbis(2-methyl-4-(2-naphthyl)indenyl)zirconiumCH$_2$CHCHCH$_2$bis(pentafluorophenyl)isoindolylborate methyl(phenyl)silanediylbis(2-methyl-4-phenylindenyl)zirconiumCH$_2$CHCHCH$_2$bis(pentafluorophenyl)isoindolylborate methyl(phenyl)silanediylbis(2-methyl-4-tert-butylindenyl)zirconiumCH$_2$CHCHCH$_2$bis(pentafluorophenyl)isoindolylborate methyl(phenyl)silanediylbis(2-methyl-4-isopropylindenyl)zirconiumCH$_2$CHCHCH$_2$bis(pentafluorophenyl)isoindolylborate methyl(phenyl)silanediylbis(2-methyl-4-(1-naphthyl)indenyl)zirconiumCH$_2$CHCHCH$_2$bis(pentafluorophenyl)isoindolylborate methyl(phenyl)silanediylbis(2-methyl-4-ethylindenyl)zirconiumCH$_2$CHCHCH$_2$bis(pentafluorophenyl)isoindolylborate methyl(phenyl)silanediylbis(2-methyl-4-(acenaphthyl)indenyl)zirconiumCH$_2$CHCHCH$_2$bis(pentafluorophenyl)isoindolylborate methyl(phenyl)silanediylbis(2,4-dimethylindenyl)zirconiumCH$_2$CHCHCH$_2$bis(pentafluorophenyl)isoindolylborate methyl(phenyl)silanediylbis(2-ethylindenyl)zirconiumCH$_2$CHCHCH$_2$bis(pentafluorophenyl)isoindolylborate methyl(phenyl)silanediylbis(2-ethyl-4-ethylindenyl)zirconiumCH$_2$CHCHCH$_2$bis(pentafluorophenyl)isoindolylborate methyl(phenyl)silanediylbis(2-ethyl-4-phenylindenyl)zirconiumCH$_2$CHCHCH$_2$bis(pentafluorophenyl)isoindolylborate methyl(phenyl)silanediylbis(2-methyl-4,5-benzoindenyl)zirconiumCH$_2$CHCHCH$_2$bis(pentafluorophenyl)isoindolylborate methyl(phenyl)silanediylbis(2-methyl-4,6-diisopropylindenyl)zirconiumCH$_2$CHCHCH$_2$bis(pentafluorophenyl)isoindolylborate methyl(phenyl)silanediylbis(2,4,6-trimethylindenyl)zirconiumCH$_2$CHCHCH$_2$bis(pentafluorophenyl)isoindolylborate methyl(phenyl)silanediylbis(2,5,6-trimethylindenyl)zirconiumCH$_2$CHCHCH$_2$bis(pentafluorophenyl)isoindolylborate methyl(phenyl)silanediylbis(2,4,7-trimethylindenyl)zirconiumCH$_2$CHCHCH$_2$bis(pentafluorophenyl)isoindolylborate methyl(phenyl)silanediylbis(2-methyl-5-isobutylindenyl)zirconiumCH$_2$CHCHCH$_2$bis(pentafluorophenyl)isoindolylborate methyl(phenyl)silanediylbis(2-methyl-5-tert-butylindenyl)zirconiumCH$_2$CHCHCH$_2$bis(pentafluorophenyl)isoindolylborate diphenylmethylene(fluorenyl)(cyclopentadienyl)zirconiumCH$_2$CHCHCH$_2$bis(pentafluorophenyl)isoindolylborate dimethylmethylene(fluorenyl)(cyclopentadienyl)zirconiumCH$_2$CHCHCH$_2$bis(pentafluorophenyl)isoindolylborate methylphenylmethylene(fluorenyl)(cyclopentadienyl)zirconiumCH$_2$CHCHCH$_2$bis(pentafluorophenyl)isoindolylborate dimethylsilanediyl(3-tert-butylcyclopentadienyl)(fluorenyl)zirconiumCH$_2$CHCHCH$_2$bis(pentafluorophenyl)isoindolylborate diphenylsilanediyl(3-(trimethyl)cyclopentadienyl)(fluorenyl)zirconiumCH$_2$CHCHCH$_2$bis(pentafluorophenyl)isoindolylborate ethylenebis(indenyl)zirconiumCH$_2$CHCHCH$_2$bis(pentafluorophenyl)isoindolylborate ethylenebis(2-methylindenyl)zirconiumCH$_2$CHCHCH$_2$bis(pentafluorophenyl)isoindolylborate ethylenebis(2-methyl-4-phenylindenyl)zirconiumCH$_2$CHCHCH$_2$bis(pentafluorophenyl)isoindolylborate ethylenebis(2-methyl-4,5-benzindenyl)zirconiumCH$_2$CHCHCH$_2$bis(pentafluorophenyl)isoindolylborate ethylenebis(2-methyl-4,6-diisopropylindenyl)zirconiumCH$_2$CHCHCH$_2$bis(pentafluorophenyl)isoindolylborate 1,6-{bis[methylsilylbis(2-methyl-4-phenylindenyl)zirconiumCH$_2$CHCHCH$_2$bis(pentafluorophenyl)isoindolylborate}hexane 1,6-{bis[methylsilylbis(2-ethyl-4-phenylindenyl)zirconiumCH$_2$CHCHCH$_2$bis(pentafluorophenyl)isoindolylborate}hexane 1,6-{bis[methylsilylbis(2-methyl-4-naphthylphenylindenyl)zirconiumCH$_2$CHCHCH$_2$bis(pentafluorophenyl)isoindolylborate}hexane 1,6-{bis[methylsilyl-bis(2-methyl-4,5-benzoindenyl)zirconiumCH$_2$CHCHCH$_2$bis(pentafluorophenyl)isoindolylborate}hexane 1,6-{bis[methylsilyl(2-methyl-4-phenylindenyl)(2-methylindenylzirconiumCH$_2$CHCHCH$_2$bis(pentafluorophenyl)isoindolylborate}hexane 1,6-{bis[methylsilylbis(2-methyl-4-phenylindenyl)zirconiumCH$_2$CHCHCH$_2$bis(pentafluorophenyl)isoindolylborate}ethane 1,6-{bis[methylsilylbis(2-ethyl-4-phenylindenyl)zirconiumCH$_2$CHCHCH$_2$bis(pentafluorophenyl)isoindolylborate}ethane 1,6-{bis[methylsilylbis(2-methyl-4-naphthylphenylindenyl)zirconiumCH$_2$CHCHCH$_2$bis(pentafluorophenyl)isoindolylborate}ethane 1,6-{bis[methylsilylbis(2-methyl-4,5-benzoindenyl)zirconiumCH$_2$CHCHCH$_2$bis(pentafluorophenyl)isoindolylborate}ethane 1,6-{bis[methylsilyl(2-methyl-4-phenylindenyl)(2-methylindenylzirconiumCH$_2$CHCHCH$_2$bis(pentafluorophenyl)isoindolylborate}ethane tri(cyclopentadienyl)zirconiummethylbis(pentafluorophenyl)isoindolylborate tri (methylcyclopentadienyl)zirconiummethylbis(pentafluorophenyl)isoindolylborate tri(pentamethylcyclopentadienyl)zirconiummethylbis(pentafluorophenyl)isoindolylborate tri(n-butylcyclopentadienyl)zirconiummethylbis(pentafluorophenyl)isoindolylborate bis(cyclopentadienyl)zirconium$CH_2CHCHCH_2$bis(pentafluorophenyl)benzimidazolylborate bis(methylcyclopentadienyl)zirconium$CH_2CHCHCH_2$bis(pentafluorophenyl)benzimidazolylborate bis(pentamethylcyclopentadienyl)zirconium$CH_2CHCHCH_2$bis(pentafluorophenyl)benzimidazolylborate bis(n-butylcyclopentadienyl)zirconium$CH_2CHCHCH_2$bis(pentafluorophenyl)benzimidazolylborate bis(indenyl)zirconium$CH_2CHCHCH_2$bis(pentafluorophenyl)benzimidazolylborate bis(2-methylindenyl)zirconium$CH_2CHCHCH_2$bis(pentafluorophenyl)benzimidazolylborate bis(2-methylbenzindenyl)zirconium$CH_2CHCHCH_2$bis(pentafluorophenyl)benzimidazolylborate (tert-butylamido)dimethyl(tetramethyl-$\eta^5$-cyclopentadienyl)silanemethylzirconiummethylbis(pentafluorophenyl)benzimidazolylborate dimethylsilanediylbis(indenyl)zirconium$CH_2CHCHCH_2$bis(pentafluorophenyl)benzimidazolylborate dimethylsilanediylbis(2-methylindenyl)zirconium$CH_2CHCHCH_2$bis(pentafluorophenyl)benzimidazolylborate dimethylsilanediylbis(2-methylbenzindenyl)zirconium$CH_2CHCHCH_2$bis(pentafluorophenyl)benzimidazolylborate dimethylsilanediylbis(4-phenylindenyl)zirconium$CH_2CHCHCH_2$bis(pentafluorophenyl)benzimidazolylborate dimethylsilanediylbis(4-naphthylindenyl)zirconium$CH_2CHCHCH_2$bis(pentafluorophenyl)benzimidazolylborate dimethylsilanediylbis(2-methyl-4-(1-naphthyl)indenyl)zirconium$CH_2CHCHCH_2$bis(pentafluorophenyl)benzimidazolylborate dimethylsilanediylbis(2-methyl-4-(2-naphthyl)indenyl)zirconium$CH_2CHCHCH_2$bis(pentafluorophenyl)benzimidazolylborate dimethylsilanediylbis(2-methyl-4-phenylindenyl)zirconium$CH_2CHCHCH_2$bis(pentafluorophenyl)benzimidazolylborate dimethylsilanediylbis(2-methyl-4-tert-butylindenyl)zirconium$CH_2CHCHCH_2$bis(pentafluorophenyl)benzimidazolylborate dimethylsilanediylbis(2-methyl-4-isopropylindenyl)zirconium$CH_2CHCHCH_2$bis(pentafluorophenyl)benzimidazolylborate dimethylsilanediylbis(2-methyl-4-(1-naphthyl)indenyl)zirconium$CH_2CHCHCH_2$bis(pentafluorophenyl)benzimidazolylborate dimethylsilanediylbis(2-methyl-4-ethylindenyl)zirconium$CH_2CHCHCH_2$bis(pentafluorophenyl)benzimidazolylborate dimethylsilanediylbis(2-methyl-4-(acenaphthyl)indenyl)zirconium$CH_2CHCHCH_2$bis(pentafluorophenyl)benzimidazolylborate dimethylsilanediylbis(2,4-dimethylindenyl)zirconium$CH_2CHCHCH_2$bis(pentafluorophenyl)benzimidazolylborate dimethylsilanediylbis(2-ethylindenyl)zirconium$CH_2CHCHCH_2$bis(pentafluorophenyl)benzimidazolylborate dimethylsilanediylbis(2-ethyl-4-ethylindenyl)zirconium$CH_2CHCHCH_2$bis(pentafluorophenyl)benzimidazolylborate dimethylsilanediylbis(2-ethyl-4-phenylindenyl)zirconium$CH_2CHCHCH_2$bis(pentafluorophenyl)benzimidazolylborate dimethylsilanediylbis(2-methyl-4-(4'-tert-butylphenyl)indenyl)zirconium$CH_2CHCHCH_2$bis(pentafluorophenyl)benzimidazolylborate dimethylsilanediylbis(2-methyl-4-(4'-methylphenyl)indenyl)zirconium$CH_2CHCHCH_2$bis(pentafluorophenyl)benzimidazolylborate dimethylsilanediylbis(2-methyl-4-(4'-ethylphenyl)indenyl)zirconium$CH_2CHCHCH_2$bis(pentafluorophenyl)benzimidazolylborate dimethylsilanediylbis(2-methyl-4-(4'-n-propylphenyl)indenyl)zirconium$CH_2CHCHCH_2$bis(pentafluorophenyl)benzimidazolylborate dimethylsilanediylbis(2-methyl-4-(4'-isopropylphenyl)indenyl)zirconium$CH_2CHCHCH_2$bis(pentafluorophenyl)benzimidazolylborate dimethylsilanediylbis(2-methyl-4-(4'n-butylphenyl)indenyl)zirconium$CH_2CHCHCH_2$bis(pentafluorophenyl)benzimidazolylborate dimethylsilanediylbis(2-methyl-4-(4'-hexylphenyl)indenyl)zirconium$CH_2CHCHCH_2$bis(pentafluorophenyl)benzimidazolylborate dimethylsilanediylbis(2-methyl-4-(4'-sec-butylphenyl)indenyl)zirconium$CH_2CHCHCH_2$bis(pentafluorophenyl)benzimidazolylborate dimethylsilanediylbis(2-ethyl-4-(4'-tert-butylphenyl)indenyl)zirconium$CH_2CHCHCH_2$bis(pentafluorophenyl)benzimidazolylborate dimethylsilanediylbis(2-ethyl-4-(4'-methylphenyl)indenyl)zirconium$CH_2CHCHCH_2$bis(pentafluorophenyl)benzimidazolylborate dimethylsilanediylbis(2-ethyl-4-(4'-ethylphenyl)indenyl)zirconium$CH_2CHCHCH_2$bis(pentafluorophenyl)benzimidazolylborate dimethylsilanediylbis(2-ethyl-4-(4'-n-propylphenyl)indenyl)zirconium$CH_2CHCHCH_2$bis(pentafluorophenyl)benzimidazolylborate dimethylsilanediylbis(2-ethyl-4-(4'-isopropylphenyl)indenyl)zirconium$CH_2CHCHCH_2$bis(pentafluorophenyl)benzimidazolylborate dimethylsilanediylbis(2-ethyl-4-(4'-n-butylphenyl)indenyl)zirconium$CH_2CHCHCH_2$bis(pentafluorophenyl)benzimidazolylborate dimethylsilanediylbis(2-ethyl-4-(4'hexylphenyl)indenyl)zirconium$CH_2CHCHCH_2$bis(pentafluorophenyl)benzimidazolylborate dimethylsilanediylbis(2-ethyl-4-(4'-sec-butylphenyl)indenyl)zirconium$CH_2CHCHCH_2$bis(pentafluorophenyl)benzimidazolylborate dimethylsilanediylbis(2-n-propyl-4-(4'tert-butylphenyl)indenyl)zirconium$CH_2CHCHCH_2$bis(pentafluorophenyl)benzimidazolylborate dimethylsilanediylbis(2-n-propyl-4-(4'-methylphenyl)indenyl)zirconium$CH_2CHCHCH_2$bis(pentafluorophenyl)benzimidazolylborate dimethylsilanediylbis(2-n-propyl-4-(4'-ethylphenyl)indenyl)zirconium$CH_2CHCHCH_2$bis(pentafluorophenyl)benzimidazolylborate dimethylsilanediylbis(2-n-propyl-4-(4'n-propylphenyl)indenyl)zirconium$CH_2CHCHCH_2$bis(pentafluorophenyl)benzimidazolylborate dimethylsilanediylbis(2-n-propyl-4-(4'-isopropylphenyl)indenyl)zirconium$CH_2CHCHCH_2$bis(pentafluorophenyl)benzimidazolylborate dimethylsilanediylbis(2-n-propyl-4-(4'-n-butylphenyl)indenyl)zirconium$CH_2CHCHCH_2$bis(pentafluorophenyl)benzimidazolylborate dimethylsilanediylbis(2-n-propyl-4-(4'-hexylphenyl)indenyl)zirconium$CH_2CHCHCH_2$bis (pentafluorophenyl)benzimidazolylborate dimethylsilanediylbis(2-n-propyl-4-(4'-sec-butylphenyl)indenyl)zirconiumCH$_2$CHCHCH$_2$bis(pentafluorophenyl)benzimidazolylborate dimethylsilanediylbis(2-n-butyl-4-(4'tert-butylphenyl)indenyl)zirconiumCH$_2$CHCHCH$_2$bis(pentafluorophenyl)benzimidazolylborate dimethylsilanediylbis(2-n-butyl-4-(4'-methylphenyl)indenyl)zirconiumCH$_2$CHCHCH$_2$bis(pentafluorophenyl)benzimidazolylborate dimethylsilanediylbis(2-n-butyl-4-(4'-ethylphenyl)indenyl)zirconiumCH$_2$CHCHCH$_2$bis(pentafluorophenyl)benzimidazolylborate dimethylsilanediylbis(2-n-butyl-4-(4'-n-propylphenyl)indenyl)zirconiumCH$_2$CHCHCH$_2$bis(pentafluorophenyl)benzimidazolylborate dimethylsilanediylbis(2-n-butyl-4-(4'-isopropylphenyl)indenyl)zirconiumCH$_2$CHCHCH$_2$bis(pentafluorophenyl)benzimidazolylborate dimethylsilanediylbis(2-n-butyl-4-(4'-n-butylphenyl)indenyl)zirconiumCH$_2$CHCHCH$_2$bis(pentafluorophenyl)benzimidazolylborate dimethylsilanediylbis(2-n-butyl-4-(4'hexylphenyl)indenyl)zirconiumCH$_2$CHCHCH$_2$bis(pentafluorophenyl)benzimidazolylborate dimethylsilanediylbis(2-n-butyl-4-(4'-sec-butylphenyl)indenyl)zirconiumCH$_2$CHCHCH$_2$bis(pentafluorophenyl)benzimidazolylborate dimethylsilanediylbis(2-n-hexyl-4-(4'-tert-butylphenyl)indenyl)zirconiumCH$_2$CHCHCH$_2$bis(pentafluorophenyl)benzimidazolylborate dimethylsilanediylbis(2-n-hexyl-4-(4'-methylphenyl)indenyl)zirconiumCH$_2$CHCHCH$_2$bis(pentafluorophenyl)benzimidazolylborate dimethylsilanediylbis(2-n-hexyl-4-(4'-ethylphenyl)indenyl)zirconiumCH$_2$CHCHCH$_2$bis(pentafluorophenyl)benzimidazolylborate dimethylsilanediylbis(2-n-hexyl-4-(4'-n-propylphenyl)indenyl)zirconiumCH$_2$CHCHCH$_2$bis(pentafluorophenyl)benzimidazolylborate dimethylsilanediylbis(2-n-hexyl-4-(4'-isopropylphenyl)indenyl)zirconiumCH$_2$CHCHCH$_2$bis(pentafluorophenyl)benzimidazolylborate dimethylsilanediylbis(2-n-hexyl-4-(4'-n-butylphenyl)indenyl)zirconiumCH$_2$CHCHCH$_2$bis(pentafluorophenyl)benzimidazolylborate dimethylsilanediylbis(2-n-hexyl-4-(4'-hexylphenyl)indenyl)zirconiumCH$_2$CHCHCH$_2$bis(pentafluorophenyl)benzimidazolylborate dimethylsilanediylbis(2-n-hexyl-4-(4'-sec-butylphenyl)indenyl)zirconiumCH$_2$CHCHCH$_2$bis(pentafluorophenyl)benzimidazolylborate dimethylsilanediylbis(2-methyl-4,5-benzoindenyl)zirconiumCH$_2$CHCHCH$_2$bis(pentafluorophenyl)benzimidazolylborate dimethylsilanediylbis(2-methyl-4,6-diisopropylindenyl)zirconiumCH$_2$CHCHCH$_2$bis(pentafluorophenyl)benzimidazolylborate dimethylsilanediylbis(2,4,6-trimethylindenyl)zirconiumCH$_2$CHCHCH$_2$bis(pentafluorophenyl)benzimidazolylborate dimethylsilanediylbis(2,5,6-trimethylindenyl)zirconiumCH$_2$CHCHCH$_2$bis(pentafluorophenyl)benzimidazolylborate dimethylsilanediylbis(2,4,7-trimethylindenyl)zirconiumCH$_2$CHCHCH$_2$bis(pentafluorophenyl)benzimidazolylborate dimethylsilanediylbis(2-methyl-5-isobutylindenyl)zirconiumCH$_2$CHCHCH$_2$bis(pentafluorophenyl)benzimidazolylborate dimethylsilanediylbis(2-methyl-5-tert-butylindenyl)zirconiumCH$_2$CHCHCH$_2$bis(pentafluorophenyl)benzimidazolylborate methyl(phenyl)silanediylbis(indenyl)zirconiumCH$_2$CHCHCH$_2$bis(pentafluorophenyl)benzimidazolylborate methyl(phenyl)silanediylbis(2-methylindenyl)zirconiumCH$_2$CHCHCH$_2$bis(pentafluorophenyl)benzimidazolylborate methyl(phenyl)silanediylbis(2-methylbenzindenyl)zirconiumCH$_2$CHCHCH$_2$bis(pentafluorophenyl)benzimidazolylborate methyl(phenyl)silanediylbis(4-phenylindenyl,)zirconiumCH$_2$CHCHCH$_2$bis(pentafluorophenyl)benzimidazolylborate methyl(phenyl)silanediylbis(4-naphthylindenyl)zirconiumCH$_2$CHCHCH$_2$bis(pentafluorophenyl)benzimidazolylborate methyl(phenyl)silanediylbis(2-methyl-4-(1-naphthyl)indenyl)zirconiumCH$_2$CHCHCH$_2$bis(pentafluorophenyl)benzimidazolylborate methyl(phenyl)silanediylbis(2-methyl-4-(2-naphthyl)indenyl)zirconiumCH$_2$CHCHCH$_2$bis(pentafluorophenyl)benzimidazolylborate methyl(phenyl)silanediylbis(2-methyl-4-phenylindenyl)zirconiumCH$_2$CHCHCH$_2$bis(pentafluorophenyl)benzimidazolylborate methyl(phenyl)silanediylbis(2-methyl-4-tert-butylindenyl)zirconiumCH$_2$CHCHCH$_2$bis(pentafluorophenyl)benzimidazolylborate methyl(phenyl)silanediylbis(2-methyl-4-isopropylindenyl)zirconiumCH$_2$CHCHCH$_2$bis(pentafluorophenyl)benzimidazolylborate methyl(phenyl)silanediylbis(2-methyl-4-(1-naphthyl)indenyl)zirconiumCH$_2$CHCHCH$_2$bis(pentafluorophenyl)benzimidazolylborate methyl(phenyl)silanediylbis(2-methyl-4-ethylindenyl)zirconiumCH$_2$CHCHCH$_2$bis(pentafluorophenyl)benzimidazolylborate methyl(phenyl)silanediylbis(2-methyl-4-(acenaphthyl)indenyl)zirconiumCH$_2$CHCHCH$_2$bis(pentafluorophenyl)benzimidazolylborate methyl(phenyl)silanediylbis(2,4-dimethylindenyl)zirconiumCH$_2$CHCHCH$_2$bis(pentafluorophenyl)benzimidazolylborate methyl(phenyl)silanediylbis(2-ethylindenyl)zirconiumCH$_2$CHCHCH$_2$bis(pentafluorophenyl)benzimidazolylborate methyl(phenyl)silanediylbis(2-ethyl-4-ethylindenyl)zirconiumCH$_2$CHCHCH$_2$bis(pentafluorophenyl)benzimidazolylborate methyl(phenyl)silanediylbis(2-ethyl-4-phenylindenyl)zirconiumCH$_2$CHCHCH$_2$bis(pentafluorophenyl)benzimidazolylborate methyl(phenyl)silanediylbis(2-methyl-4,5-benzoindenyl)zirconiumCH$_2$CHCHCH$_2$bis(pentafluorophenyl)benzimidazolylborate methyl(phenyl)silanediylbis(2-methyl-4,6-diisopropylindenyl)zirconiumCH$_2$CHCHCH$_2$bis(pentafluorophenyl)benzimidazolylborate methyl(phenyl)silanediylbis(2,4,6-trimethylindenyl)zirconiumCH$_2$CHCHCH$_2$bis(pentafluorophenyl)benzimidazolylborate methyl(phenyl)silanediylbis(2,5,6-trimethylindenyl)zirconiumCH$_2$CHCHCH$_2$bis(pentafluorophenyl)benzimidazolylborate methyl(phenyl)silanediylbis(2,4,7-trimethylindenyl)zirconiumCH$_2$CHCHCH$_2$bis(pentafluorophenyl)benzimidazolylborate methyl(phenyl)silanediylbis(2-methyl-5-isobutylindenyl)zirconiumCH$_2$CHCHCH$_2$bis(pentafluorophenyl)benzimidazolylborate methyl(phenyl)silanediylbis(2-methyl-5-tert-butylindenyl)zirconiumCH$_2$CHCHCH$_2$bis(pentafluorophenyl)benzimidazolylborate diphenylmethylene(fluorenyl)(cyclopentadienyl)zirconiumCH$_2$CHCHCH$_2$bis (pentafluorophenyl)benzimidazolylborate dimethylmethylene(fluorenyl)(cyclopentadienyl)zirconiumCH₂CHCHCH₂bis(pentafluorophenyl)benzimidazolylborate methylphenylmethylene(fluorenyl)(cyclopentadienyl)zirconiumCH₂CHCHCH₂bis(pentafluorophenyl)benzimidazolylborate dimethylsilanediyl(3-tert-butylcyclopentadienyl)(fluorenyl)zirconiumCH₂CHCHCH₂bis(pentafluorophenyl)benzimidazolylborate diphenylsilanediyl(3-(trimethyl)cyclopentadienyl)(fluorenyl)zirconiumCH₂CHCHCH₂bis(pentafluorophenyl)benzimidazolylborate ethylenebis(indenyl)zirconiumCH₂CHCHCH₂bis(pentafluorophenyl)benzimidazolylborate ethylenebis(2-methylindenyl)zirconiumCH₂CHCHCH₂bis(pentafluorophenyl)benzimidazolylborate ethylenebis(2-methyl-4-phenylindenyl)zirconiumCH₂CHCHCH₂bis(pentafluorophenyl)benzimidazolylborate ethylenebis(2-methyl-4,5-benzindenyl)zirconiumCH₂CHCHCH₂bis(pentafluorophenyl)benzimidazolylborate ethylenebis(2-methyl-4,6-diisopropylindenyl)zirconiumCH₂CHCHCH₂bis(pentafluorophenyl)benzimidazolylborate 1,6-{bis[methylsilyl-bis(2-methyl-4-phenylindenyl)zirconiumCH₂CHCHCH₂bis(pentafluorophenyl)benzimidazolylborate}hexane 1,6-{bis[methylsilylbis(2-ethyl-4-phenylindenyl)zirconiumCH₂CHCHCH₂bis(pentafluorophenyl)benzimidazolylborate}hexane 1,6-{bis[methylsilyl-bis(2-methyl-4-naphthylphenylindenyl)zirconiumCH₂CHCHCH₂bis(pentafluorophenyl)benzimidazolylborate}hexane 1,6-{bis[methylsilylbis(2-methyl-4,5-benzoindenyl)zirconiumCH₂CHCHCH₂bis(pentafluorophenyl)benzimidazolylborate}hexane 1,6-{bis[methylsilyl(2-methyl-4-phenyl-indenyl)(2-methylindenylzirconiumCH₂CHCHCH₂bis(pentafluorophenyl)benzimidazolylborate}hexane 1,6-{bis[methylsilylbis(2-methyl-4-phenylindenyl)zirconiumCH₂CHCHCH₂bis(pentafluorophenyl)benzimidazolylborate}ethane 1,6-{bis[methylsilylbis(2-ethyl-4-phenylindenyl)zirconiumCH₂CHCHCH₂bis(pentafluorophenyl)benzimidazolylborate}ethane 1,6-{bis[methylsilylbis(2-methyl-4-naphthylphenylindenyl)zirconiumCH₂CHCHCH₂bis(pentafluorophenyl)benzimidazolylborate}ethane 1,6-{bis[methylsilylbis(2-methyl-4,5-benzoindenyl)zirconiumCH₂CHCHCH₂bis(pentafluorophenyl)benzimidazolylborate }ethane 1,6-{bis[methylsilyl(2-methyl-4-phenylindenyl)(2-methylindenylzirconiumCH₂CHCHCH₂bis(pentafluorophenyl)benzimidazolylborate}ethane tri(cyclopentadienyl)zirconiummethylbis(pentafluorophenyl)benzimidazolylborate tri(methylcyclopentadienyl)zirconiummethylbis(pentafluorophenyl)benzimidazolylborate tri(pentamethylcyclopentadienyl)zirconiummethylbis(pentafluorophenyl)benzimidazolylborate tri(n-butylcyclopentadienyl)zirconiummethylbis(pentafluorophenyl)benzimidazolylborate bis(cyclopentadienyl)zirconiumCH₂CHCHCH₂bis(pentafluorophenyl)indolylborate bis(methylcyclopentadienyl)zirconiumCH₂CHCHCH₂bis(pentafluorophenyl)indolylborate bis(pentamethylcyclopentadienyl)zirconiumCH₂CHCHCH₂bis(pentafluorophenyl)indolylborate bis(n-butylcyclopentadienyl)zirconiumCH₂CHCHCH₂bis(pentafluorophenyl)indolylborate bis(indenyl)zirconiumCH₂CHCHCH₂bis(pentafluorophenyl)indolylborate bis(2-methylindenyl)zirconiumCH₂CHCHCH₂bis(pentafluorophenyl)indolylborate bis(2-methylbenzindenyl)zirconiumCH₂CHCHCH₂bis(pentafluorophenyl)indolylborate (tert-butylamido)dimethyl(tetramethyl-η⁵-cyclopentadienyl)silanemethylzirconiummethylbis(pentafluorophenyl)indolylborate dimethylsilanediylbis(indenyl)zirconiumCH₂CHCHCH₂bis(pentafluorophenyl)indolylborate dimethylsilanediylbis(2-methylindenyl)zirconiumCH₂CHCHCH₂bis(pentafluorophenyl)indolylborate dimethylsilanediylbis(2-methylbenzindenyl)zirconiumCH₂CHCHCH₂bis(pentafluorophenyl)indolylborate dimethylsilanediylbis(4-phenylindenyl)zirconiumCH₂CHCHCH₂bis(pentafluorophenyl)indolylborate dimethylsilanediylbis(4-naphthylindenyl)zirconiumCH₂CHCHCH₂bis(pentafluorophenyl)indolylborate dimethylsilanediylbis(2-methyl-4-(1-naphthyl)indenyl)zirconiumCH₂CHCHCH₂bis(pentafluorophenyl)indolylborate dimethylsilanediylbis(2-methyl-4-(2-naphthyl)indenyl)zirconiumCH₂CHCHCH₂bis(pentafluorophenyl)indolylborate dimethylsilanediylbis(2-methyl-4-phenylindenyl)zirconiumCH₂CHCHCH₂bis(pentafluorophenyl)indolylborate dimethylsilanediylbis(2-methyl-4-tert-butylindenyl)zirconiumCH₂CHCHCH₂bis(pentafluorophenyl)indolylborate dimethylsilanediylbis(2-methyl-4-isopropylindenyl)zirconiumCH₂CHCHCH₂bis(pentafluorophenyl)indolylborate dimethylsilanediylbis(2-methyl-4-(1-naphthyl)indenyl)zirconiumCH₂CHCHCH₂bis(pentafluorophenyl)indolylborate dimethylsilanediylbis(2-methyl-4-ethylindenyl)zirconiumCH₂CHCHCH₂bis(pentafluorophenyl)indolylborate dimethylsilanediylbis(2-methyl-4-(acenaphthyl)indenyl)zirconiumCH₂CHCHCH₂bis(pentafluorophenyl)indolylborate dimethylsilanediylbis(2,4-dimethylindenyl)zirconiumCH₂CHCHCH₂bis(pentafluorophenyl)indolylborate dimethylsilanediylbis(2-ethylindenyl)zirconiumCH₂CHCHCH₂bis(pentafluorophenyl)indolylborate dimethylsilanediylbis(2-ethyl-4-ethylindenyl)zirconiumCH₂CHCHCH₂bis(pentafluorophenyl)indolylborate dimethylsilanediylbis(2-ethyl-4-phenylindenyl)zirconiumCH₂CHCHCH₂bis(pentafluorophenyl)indolylborate dimethylsilanediylbis(2-methyl-4-(4'tert-butylphenyl)indenyl)zirconiumCH₂CHCHCH₂bis(pentafluorophenyl)indolylborate dimethylsilanediylbis(2-methyl-4-(4'-methylphenyl)indenyl)zirconiumCH₂CHCHCH₂bis(pentafluorophenyl)indolylborate dimethylsilanediylbis(2-methyl-4-(4'ethylphenyl)indenyl)zirconiumCH₂CHCHCH₂bis(pentafluorophenyl)indolylborate dimethylsilanediylbis(2-methyl-4-(4'-n-propylphenyl)indenyl)zirconiumCH₂CHCHCH₂bis(pentafluorophenyl)indolylborate dimethylsilanediylbis(2-methyl-4(4'-isopropylphenyl)indenyl)zirconiumCH₂CHCHCH₂bis(pentafluorophenyl)indolylborate dimethylsilanediylbis(2-methyl-4-(4'-n-butylphenyl)

indenyl)zirconiumCH₂CHCHCH₂bis(pentafluorophenyl)indolylborate
dimethylsilanediylbis(2-methyl-4-(4'-hexylphenyl)indenyl)zirconiumCH₂CHCHCH₂bis(pentafluorophenyl)indolylborate
dimethylsilanediylbis(2-methyl-4-(4'-sec-butylphenyl)indenyl)zirconiumCH₂CHCHCH₂bis(pentafluorophenyl)indolylborate
dimethylsilanediylbis(2-ethyl-4-(4'tert-butylphenyl)indenyl)zirconiumCH₂CHCHCH₂bis(pentafluorophenyl)indolylborate
dimethylsilanediylbis(2-ethyl-4-(4'-methylphenyl)indenyl)zirconiumCH₂CHCHCH₂bis(pentafluorophenyl)indolylborate
dimethylsilanediylbis(2-ethyl-4-(4'-ethylphenyl)indenyl)zirconiumCH₂CHCHCH₂bis(pentafluorophenyl)indolylborate
dimethylsilanediylbis(2-ethyl-4-(4'-n-propylphenyl)indenyl)zirconiumCH₂CHCHCH₂bis(pentafluorophenyl)indolylborate
dimethylsilanediylbis(2-ethyl-4-(4'-isopropylphenyl)indenyl)zirconiumCH₂CHCHCH₂bis(pentafluorophenyl)indolylborate
dimethylsilanediylbis(2-ethyl-4-(4'-n-butylphenyl)indenyl)zirconiumCH₂CHCHCH₂bis(pentafluorophenyl)indolylborate
dimethylsilanediylbis(2-ethyl-4-(4'-hexylphenyl)indenyl)zirconium-CH₂CHCHCH₂bis(pentafluorophenyl)indolylborate
dimethylsilanediylbis(2-ethyl-4-(4'sec-butylphenyl)indenyl)zirconiumCH₂CHCHCH₂bis(pentafluorophenyl)indolylborate
dimethylsilanediylbis(2-n-propyl-4-(4'-tert-butylphenyl)indenyl)zirconiumCH₂CHCHCH₂bis(pentafluorophenyl)indolylborate
dimethylsilanediylbis(2-n-propyl-4-(4'-methylphenyl)indenyl)zirconiumCH₂CHCHCH₂bis(pentafluorophenyl)indolylborate
dimethylsilanediylbis(2-n-propyl-4-(4'-ethylphenyl)indenyl)zirconiumCH₂CHCHCH₂bis(pentafluorophenyl)indolylborate
dimethylsilanediylbis(2-n-propyl-4-(4'-n-propylphenyl)indenyl)zirconiumCH₂CHCHCH₂bis(pentafluorophenyl)indolylborate
dimethylsilanediylbis(2-n-propyl-4-(4'isopropylphenyl)indenyl)zirconiumCH₂CHCHCH₂bis(pentafluorophenyl)indolylborate
dimethylsilanediylbis(2-n-propyl-4-(4'n-butylphenyl)indenyl)zirconiumCH₂CHCHCH₂bis(pentafluorophenyl)indolylborate
dimethylsilanediylbis(2-n-propyl-4-(4'-hexylphenyl)indenyl)zirconiumCH₂CHCHCH₂bis(pentafluorophenyl)indolylborate
dimethylsilanediylbis(2-n-propyl-4-(4'-sec-butylphenyl)indenyl)zirconiumCH₂CHCHCH₂bis(pentafluorophenyl)indolylborate
dimethylsilanediylbis(2-n-butyl-4-(4'tert-butylphenyl)indenyl)zirconiumCH₂CHCHCH₂bis(pentafluorophenyl)indolylborate
dimethylsilanediylbis(2-n-butyl-4-(4'methylphenyl)indenyl)zirconiumCH₂CHCHCH₂bis(pentafluorophenyl)indolylborate
dimethylsilanediylbis(2-n-butyl-4-(4'-ethylphenyl)indenyl)zirconiumCH₂CHCHCH₂bis(pentafluorophenyl)indolylborate
dimethylsilanediylbis(2-n-butyl-4-(4'-n-propylphenyl)indenyl)zirconiumCH₂CHCHCH₂bis(pentafluorophenyl)indolylborate
dimethylsilanediylbis(2-n-butyl-4-(4'isopropylphenyl)indenyl)zirconiumCH₂CHCHCH₂bis(pentafluorophenyl)indolylborate
dimethylsilanediylbis(2-n-butyl-4-(4'n-butylphenyl)indenyl)zirconiumCH₂CHCHCH₂bis(pentafluorophenyl)indolylborate
dimethylsilanediylbis(2-n-butyl-4-(4'-hexylphenyl)indenyl)zirconiumCH₂CHCHCH₂bis(pentafluorophenyl)indolylborate
dimethylsilanediylbis(2-n-butyl-4-(4'-sec-butylphenyl)indenyl)zirconiumCH₂CHCHCH₂bis(pentafluorophenyl)indolylborate
dimethylsilanediylbis(2-n-hexyl-4-(4'-tert-butylphenyl)indenyl)zirconiumCH₂CHCHCH₂bis(pentafluorophenyl)indolylborate
dimethylsilanediylbis(2-n-hexyl-4-(4'-methylphenyl)indenyl)zirconiumCH₂CHCHCH₂bis(pentafluorophenyl)indolylborate
dimethylsilanediylbis(2-n-hexyl-4-(4'-ethylphenyl)indenyl)zirconiumCH₂CHCHCH₂bis(pentafluorophenyl)indolylborate
dimethylsilanediylbis(2-n-hexyl-4-(4'-n-propylphenyl)indenyl)zirconiumCH₂CHCHCH₂bis(pentafluorophenyl)indolylborate
dimethylsilanediylbis(2-n-hexyl-4-(4'-isopropylphenyl)indenyl)zirconiumCH₂CHCHCH₂bis(pentafluorophenyl)indolylborate
dimethylsilanediylbis(2-n-hexyl-4-(4'-n-butylphenyl)indenyl)zirconiumCH₂CHCHCH₂bis(pentafluorophenyl)indolylborate
dimethylsilanediylbis(2-n-hexyl-4-(4'-hexylphenyl)indenyl)zirconiumCH₂CHCHCH₂bis(pentafluorophenyl)indolylborate
dimethylsilanediylbis(2-n-hexyl-4-(4'sec-butylphenyl)indenyl)zirconiumCH₂CHCHCH₂bis(pentafluorophenyl)indolylborate
dimethylsilanediylbis(2-methyl-4,5-benzoindenyl)zirconiumCH₂CHCHCH₂bis(pentafluorophenyl)indolylborate
dimethylsilanediylbis(2-methyl-4,6-diisopropylindenyl)zirconiumCH₂CHCHCH₂bis(pentafluorophenyl)indolylborate
dimethylsilanediylbis(2,4,6-trimethylindenyl)zirconiumCH₂CHCHCH₂bis(pentafluorophenyl)indolylborate
dimethylsilanediylbis(2,5,6-trimethylindenyl)zirconiumCH₂CHCHCH₂bis(pentafluorophenyl)indolylborate
dimethylsilanediylbis(2,4,7-trimethylindenyl)zirconiumCH₂CHCHCH₂bis(pentafluorophenyl)indolylborate
dimethylsilanediylbis(2-methyl-5-isobutylindenyl)zirconiumCH₂CHCHCH₂bis(pentafluorophenyl)indolylborate
dimethylsilanediylbis(2-methyl-5-tert-butylindenyl)zirconiumCH₂CHCHCH₂bis(pentafluorophenyl)indolylborate
methyl(phenyl)silanediylbis(indenyl)zirconiumCH₂CHCHCH₂bis(pentafluorophenyl)indolylborate
methyl(phenyl)silanediylbis(2-methylindenyl)zirconiumCH₂CHCHCH₂bis(pentafluorophenyl)indolylborate
methyl(phenyl)silanediylbis(2-methylbenzindenyl)zirconiumCH₂CHCHCH₂bis(pentafluorophenyl)indolylborate
methyl(phenyl)silanediylbis(4-phenylindenyl)zirconiumCH₂CHCHCH₂bis(pentafluorophenyl)indolylborate
methyl(phenyl)silanediylbis(4-naphthylindenyl)zirconiumCH₂CHCHCH₂bis(pentafluorophenyl)indolylborate
methyl(phenyl)silanediylbis(2-methyl-4-

(1-naphthyl)indenyl)zirconiumCH₂CHCHCH₂bis(pentafluorophenyl)indolylborate methyl(phenyl)silanediylbis(2-methyl-4-(2-naphthyl)indenyl)zirconiumCH₂CHCHCH₂bis(pentafluorophenyl)indolylborate methyl(phenyl)silanediylbis(2-methyl-4-phenylindenyl)zirconiumCH₂CHCHCH₂bis(pentafluorophenyl)indolylborate methyl(phenyl)silanediylbis(2-methyl-4-tert-butylindenyl)zirconiumCH₂CHCHCH₂bis(pentafluorophenyl)indolylborate methyl(phenyl)silanediylbis(2-methyl-4-isopropylindenyl)zirconiumCH₂CHCHCH₂bis(pentafluorophenyl)indolylborate methyl(phenyl)silanediylbis(2-methyl-4-(1-naphthyl)indenyl)zirconiumCH₂CHCHCH₂bis(pentafluorophenyl)indolylborate methyl(phenyl)silanediylbis(2-methyl-4-ethylindenyl)zirconiumCH₂CHCHCH₂bis(pentafluorophenyl)indolylborate methyl(phenyl)silanediylbis(2-methyl-4-(acenaphthyl)indenyl)zirconiumCH₂CHCHCH₂bis(pentafluorophenyl)indolylborate methyl(phenyl)silanediylbis(2,4-dimethylindenyl)zirconiumCH₂CHCHCH₂bis(pentafluorophenyl)indolylborate methyl(phenyl)silanediylbis(2-ethylindenyl)zirconiumCH₂CHCHCH₂bis(pentafluorophenyl)indolylborate methyl(phenyl)silanediylbis(2-ethyl-4-ethylindenyl)zirconiumCH₂CHCHCH₂bis(pentafluorophenyl)indolylborate methyl(phenyl)silanediylbis(2-ethyl-4-phenylindenyl)zirconiumCH₂CHCHCH₂bis(pentafluorophenyl)indolylborate methyl(phenyl)silanediylbis(2-methyl-4,5-benzoindenyl)zirconiumCH₂CHCHCH₂bis(pentafluorophenyl)indolylborate methyl(phenyl)silanediylbis(2-methyl-4,6-diisopropylindenyl)zirconiumCH₂CHCHCH₂bis(pentafluorophenyl)indolylborate methyl(phenyl)silanediylbis(2,4,6-trimethylindenyl)zirconiumCH₂CHCHCH₂bis(pentafluorophenyl)indolylborate methyl(phenyl)silanediylbis(2,5,6-trimethylindenyl)zirconiumCH₂CHCHCH₂bis(pentafluorophenyl)indolylborate methyl(phenyl)silanediylbis(2,4,7-trimethylindenyl)zirconiumCH₂CHCHCH₂bis(pentafluorophenyl)indolylborate methyl(phenyl)silanediylbis(2-methyl-5-isobutylindenyl)zirconiumCH₂CHCHCH₂bis(pentafluorophenyl)indolylborate methyl(phenyl)silanediylbis(2-methyl-5-tert-butylindenyl)zirconiumCH₂CHCHCH₂bis(pentafluorophenyl)indolylborate diphenylmethylene(fluorenyl)(cyclopentadienyl)zirconiumCH₂CHCHCH₂bis(pentafluorophenyl)indolylborate dimethylmethylene(fluorenyl)(cyclopentadienyl)zirconiumCH₂CHCHCH₂bis(pentafluorophenyl)indolylborate methylphenylmethylene(fluorenyl)(cyclopentadienyl)zirconiumCH₂CHCHCH₂bis(pentafluorophenyl)indolylborate dimethylsilanediyl(3-tert-butylcyclopentadienyl)(fluorenyl)zirconiumCH₂CHCHCH₂bis(pentafluorophenyl)indolylborate diphenylsilanediyl(3-(trimethyl)cyclopentadienyl)(fluorenyl)zirconiumCH₂CHCHCH₂bis(pentafluorophenyl)indolylborate ethylenebis(indenyl)zirconiumCH₂CHCHCH₂bis(pentafluorophenyl)indolylborate ethylenebis(2-methylindenyl)zirconiumCH₂CHCHCH₂bis(pentafluorophenyl)indolylborate ethylenebis(2-methyl-4-phenyl-indenyl)zirconiumCH₂CHCHCH₂bis(pentafluorophenyl)indolylborate ethylenebis(2-methyl-4,5-benzindenyl)zirconiumCH₂CHCHCH₂bis(pentafluorophenyl)indolylborate ethylenebis(2-methyl-4,6-diisopropylindenyl)zirconiumCH₂CHCHCH₂bis(pentafluorophenyl)indolylborate 1,6-{bis[methylsilylbis(2-methyl-4-phenylindenyl)zirconiumCH₂CHCHCH₂bis(pentafluorophenyl)indolylborate}hexane 1,6-{bis[methylsilylbis(2-ethyl-4-phenylindenyl)zirconiumCH₂CHCHCH₂bis(pentafluorophenyl)indolylborate}hexane 1,6-{bis[methylsilyl-bis(2-methyl-4-naphthylphenylindenyl)zirconiumCH₂CHCHCH₂bis(pentafluorophenyl)indolylborate}hexane 1,6-{bis[methylsilylbis(2-methyl-4,5-benzoindenyl)zirconiumCH₂CHCHCH₂bis(pentafluorophenyl)indolylborate}hexane 1,6-{bis[methylsilyl(2-methyl-4-phenylindenyl)(2-methylindenylzirconiumCH₂CHCHCH₂bis(pentafluorophenyl)indolylborate}hexane 1,6-{bis[methylsilylbis(2-methyl-4-phenylindenyl)zirconiumCH₂CHCHCH₂bis(pentafluorophenyl)indolylborate}ethane 1,6-{bis[methylsilylbis(2-ethyl-4-phenylindenyl)zirconiumCH₂CHCHCH₂bis(pentafluorophenyl)indolylborate}ethane 1,6-{bis[methylsilylbis(2-methyl-4-naphthylphenylindenyl)zirconiumCH₂CHCHCH₂bis(pentafluorophenyl)indolylborate}ethane 1,6-{bis[methylsilylbis(2-methyl-4,5-benzoindenyl)zirconiumCH₂CHCHCH₂bis(pentafluorophenyl)indolylborate}ethane 1,6-{bis[methylsilyl(2-methyl-4-phenyl-indenyl)(2-methylindenylzirconiumCH₂CHCHCH₂bis(pentafluorophenyl)indolylborate}ethane tri(cyclopentadienyl)zirconiummethylbis(pentafluorophenyl)indolylborate tri(methylcyclopentadienyl)zirconiummethylbis(pentafluorophenyl)indolylborate tri(pentamethylcyclopentadienyl)zirconiummethylbis(pentafluorophenyl)indolylborate tri(n-butylcyclopentadienyl)zirconiummethylbis(pentafluorophenyl)indolylborate dimethylsilanediyl(2-methyl-4-azapentalene)(2-methyl-4-(4'-methylphenylindenyl)methylzirconiummethylbis(pentafluorophenyl)pyrrolylborate dimethylsilanediyl(2-methyl-5-azapentalene)(2-methyl-4-(4'-methylphenylindenyl)methylzirconiummethylbis(pentafluorophenyl)pyrrolylborate dimethylsilanediyl(2-methyl-6-azapentalene)(2-methyl-4-(4'-methylphenylindenyl)methylzirconiummethylbis(pentafluorophenyl)pyrrolylborate dimethylsilanediyl(2-methyl-N-phenyl-4-azapentalene)(2-methyl-4-(4'-methylphenylindenylmethylzirconiummethylbis(pentafluorophenyl)pyrrolylborate dimethylsilanediyl(2-methyl-N-phenyl-5-azapentalene)(2-methyl-4-(4'-methylphenylindenyl)methylzirconiummethylbis(pentafluorophenyl)pyrrolylborate dimethylsilanediyl(2-methyl-N-phenyl-6-azapentalene)(2-methyl-4-(4'-methylphenylindenyl)methylzirconiummethylbis(pentafluorophenyl)pyrrolylborate dimethylsilanediyl(2,5-dimethyl-4-azapentalene)(2-methyl-4-(4'-methylphenylindenyl)methylzirconiummethylbis(pentafluorophenyl)pyrrolylborate dimethylsilanediyl(2,5-dimethyl-6-azapentalene)(2-methyl-4-(4'-methylphenylindenyl)methylzirconiummethylbis(pentafluorophenyl)pyrrolylborate dimethylsilanediyl(2,5-dimethyl-N-phenyl-4-azapentalene)(2-methyl-4-(4'-methylphenylindenyl)methylzirconiummethylbis(pentafluorophenyl)pyrrolylborate dimethylsilanediyl(2,5-dimethyl-N-phenyl-6-azapentalene)(2-methyl-4-(4'-methylphenylindenyl)methylzirconiummethylbis (pentafluorophenyl)pyrrolylborate dimethylsilanediyl (2-methyl-4-thiapentalene)(2-methyl-4-(4'-methylphenylindenyl)methylzirconiummethylbis (pentafluorophenyl)pyrrolylborate dimethylsilanediyl (2-methyl-5-thiapentalene)(2-methyl-4-(4'-methylphenylindenyl)methylzirconiummethylbis (pentafluorophenyl)pyrrolylborate dimethylsilanediyl (2-methyl-6-thiapentalene)(2-methyl-4-(4'-methylphenylindenyl)methylzirconiummethylbis (pentafluorophenyl)pyrrolylborate dimethylsilanediyl (2,5-dimethyl-4-thiapentalene)(2-methyl-4-(4'-methylphenylindenyl)methylzirconiummethylbis (pentafluorophenyl)pyrrolylborate dimethylsilanediyl (2,5-dimethyl-6-thiapentalene)(2-methyl-4-(4'-methylphenylindenyl)methylzirconiummethylbis (pentafluorophenyl)pyrrolylborate dimethylsilanediyl (2-methyl-4-oxapentalene)(2-methyl-4-(4'-methylphenylindenyl)methylzirconiummethylbis (pentafluorophenyl)pyrrolylborate dimethylsilanediyl (2-methyl-5-oxapentalene)(2-methyl-4-(4'-methylphenylindenyl)methylzirconiummethylbis (pentafluorophenyl)pyrrolylborate dimethylsilanediyl (2-methyl-6-oxapentalene)(2-methyl-4-(4 1-methylphenylindenyl)methylzirconiummethylbis (pentafluorophenyl)pyrrolylborate dimethylsilanediyl (2,5-dimethyl-4-oxapentalene)(2-methyl-4-(4'-methylphenylindenyl)methylzirconiummethylbis (pentafluorophenyl)pyrrolylborate dimethylsilanediyl (2,5-dimethyl-6-oxapentalene)(2-methyl-4-(4'-methylphenylindenyl)methylzirconiummethylbis (pentafluorophenyl)pyrrolylborate dimethylsilanediyl (2-methyl-4-azapentalene)(2-methyl-4-(4'-ethyl-phenylindenyl)methylzirconiummethylbis (pentafluorophenyl)-pyrrolylborate dimethylsilanediyl (2-methyl-5-azapentalene)(2-methyl-4-(4'-ethyl-phenylindenyl)methylzirconiummethylbis (pentafluorophenyl)pyrrolylborate dimethylsilanediyl (2-methyl-6-azapentalene)(2-methyl-4-(4'-ethyl-phenylindenyl)methylzirconiummethylbis (pentafluorophenyl)pyrrolylborate dimethylsilanediyl (2-methyl-N-phenyl-4-azapentalene)(2-methyl-4-(4'-ethylphenylindenyl)methylzirconiummethylbis (pentafluorophenyl)pyrrolylborate dimethylsilanediyl (2-methyl-N-phenyl-5-azapentalene)(2-methyl-4-(4'-ethylphenylindenyl)methylzirconiummethylbis (pentafluorophenyl)pyrrolylborate dimethylsilanediyl (2-methyl-N-phenyl-6-azapentalene)(2-methyl-4-(4'-ethylphenylindenyl)methylzirconiummethylbis (pentafluorophenyl)pyrrolylborate dimethylsilanediyl (2,5-dimethyl-4-azapentalene)(2-methyl-4-(4'-ethylphenylindenyl)methylzirconiummethylbis (pentafluorophenyl)pyrrolylborate dimethylsilanediyl (2,5-dimethyl-6-azapentalene)(2-methyl-4-(4'-ethylphenylindenyl)methylzirconiummethylbis (pentafluorophenyl)pyrrolylborate dimethylsilanediyl (2,5-dimethyl-N-phenyl-4-azapentalene)(2-methyl-4-(4'ethylphenylindenyl)methylzirconiummethylbis (pentafluorophenyl)pyrrolylborate dimethylsilanediyl (2,5-dimethyl-N-phenyl-6-azapentalene)(2-methyl-4-(4'-ethylphenylindenyl)methylzirconiummethylbis (pentafluorophenyl)pyrrolylborate dimethylsilanediyl (2-methyl-4-thiapentalene)(2-methyl-4-(4'-ethylphenylindenyl)methylzirconiummethylbis (pentafluorophenyl)pyrrolylborate dimethylsilanediyl (2-methyl-5-thiapentalene)(2-methyl-4-(4'-ethylphenylindenyl)methylzirconiummethylbis (pentafluorophenyl)pyrrolylborate dimethylsilanediyl (2-methyl-6-thiapentalene)(2-methyl-4-(4'-ethylphenylindenyl)methylzirconiummethylbis (pentafluorophenyl)pyrrolylborate dimethylsilanediyl (2,5-dimethyl-4-thiapentalene)(2-methyl-4-(4'-ethylphenylindenyl)methylzirconiummethylbis (pentafluorophenyl)pyrrolylborate dimethylsilanediyl (2,5-dimethyl-6-thiapentalene)(2-methyl-4-(4'-ethylphenylindenyl)methylzirconiummethylbis (pentafluorophenyl)pyrrolylborate dimethylsilanediyl (2-methyl-4-oxapentalene)(2-methyl-4-(4'-ethylphenylindenyl)methylzirconiummethylbis (pentafluorophenyl)pyrrolylborate dimethylsilanediyl (2-methyl-5-oxapentalene)(2-methyl-4-(4'-ethylphenylindenyl)methylzirconiummethylbis (pentafluorophenyl)pyrrolylborate dimethylsilanediyl (2-methyl-6-oxapentalene)(2-methyl-4-(4'-ethylphenylindenyl)methylzirconiummethylbis (pentafluorophenyl)pyrrolylborate dimethylsilanediyl (2,5-dimethyl-4-oxapentalene)(2-methyl-4-(4'-ethylphenylindenyl)methylzirconiummethylbis (pentafluorophenyl)pyrrolylborate dimethylsilanediyl (2,5-dimethyl-6-oxapentalene)(2-methyl-4-(4'-ethylphenylindenyl)methylzirconiummethylbis (pentafluorophenyl)pyrrolylborate dimethylsilanediyl (2-methyl-4-azapentalene)(2-methyl-4-(4'-n-propylphenylindenyl)methylzirconiummethylbis (pentafluorophenyl)pyrrolylborate dimethylsilanediyl (2-methyl-5-azapentalene)(2-methyl-4-(4'-n-propylphenylindenyl)methylzirconiummethylbis (pentafluorophenyl)pyrrolylborate dimethylsilanediyl (2-methyl-6-azapentalene)(2-methyl-4-(4'-n-propylphenylindenyl)methylzirconiummethylbis (pentafluorophenyl)pyrrolylborate dimethylsilanediyl (2-methyl-N-phenyl-4-azapentalene)(2-methyl-4-(4'-n-propylphenylindenyl)methylzirconiummethylbis (pentafluorophenyl)pyrrolylborate dimethylsilanediyl (2-methyl-N-phenyl-5-azapentalene)(2-methyl-4-(4'-n-propylphenylindenyl)methylzirconiummethylbis (pentafluorophenyl)pyrrolylborate dimethylsilanediyl (2-methyl-N-phenyl-6-azapentalene)(2-methyl-4-(4'-n-propylphenylindenyl)methylzirconiummethylbis (pentafluorophenyl)pyrrolylborate dimethylsilanediyl (2,5-dimethyl-4-azapentalene)(2-methyl-4-(4'-n-propylphenylindenyl)methylzirconiummethylbis (pentafluorophenyl)pyrrolylborate dimethylsilanediyl (2,5-dimethyl-6-azapentalene)(2-methyl-4-(4'-n-propylphenylindenyl)methylzirconiummethylbis (pentafluorophenyl)pyrrolylborate dimethylsilanediyl (2,5-dimethyl-N-phenyl-4-azapentalene)(2-methyl-4-(4'-n-propylphenylindenyl)methylzirconiummethylbis (pentafluorophenyl)pyrrolylborate dimethylsilanediyl (2,5-dimethyl-N-phenyl-6-azapentalene)(2-methyl-4-(4'-n-propylphenylindenyl)methylzirconiummethylbis (pentafluorophenyl)pyrrolylborate dimethylsilanediyl (2-methyl-4-thiapentalene)(2-methyl-4-(4'-n-propylphenylindenyl)methylzirconiummethylbis (pentafluorophenyl)pyrrolylborate dimethylsilanediyl (2-methyl-5-thiapentalene)(2-methyl-4-(4'-n-propylphenylindenyl)methylzirconiummethylbis (pentafluorophenyl)pyrrolylborate dimethylsilanediyl (2-methyl-6-thiapentalene)(2-methyl-4-(4'n-propylphenylindenyl)methylzirconiummethylbis (pentafluorophenyl)pyrrolylborate dimethylsilanediyl (2,5-dimethyl-4-thiapentalene)(2-methyl-4-(4'-n-propylphenylindenyl)methylzirconiummethylbis (pentafluorophenyl)pyrrolylborate dimethylsilanediyl (2,5-dimethyl-6-thiapentalene)(2-methyl-4-(4'-n- propylphenylindenyl)methylzirconiummethylbis(pentafluorophenyl)pyrrolylborate dimethylsilanediyl(2-methyl-4-oxapentalene)(2-methyl-4-(4'-n-propylphenylindenyl)methylzirconiummethylbis(pentafluorophenyl)pyrrolylborate dimethylsilanediyl(2-methyl-5-oxapentalene)(2-methyl-4-(4'-n-propylphenylindenyl)methylzirconiummethylbis(pentafluorophenyl)pyrrolylborate dimethylsilanediyl(2-methyl-6-oxapentalene)(2-methyl-4-(4'-n-propylphenylindenyl)methylzirconiummethylbis(pentafluorophenyl)pyrrolylborate dimethylsilanediyl(2,5-dimethyl-4-oxapentalene)(2-methyl-4-(4'-n-propylphenylindenyl)methylzirconiummethylbis(pentafluorophenyl)pyrrolylborate dimethylsilanediyl(2,5-dimethyl-6-oxapentalene)(2-methyl-4-(4'-n-propylphenylindenyl)methylzirconiummethylbis(pentafluorophenyl)pyrrolylborate dimethylsilanediyl(2-methyl-4-azapentalene)(2-methyl-4-(4'-iso-propylphenylindenyl)methylzirconiummethylbis(pentafluorophenyl)pyrrolylborate dimethylsilanediyl(2-methyl-5-azapentalene)(2-methyl-4-(4'-iso-propylphenylindenyl)methylzirconiummethylbis(pentafluorophenyl)pyrrolylborate dimethylsilanediyl(2-methyl-6-azapentalene)(2-methyl-4-(4'-iso-propylphenylindenyl)methylzirconiummethylbis(pentafluorophenyl)pyrrolylborate dimethylsilanediyl(2-methyl-N-phenyl-4-azapentalene)(2-methyl-4-(4'-isopropylphenylindenyl)methylzirconiummethylbis(pentafluorophenyl)pyrrolylborate dimethylsilanediyl(2-methyl-N-phenyl-5-azapentalene)(2-methyl-4-(4'-isopropylphenylindenyl)methylzirconiummethylbis(pentafluorophenyl)pyrrolylborate dimethylsilanediyl(2-methyl-N-phenyl-6-azapentalene)(2-methyl-4-(4'-isopropylphenylindenyl)methylzirconiummethylbis(pentafluorophenyl)pyrrolylborate dimethylsilanediyl(2,5-dimethyl-4-azapentalene)(2-methyl-4-(4'-isopropylphenylindenyl)methylzirconiummethylbis(pentafluorophenyl)pyrrolylborate dimethylsilanediyl(2,5-dimethyl-6-azapentalene)(2-methyl-4-(4'-isopropylphenylindenyl)methylzirconiummethylbis(pentafluorophenyl)pyrrolylborate dimethylsilanediyl(2,5-dimethyl-N-phenyl-4-azapentalene)(2-methyl-4-(4'-isopropylphenylindenyl)methylzirconiummethylbis(pentafluorophenyl)pyrrolylborate dimethylsilanediyl(2,5-dimethyl-N-phenyl-6-azapentalene)(2-methyl-4-(4'-isopropylphenylindenyl)methylzirconiummethylbis(pentafluorophenyl)pyrrolylborate dimethylsilanediyl(2-methyl-4-thiapentalene)(2-methyl-4-(4'-isopropylphenylindenyl)methylzirconiummethylbis(pentafluorophenyl)pyrrolylborate dimethylsilanediyl(2-methyl-5-thiapentalene)(2-methyl-4-(4'-isopropylphenylindenyl)methylzirconiummethylbis(pentafluorophenyl)pyrrolylborate dimethylsilanediyl(2-methyl-6-thiapentalene)(2-methyl-4-(4'-isopropylphenylindenyl)methylzirconiummethylbis(pentafluorophenyl)pyrrolylborate dimethylsilanediyl(2,5-dimethyl-4-thiapentalene)(2-methyl-4-(4'-isopropylphenylindenyl)methylzirconiummethylbis(pentafluorophenyl)pyrrolylborate dimethylsilanediyl(2,5-dimethyl-6-thiapentalene)(2-methyl-4-(4'-isopropylphenylindenyl)methylzirconiummethylbis(pentafluorophenyl)pyrrolylborate dimethylsilanediyl(2-methyl-4-oxapentalene)(2-methyl-4-(4'-isopropylphenylindenyl)methylzirconiummethylbis(pentafluorophenyl)pyrrolylborate dimethylsilanediyl(2-methyl-5-oxapentalene)(2-methyl-4-(4'-iso-propylphenylindenyl)methylzirconiummethylbis(pentafluorophenyl)pyrrolylborate dimethylsilanediyl(2-methyl-6-oxapentalene)(2-methyl-4-(4'-iso-propylphenylindenyl)methylzirconiummethylbis(pentafluorophenyl)pyrrolylborate dimethylsilanediyl(2,5-dimethyl-4-oxapentalene)(2-methyl-4-(4'-isopropylphenylindenyl)methylzirconiummethylbis(pentafluorophenyl)pyrrolylborate dimethylsilanediyl(2,5-dimethyl-6-oxapentalene)(2-methyl-4-(4'-isopropylphenylindenyl)methylzirconiummethylbis(pentafluorophenyl)pyrrolylborate dimethylsilanediyl(2-methyl-4-azapentalene)(2-methyl-4-(4'-n-butylphenylindenyl)methylzirconiummethylbis(pentafluorophenyl)pyrrolylborate dimethylsilanediyl(2-methyl-5-azapentalene)(2-methyl-4-(4'n-butylphenylindenyl)methylzirconiummethylbis(pentafluorophenyl)pyrrolylborate dimethylsilanediyl(2-methyl-6-azapentalene)(2-methyl-4-(4'-n-butylphenylindenyl)methylzirconiummethylbis(pentafluorophenyl)pyrrolylborate dimethylsilanediyl(2-methyl-N-phenyl-4-azapentalene)(2-methyl-4-(4'-n-butylphenylindenyl)methylzirconiummethylbis(pentafluorophenyl)pyrrolylborate dimethylsilanediyl(2-methyl-N-phenyl-5-azapentalene)(2-methyl-4-(4'-n-butylphenylindenyl)methylzirconiummethylbis(pentafluorophenyl)pyrrolylborate dimethylsilanediyl(2-methyl-N-phenyl-6-azapentalene)(2-methyl-4-(4'-n-butylphenylindenyl)methylzirconiummethylbis(pentafluorophenyl)pyrrolylborate dimethylsilanediyl(2,5-dimethyl-4-azapentalene)(2-methyl-4-(4'-n-butylphenylindenyl)methylzirconiummethylbis(pentafluorophenyl)pyrrolylborate dimethylsilanediyl(2,5-dimethyl-6-azapentalene)(2-methyl-4-(4'n-butylphenylindenyl)methylzirconiummethylbis(pentafluorophenyl)pyrrolylborate dimethylsilanediyl(2,5-dimethyl-N-phenyl-4-azapentalene)(2-methyl-4-(4'-n-butylphenylindenyl)methylzirconiummethylbis(pentafluorophenyl)pyrrolylborate dimethylsilanediyl(2,5-dimethyl-N-phenyl-6-azapentalene)(2-methyl-4-(4'-n-butylphenylindenyl)methylzirconiummethylbis(pentafluorophenyl)pyrrolylborate dimethylsilanediyl(2-methyl-4-thiapentalene)(2-methyl-4-(4'-n-butylphenylindenyl)methylzirconiummethylbis(pentafluorophenyl)pyrrolylborate dimethylsilanediyl(2-methyl-5-thiapentalene)(2-methyl-4-(4'-n-butylphenylindenyl)methylzirconiummethylbis(pentafluorophenyl)pyrrolylborate dimethylsilanediyl(2-methyl-6-thiapentalene)(2-methyl-4-(4'-n-butylphenylindenyl)methylzirconiummethylbis(pentafluorophenyl)pyrrolylborate dimethylsilanediyl(2,5-dimethyl-4-thiapentalene)(2-methyl-4-(4'-n-butylphenylindenyl)methylzirconiummethylbis(pentafluorophenyl)pyrrolylborate dimethylsilanediyl(2,5-dimethyl-6-thiapentalene)(2-methyl-4-(4'-n-butylphenylindenyl)methylzirconiummethylbis(pentafluorophenyl)pyrrolylborate dimethylsilanediyl(2-methyl-4-oxapentalene)(2-methyl-4-(4'-n-butylphenylindenyl)methylzirconiummethylbis(pentafluorophenyl)pyrrolylborate dimethylsilanediyl(2-methyl-5-oxapentalene)(2-methyl-4-(4'-n-butylphenylindenyl)methylzirconiummethylbis(pentafluorophenyl)pyrrolylborate dimethylsilanediyl(2-methyl-6-oxapentalene)(2-methyl-4-(4'-n-butylphenylindenyl)methylzirconiummethylbis(pentafluorophenyl)pyrrolylborate dimethylsilanediyl(2,5-dimethyl-4-oxapentalene)(2-methyl-4-(4'-n-butylphenylindenyl)methylzirconiummethylbis(pentafluorophenyl)pyrrolylborate dimethylsilanediyl (2,5-dimethyl-6-oxapentalene)(2-methyl-4-(4'-n-butylphenylindenyl)methylzirconiummethylbis(pentafluorophenyl)pyrrolylborate dimethylsilanediyl(2-methyl-4-azapentalene)(2-methyl-4-(4'-s-butylphenylindenyl)methylzirconiummethylbis(pentafluorophenyl)pyrrolylborate dimethylsilanediyl(2-methyl-5-azapentalene)(2-methyl-4-(4'-s-butylphenylindenyl)methylzirconiummethylbis(pentafluorophenyl)pyrrolylborate dimethylsilanediyl(2-methyl-6-azapentalene)(2-methyl-4-(4'-s-butylphenylindenyl)methylzirconiummethylbis(pentafluorophenyl)pyrrolylborate dimethylsilanediyl(2-methyl-N-phenyl-4-azapentalene)(2-methyl-4-(4'-s-butylphenylindenyl)methylzirconiummethylbis(pentafluorophenyl)pyrrolylborate dimethylsilanediyl(2-methyl-N-phenyl-5-azapentalene)(2-methyl-4-(4'-s-butylphenylindenyl)methylzirconiummethylbis(pentafluorophenyl)pyrrolylborate dimethylsilanediyl(2-methyl-N-phenyl-6-azapentalene)(2-methyl-4-(4'-s-butylphenylindenyl)methylzirconiummethylbis(pentafluorophenyl)pyrrolylborate dimethylsilanediyl(2,5-dimethyl-4-azapentalene)(2-methyl-4-(4'-s-butylphenylindenyl)methylzirconiummethylbis(pentafluorophenyl)pyrrolylborate dimethylsilanediyl(2,5-dimethyl-6-azapentalene)(2-methyl-4-(4'-s-butylphenylindenyl)methylzirconiummethylbis(pentafluorophenyl)pyrrolylborate dimethylsilanediyl(2,5-dimethyl-N-phenyl-4-azapentalene)(2-methyl-4-(4'-s-butylphenylindenyl)methylzirconiummethylbis(pentafluorophenyl)pyrrolylborate dimethylsilanediyl(2,5-dimethyl-N-phenyl-6-azapentalene)(2-methyl-4-(4'-s-butylphenylindenyl)methylzirconiummethylbis(pentafluorophenyl)pyrrolylborate dimethylsilanediyl(2-methyl-4-thiapentalene)(2-methyl-4-(4'-s-butylphenylindenyl)methylzirconiummethylbis(pentafluorophenyl)pyrrolylborate dimethylsilanediyl(2-methyl-5-thiapentalene)(2-methyl-4-(4'-s-butylphenylindenyl)methylzirconiummethylbis(pentafluorophenyl)pyrrolylborate dimethylsilanediyl(2-methyl-6-thiapentalene)(2-methyl-4-(4'-s-butylphenylindenyl)methylzirconiummethylbis(pentafluorophenyl)pyrrolylborate dimethylsilanediyl(2,5-dimethyl-4-thiapentalene)(2-methyl-4-(4'-s-butylphenylindenyl)methylzirconiummethylbis(pentafluorophenyl)pyrrolylborate dimethylsilanediyl(2,5-dimethyl-6-thiapentalene)(2-methyl-4-(4'-s-butylphenylindenyl)methylzirconiummethylbis(pentafluorophenyl)pyrrolylborate dimethylsilanediyl(2-methyl-4-oxapentalene)(2-methyl-4-(4'-s-butylphenylindenyl)methylzirconiummethylbis(pentafluorophenyl)pyrrolylborate dimethylsilanediyl(2-methyl-5-oxapentalene)(2-methyl-4-(4'-s-butylphenylindenyl)methylzirconiummethylbis(pentafluorophenyl)pyrrolylborate dimethylsilanediyl(2-methyl-6-oxapentalene)(2-methyl-4-(4'-s-butylphenylindenyl)methylzirconiummethylbis(pentafluorophenyl)pyrrolylborate dimethylsilanediyl(2,5-dimethyl-4-oxapentalene)(2-methyl-4-(4'-s-butylphenylindenyl)methylzirconiummethylbis(pentafluorophenyl)pyrrolylborate dimethylsilanediyl(2,5-dimethyl-6-oxapentalene)(2-methyl-4-(4'-s-butylphenylindenyl)methylzirconiummethylbis(pentafluorophenyl)pyrrolylborate dimethylsilanediyl(2-methyl-4-azapentalene)(2-methyl-4-(4'-tert-butylphenylindenyl)methylzirconiummethylbis(pentafluorophenyl)pyrrolylborate dimethylsilanediyl(2-methyl-5-azapentalene)(2-methyl-4-(4'-tert-butylphenylindenyl)methylzirconiummethylbis(pentafluorophenyl)pyrrolylborate dimethylsilanediyl(2-methyl-6-azapentalene)(2-methyl-4-(4'-tert-butylphenylindenyl)methylzirconiummethylbis(pentafluorophenyl)pyrrolylborate dimethylsilanediyl(2-methyl-N-phenyl-4-azapentalene)(2-methyl-4-(4'-tert-butylphenylindenyl)methylzirconiummethylbis(pentafluorophenyl)pyrrolylborate dimethylsilanediyl(2-methyl-N-phenyl-5-azapentalene)(2-methyl-4-(4'-tert-butylphenylindenyl)methylzirconiummethylbis(pentafluorophenyl)pyrrolylborate dimethylsilanediyl(2-methyl-N-phenyl-6-azapentalene)(2-methyl-4-(4'-tert-butylphenylindenyl)methylzirconiummethylbis(pentafluorophenyl)pyrrolylborate dimethylsilanediyl(2,5-dimethyl-4-azapentalene)(2-methyl-4-(4'-tert-butylphenylindenyl)methylzirconiummethylbis(pentafluorophenyl)pyrrolylborate dimethylsilanediyl(2,5-dimethyl-6-azapentalene)(2-methyl-4-(4'-tert-butylphenylindenyl)methylzirconiummethylbis(pentafluorophenyl)pyrrolylborate dimethylsilanediyl(2,5-dimethyl-N-phenyl-4-azapentalene)(2-methyl-4-(4'-tert-butylphenylindenyl)methylzirconiummethylbis(pentafluorophenyl)pyrrolylborate dimethylsilanediyl(2,5-dimethyl-N-phenyl-6-azapentalene)(2-methyl-4-(4'-tert-butylphenylindenyl)methylzirconiummethylbis(pentafluorophenyl)pyrrolylborate dimethylsilanediyl(2-methyl-4-thiapentalene)(2-methyl-4-(4'-tert-butylphenylindenyl)methylzirconiummethylbis(pentafluorophenyl)pyrrolylborate dimethylsilanediyl(2-methyl-5-thiapentalene)(2-methyl-4-(4'-tert-butylphenylindenyl)methylzirconiummethylbis(pentafluorophenyl)pyrrolylborate dimethylsilanediyl(2-methyl-6-thiapentalene)(2-methyl-4-(4'-tert-butylphenylindenyl)methylzirconiummethylbis(pentafluorophenyl)pyrrolylborate dimethylsilanediyl(2,5-dimethyl-4-thiapentalene)(2-methyl-4-(4'-tert-butylphenylindenyl)methylzirconiummethylbis(pentafluorophenyl)pyrrolylborate dimethylsilanediyl(2,5-dimethyl-6-thiapentalene)(2-methyl-4-(4'-tert-butylphenylindenyl)methylzirconiummethylbis(pentafluorophenyl)pyrrolylborate dimethylsilanediyl(2-methyl-4-oxapentalene)(2-methyl-4-(4'-tert-butylphenylindenyl)methylzirconiummethylbis(pentafluorophenyl)pyrrolylborate dimethylsilanediyl(2-methyl-5-oxapentalene)(2-methyl-4-(4'-tert-butylphenylindenyl)methylzirconiummethylbis(pentafluorophenyl)pyrrolylborate dimethylsilanediyl(2-methyl-6-oxapentalene)(2-methyl-4-(4'-tert-butylphenylindenyl)methylzirconiummethylbis(pentafluorophenyl)pyrrolylborate dimethylsilanediyl(2,5-dimethyl-4-oxapentalene)(2-methyl-4-(4'-tert-butylphenylindenyl)methylzirconiummethylbis(pentafluorophenyl)pyrrolylborate dimethylsilanediyl(2,5-dimethyl-6-oxapentalene)(2-methyl-4-(4'-tert-butylphenylindenyl)methylzirconiummethylbis(pentafluorophenyl)pyrrolylborate dimethylsilanediyl(2-methyl-4-azapentalene)(2-methyl-4-(4'-n-pentylphenylindenyl)methylzirconiummethylbis(pentafluorophenyl)pyrrolylborate dimethylsilanediyl(2-methyl-5-azapentalene)(2-methyl-4-(4'-n-pentylphenylindenyl)methylzirconiummethylbis(pentafluorophenyl)pyrrolylborate dimethylsilanediyl(2-methyl-6-azapentalene)(2-methyl-4-(4'-n-pentylphenylindenyl)methylzirconiummethylbis(pentafluorophenyl)pyrrolylborate dimethylsilanediyl(2-methyl-N-phenyl-4-azapentalene)(2-methyl-4-(4'-n-pentylphenylindenyl)methylzirconiummethylbis (pentafluorophenyl)pyrrolylborate dimethylsilanediyl (2-methyl-N-phenyl-5-azapentalene)(2-methyl-4-(4'-n-pentylphenylindenyl)methylzirconiummethylbis(pentafluorophenyl)pyrrolylborate dimethylsilanediyl (2-methyl-N-phenyl-6-azapentalene)(2-methyl-4-(4'-n-pentylphenylindenyl)methylzirconiummethylbis(pentafluorophenyl)pyrrolylborate dimethylsilanediyl (2,5-dimethyl-4-azapentalene)(2-methyl-4-(4'-n-pentylphenylindenyl)methylzirconiummethylbis(pentafluorophenyl)pyrrolylborate dimethylsilanediyl (2,5-dimethyl-6-azapentalene)(2-methyl-4-(4'-n-pentylphenylindenyl)methylzirconiummethylbis(pentafluorophenyl)pyrrolylborate dimethylsilanediyl (2,5-dimethyl-N-phenyl-4-azapentalene)(2-methyl-4-(4'-n-pentylphenylindenyl)methylzirconiummethylbis-(pentafluorophenyl)pyrrolylborate dimethylsilanediyl (2,5-dimethyl-N-phenyl-6-azapentalene)(2-methyl-4-(4'-n-pentylphenylindenyl)methylzirconiummethylbis(pentafluorophenyl)pyrrolylborate dimethylsilanediyl (2-methyl-4-thiapentalene)(2-methyl-4-(4'-n-pentylphenylindenyl)methylzirconiummethylbis(pentafluorophenyl)pyrrolylborate dimethylsilanediyl (2-methyl-5-thiapentalene)(2-methyl-4-(4'-n-pentylphenylindenyl)methylzirconiummethylbis(pentafluorophenyl)pyrrolylborate dimethylsilanediyl (2-methyl-6-thiapentalene)(2-methyl-4-(4'-n-pentylphenylindenyl)methylzirconiummethylbis(pentafluorophenyl)pyrrolylborate dimethylsilanediyl (2,5-dimethyl-4-thiapentalene)(2-methyl-4-(4'-n-pentylphenylindenyl)methylzirconiummethylbis(pentafluorophenyl)pyrrolylborate dimethylsilanediyl (2,5-dimethyl-6-thiapentalene)(2-methyl-4-(4'-n-pentylphenylindenyl)methylzirconiummethylbis(pentafluorophenyl)pyrrolylborate dimethylsilanediyl (2-methyl-4-oxapentalene)(2-methyl-4-(4'-n-pentylphenylindenyl)methylzirconiummethylbis(pentafluorophenyl)pyrrolylborate dimethylsilanediyl (2-methyl-5-oxapentalene)(2-methyl-4-(4'-n-pentylphenylindenyl)methylzirconiummethylbis(pentafluorophenyl)pyrrolylborate dimethylsilanediyl (2-methyl-6-oxapentalene)(2-methyl-4-(4'-n-pentylphenylindenyl)methylzirconiummethylbis(pentafluorophenyl)pyrrolylborate dimethylsilanediyl (2,5-dimethyl-4-oxapentalene)(2-methyl-4-(4'-n-pentylphenylindenyl)methylzirconiummethylbis(pentafluorophenyl)pyrrolylborate dimethylsilanediyl (2,5-dimethyl-6-oxapentalene)(2-methyl-4-(4'-n-pentylphenylindenyl)methylzirconiummethylbis(pentafluorophenyl)pyrrolylborate dimethylsilanediyl (2-methyl-4-azapentalene)(2-methyl-4-(4'-n-hexylphenylindenyl)methylzirconiummethylbis(pentafluorophenyl)pyrrolylborate dimethylsilanediyl (2-methyl-5-azapentalene)(2-methyl-4-(4'-n-hexylphenylindenyl)methylzirconiummethylbis(pentafluorophenyl)pyrrolylborate dimethylsilanediyl (2-methyl-6-azapentalene)(2-methyl-4-(4'-n-hexylphenylindenyl)methylzirconiummethylbis(pentafluorophenyl)pyrrolylborate dimethylsilanediyl (2-methyl-N-phenyl-4-azapentalene)(2-methyl-4-(4'-n-hexylphenylindenyl)methylzirconiummethylbis(pentafluorophenyl)pyrrolylborate dimethylsilanediyl (2-methyl-N-phenyl-5-azapentalene)(2-methyl-4-(4'-n-hexylphenylindenyl)methylzirconiummethylbis(pentafluorophenyl)pyrrolylborate dimethylsilanediyl (2-methyl-N-phenyl-6-azapentalene)(2-methyl-4-(4'-n-hexylphenylindenyl)methylzirconiummethylbis(pentafluorophenyl)pyrrolylborate dimethylsilanediyl (2,5-dimethyl-4-azapentalene)(2-methyl-4-(4'-n-hexylphenylindenyl)methylzirconiummethylbis(pentafluorophenyl)pyrrolylborate dimethylsilanediyl (2,5-dimethyl-6-azapentalene)(2-methyl-4-(4'-n-hexylphenylindenyl)methylzirconiummethylbis(pentafluorophenyl)pyrrolylborate dimethylsilanediyl (2,5-dimethyl-N-phenyl-4-azapentalene)(2-methyl-4-(4'-n-hexylphenylindenyl)methylzirconiummethylbis(pentafluorophenyl)pyrrolylborate dimethylsilanediyl (2,5-dimethyl-N-phenyl-6-azapentalene)(2-methyl-4-(4'-n-hexylphenylindenyl)methylzirconiummethylbis(pentafluorophenyl)pyrrolylborate dimethylsilanediyl (2-methyl-4-thiapentalene)(2-methyl-4-(4'-n-hexylphenylindenyl)methylzirconiummethylbis(pentafluorophenyl)pyrrolylborate dimethylsilanediyl (2-methyl-5-thiapentalene)(2-methyl-4-(4'-n-hexylphenylindenyl)methylzirconiummethylbis(pentafluorophenyl)pyrrolylborate dimethylsilanediyl (2-methyl-6-thiapentalene)(2-methyl-4-(4'-n-hexylphenylindenyl)methylzirconiummethylbis(pentafluorophenyl)pyrrolylborate dimethylsilanediyl (2,5-dimethyl-4-thiapentalene)(2-methyl-4-(4'-n-hexylphenylindenyl)methylzirconiummethylbis(pentafluorophenyl)pyrrolylborate dimethylsilanediyl (2,5-dimethyl-6-thiapentalene)(2-methyl-4-(4'-n-hexylphenylindenyl)methylzirconiummethylbis(pentafluorophenyl)pyrrolylborate dimethylsilanediyl(, 2-methyl-4-oxapentalene)(2-methyl-4-(4'-n-hexylphenylindenyl)methylzirconiummethylbis(pentafluorophenyl)pyrrolylborate dimethylsilanediyl (2-methyl-5-oxapentalene)(2-methyl-4-(4'-n-hexylphenylindenyl)methylzirconiummethylbis(pentafluorophenyl)pyrrolylborate dimethylsilanediyl (2-methyl-6-oxapentalene)(2-methyl-4-(4'-n-hexylphenylindenyl)methylzirconiummethylbis(pentafluorophenyl)pyrrolylborate dimethylsilanediyl (2,5-dimethyl-4-oxapentalene)(2-methyl-4-(4'-n-hexylphenylindenyl)methylzirconiummethylbis(pentafluorophenyl)pyrrolylborate dimethylsilanediyl (2,5-dimethyl-6-oxapentalene)(2-methyl-4-(4'-n-hexylphenylindenyl)methylzirconiummethylbis(pentafluorophenyl)pyrrolylborate dimethylsilanediyl (2-methyl-4-azapentalene)(2-methyl-4-(4'-cyclohexylphenylindenyl)methylzirconiummethylbis(pentafluorophenyl)pyrrolylborate dimethylsilanediyl (2-methyl-5-azapentalene)(2-methyl-4-(4'-cyclohexylphenylindenyl)methylzirconiummethylbis(pentafluorophenyl)pyrrolylborate dimethylsilanediyl (2-methyl-6-azapentalene)(2-methyl-4-(4'-cyclohexylphenylindenyl)methylzirconiummethylbis(pentafluorophenyl)pyrrolylborate dimethylsilanediyl (2-methyl-N-phenyl-4-azapentalene)(2-methyl-4-(4'-cyclohexylphenylindenyl)methylzirconiummethylbis(pentafluorophenyl)pyrrolylborate dimethylsilanediyl (2-methyl-N-phenyl-5-azapentalene)(2-methyl-4-(4'-cyclohexylphenylindenyl)methylzirconiummethylbis(pentafluorophenyl)pyrrolylborate dimethylsilanediyl (2-methyl-N-phenyl-6-azapentalene)(2-methyl-4-(4'-cyclohexylphenylindenyl)methylzirconiummethylbis(pentafluorophenyl)pyrrolylborate dimethylsilanediyl (2,5-dimethyl-4-azapentalene)(2-methyl-4-(4'-cyclohexylphenylindenyl)methylzirconiummethylbis(pentafluorophenyl)pyrrolylborate dimethylsilanediyl (2,5-dimethyl-6-azapentalene)(2-methyl-4-(4'-cyclohexylphenylindenyl)methylzirconiummethylbis(pentafluorophenyl)pyrrolylborate dimethylsilanediyl (2,5-dimethyl-N-phenyl-4-azapentalene)(2-methyl-4-

(4'-cyclohexylphenylindenyl)methylzirconiummethylbis(pentafluorophenyl)pyrrolylborate dimethylsilanediyl(2,5-dimethyl-N-phenyl-6-azapentalene)(2-methyl-4-(4'-cyclohexylphenylindenyl)methylzirconiummethylbis(pentafluorophenyl)pyrrolylborate dimethylsilanediyl(2-methyl-4-thiapentalene)(2-methyl-4-(4'-cyclohexylphenylindenyl)methylzirconiummethylbis(pentafluorophenyl)pyrrolylborate dimethylsilanediyl(2-methyl-5-thiapentalene)(2-methyl-4-(4'-cyclohexylphenylindenyl)methylzirconiummethylbis(pentafluorophenyl)pyrrolylborate dimethylsilanediyl(2-methyl-6-thiapentalene)(2-methyl-4-(4'-cyclohexylphenylindenyl)methylzirconiummethylbis(pentafluorophenyl)pyrrolylborate dimethylsilanediyl(2,5-dimethyl-4-thiapentalene)(2-methyl-4-(4'-cyclohexylphenylindenyl)methylzirconiummethylbis(pentafluorophenyl)pyrrolylborate dimethylsilanediyl(2,5-dimethyl-6-thiapentalene)(2-methyl-4-(4'-cyclohexylphenylindenyl)methylzirconiummethylbis(pentafluorophenyl)pyrrolylborate dimethylsilanediyl(2-methyl-4-oxapentalene)(2-methyl-4-(4'-cyclohexylphenylindenyl)methylzirconiummethylbis(pentafluorophenyl)pyrrolylborate dimethylsilanediyl(2-methyl-5-oxapentalene)(2-methyl-4-(4'-cyclohexylphenylindenyl)methylzirconiummethylbis(pentafluorophenyl)pyrrolylborate dimethylsilanediyl(2-methyl-6-oxapentalene)(2-methyl-4-(4'-cyclohexylphenylindenyl)methylzirconiummethylbis(pentafluorophenyl)pyrrolylborate dimethylsilanediyl(2,5-dimethyl-4-oxapentalene)(2-methyl-4-(4'-cyclohexylphenylindenyl)methylzirconiummethylbis(pentafluorophenyl)pyrrolylborate dimethylsilanediyl(2,5-dimethyl-6-oxapentalene)(2-methyl-4-(4'-cyclohexylphenylindenyl)methylzirconiummethylbis(pentafluorophenyl)pyrrolylborate dimethylsilanediyl(2-methyl-4-azapentalene)(2-methyl-4-(4'-trimethylsilylphenylindenyl)methylzirconiummethylbis(pentafluorophenyl)pyrrolylborate dimethylsilanediyl(2-methyl-5-azapentalene)(2-methyl-4-(4'-trimethylsilylphenylindenyl)methylzirconiummethylbis(pentafluorophenyl)pyrrolylborate dimethylsilanediyl(2-methyl-6-azapentalene)(2-methyl-4-(4'-trimethylsilylphenylindenyl)methylzirconiummethylbis(pentafluorophenyl)pyrrolylborate dimethylsilanediyl(2-methyl-N-phenyl-4-azapentalene)(2-methyl-4-(4'-trimethylsilylphenylindenyl)methylzirconiummethylbis(pentafluorophenyl)pyrrolylborate dimethylsilanediyl(2-methyl-N-phenyl-5-azapentalene)(2-methyl-4-(4'-trimethylsilylphenylindenyl)methylzirconiummethylbis(pentafluorophenyl)pyrrolylborate dimethylsilanediyl(2-methyl-N-phenyl-6-azapentalene)(2-methyl-4-(4'-trimethylsilylphenylindenyl)methylzirconiummethylbis(pentafluorophenyl)pyrrolylborate dimethylsilanediyl(2,5-dimethyl-4-azapentalene)(2-methyl-4-(4'-trimethylsilylphenylindenyl)methylzirconiummethylbis(pentafluorophenyl)pyrrolylborate dimethylsilanediyl(2,5-dimethyl-6-azapentalene)(2-methyl-4-(4'-trimethylsilylphenylindenyl)methylzirconiummethylbis(pentafluorophenyl)pyrrolylborate dimethylsilanediyl(2,5-dimethyl-N-phenyl-4-azapentalene)(2-methyl-4-(4'-trimethylsilylphenylindenyl)methylzirconiummethylbis(pentafluorophenyl)pyrrolylborate dimethylsilanediyl(2,5-dimethyl-N-phenyl-6-azapentalene)(2-methyl-4-(4'-trimethylsilylphenylindenyl)methylzirconiummethylbis(pentafluorophenyl)pyrrolylborate dimethylsilanediyl(2-methyl-4-thiapentalene)(2-methyl-4-(4'-trimethylsilylphenylindenyl)methylzirconiummethylbis(pentafluorophenyl)pyrrolylborate dimethylsilanediyl(2-methyl-5-thiapentalene)(2-methyl-4-(4'-trimethylsilylphenylindenyl)methylzirconiummethylbis(pentafluorophenyl)pyrrolylborate dimethylsilanediyl(2-methyl-6-thiapentalene)(2-methyl-4-(4'-trimethylsilylphenylindenyl)methylzirconiummethylbis(pentafluorophenyl)pyrrolylborate dimethylsilanediyl(2,5-dimethyl-4-thiapentalene)(2-methyl-4-(4'-trimethylsilylphenylindenyl)methylzirconiummethylbis(pentafluorophenyl)pyrrolylborate dimethylsilanediyl(2,5-dimethyl-6-thiapentalene)(2-methyl-4-(4'-trimethylsilylphenylindenyl)methylzirconiummethylbis(pentafluorophenyl)pyrrolylborate dimethylsilanediyl(2-methyl-4-oxapentalene)(2-methyl-4-(4'-trimethylsilylphenylindenyl)methylzirconiummethylbis(pentafluorophenyl)pyrrolylborate dimethylsilanediyl(2-methyl-5-oxapentalene)(2-methyl-4-(4'-trimethylsilylphenylindenyl)methylzirconiummethylbis(pentafluorophenyl)pyrrolylborate dimethylsilanediyl(2-methyl-6-oxapentalene)(2-methyl-4-(4'-trimethylsilylphenylindenyl)methylzirconiummethylbis(pentafluorophenyl)pyrrolylborate dimethylsilanediyl(2,5-dimethyl-4-oxapentalene)(2-methyl-4-(4'-trimethylsilylphenylindenyl)methylzirconiummethylbis(pentafluorophenyl)pyrrolylborate dimethylsilanediyl(2,5-dimethyl-6-oxapentalene)(2-methyl-4-(4'-trimethylsilylphenylindenyl)methylzirconiummethylbis(pentafluorophenyl)pyrrolylborate dimethylsilanediyl(2-methyl-4-azapentalene)(2-methyl-4-(4'-adamantylphenylindenyl)methylzirconiummethylbis(pentafluorophenyl)pyrrolylborate dimethylsilanediyl(2-methyl-5-azapentalene)(2-methyl-4-(4'-adamantylphenylindenyl)methylzirconiummethylbis(pentafluorophenyl)pyrrolylborate dimethylsilanediyl(2-methyl-6-azapentalene)(2-methyl-4-(4'-adamantylphenylindenyl)methylzirconiummethylbis(pentafluorophenyl)pyrrolylborate dimethylsilanediyl(2-methyl-N-phenyl-4-azapentalene)(2-methyl-4-(4'-adamantylphenylindenyl)methylzirconiummethylbis(pentafluorophenyl)pyrrolylborate dimethylsilanediyl(2-methyl-N-phenyl-5-azapentalene)(2-methyl-4-(4'-adamantylphenylindenyl)methylzirconiummethylbis(pentafluorophenyl)pyrrolylborate dimethylsilanediyl(2-methyl-N-phenyl-6-azapentalene)(2-methyl-4-(4'-adamantylphenylindenyl)methylzirconiummethylbis(pentafluorophenyl)pyrrolylborate dimethylsilanediyl (2,5-dimethyl-4-azapentalene)(2-methyl-4-(4'-adamantylphenylindenyl)methylzirconiummethylbis(pentafluorophenyl)pyrrolylborate dimethylsilanediyl(2,5-dimethyl-6-azapentalene)(2-methyl-4-(4'-adamantylphenylindenyl)methylzirconiummethylbis(pentafluorophenyl)pyrrolylborate dimethylsilanediyl(2,5-dimethyl-4-azapentalene)(2-methyl-4-(4'-adamantylphenylindenyl)methylzirconiummethylbis(pentafluorophenyl)pyrrolylborate dimethylsilanediyl(2,5-dimethyl-N-phenyl-4-azapentalene)(2-methyl-4-(4'-adamantylphenylindenyl)methylzirconiummethylbis(pentafluorophenyl)pyrrolylborate dimethylsilanediyl(2,5-dimethyl-N-phenyl-6-azapentalene)(2-methyl-4-(4'-adamantylphenylindenyl)methylzirconiummethylbis(pentafluorophenyl)pyrrolylborate dimethylsilanediyl(2-methyl-4-thiapentalene)(2-methyl-4-(4'-adamantylphenylindenyl)methylzirconiummethylbis(pentafluorophenyl)pyrrolylborate dimethylsilanediyl(2-methyl-5-thiapentalene)(2-methyl-4-(4'-adamantylphenylindenyl)methylzirconiummethylbis(pentafluorophenyl)pyrrolylborate dimethylsilanediyl(2-methyl-6-thiapentalene)(2-methyl-4-(4'-adamantylphenylindenyl)methylzirconiummethylbis(pentafluorophenyl)pyrrolylborate dimethylsilanediyl(2,5-dimethyl-4-thiapentalene)(2-methyl-4-(4'-adamantylphenylindenyl)methylzirconiummethylbis(pentafluorophenyl)pyrrolylborate dimethylsilanediyl(2,5-dimethyl-6-thiapentalene)(2-methyl-4-(4'-adamantylphenylindenyl)methylzirconiummethylbis(pentafluorophenyl)pyrrolylborate dimethylsilanediyl(2-methyl-4-oxapentalene)(2-methyl-4-(4'-adamantylphenylindenyl)methylzirconiummethylbis(pentafluorophenyl)pyrrolylborate dimethylsilanediyl(2-methyl-5-oxapentalene)(2-methyl-4-(4'-adamantylphenylindenyl)methylzirconiummethylbis(pentafluorophenyl)pyrrolylborate dimethylsilanediyl(2-methyl-6-oxapentalene)(2-methyl-4-(4'-adamantylphenylindenyl)methylzirconiummethylbis(pentafluorophenyl)pyrrolylborate dimethylsilanediyl(2,5-dimethyl-4-oxapentalene)(2-methyl-4-(4'-adamantylphenylindenyl)methylzirconiummethylbis(pentafluorophenyl)pyrrolylborate dimethylsilanediyl(2,5-dimethyl-6-oxapentalene)(2-methyl-4-(4'-adamantylphenylindenyl)methylzirconiummethylbis(pentafluorophenyl)pyrrolylborate dimethylsilanediyl(2-methyl-4-azapentalene)(2-methyl-4-(4'-tris(trifluoromethyl)methylphenylindenyl)methylzirconiummethylbis(pentafluorophenyl)pyrrolylborate dimethylsilanediyl(2-methyl-5-azapentalene)(2-methyl-4-(4'-tris(trifluoromethyl)methylphenylindenyl)methylzirconiummethylbis(pentafluorophenyl)pyrrolylborate dimethylsilanediyl(2-methyl-6-azapentalene)(2-methyl-4-(4'-tris(trifluoromethyl)methylphenylindenyl)methylzirconiummethylbis(pentafluorophenyl)pyrrolylborate dimethylsilanediyl(2-methyl-N-phenyl-4-azapentalene)(2-methyl-4-(4'-tris(trifluoromethyl)methylphenylindenyl)methylzirconiummethylbis(pentafluorophenyl)pyrrolylborate dimethylsilanediyl(2-methyl-N-phenyl-5-azapentalene)(2-methyl-4-(4'-tris(trifluoromethyl)methylphenylindenyl)methylzirconiummethylbis(pentafluorophenyl)pyrrolylborate dimethylsilanediyl(2-methyl-N-phenyl-6-azapentalene)(2-methyl-4-(4'-tris(trifluoromethyl)methylphenylindenyl)methylzirconiummethylbis(pentafluorophenyl)pyrrolylborate dimethylsilanediyl(2,5-dimethyl-4-azapentalene)(2-methyl-4-(4'-tris(trifluoromethyl)methylphenylindenyl)methylzirconiummethylbis(pentafluorophenyl)pyrrolylborate dimethylsilanediyl(2,5-dimethyl-6-azapentalene)(2-methyl-4-(4'-tris(trifluoromethyl)methylphenylindenyl)methylzirconiummethylbis(pentafluorophenyl)pyrrolylborate dimethylsilanediyl(2,5-dimethyl-N-phenyl-4-azapentalene)(2-methyl-4-(4'-tris(trifluoromethyl)methylphenylindenyl)methylzirconiummethylbis(pentafluorophenyl)pyrrolylborate dimethylsilanediyl(2,5-dimethyl-N-phenyl-6-azapentalene)(2-methyl-4-(4'-tris(trifluoromethyl)methylphenylindenyl)methylzirconiummethylbis(pentafluorophenyl)pyrrolylborate dimethylsilanediyl(2-methyl-4-thiapentalene)(2-methyl-4-(4'-tris(trifluoromethyl)methylphenylindenyl)methylzirconiummethylbis(pentafluorophenyl)pyrrolylborate dimethylsilanediyl(2-methyl-5-thiapentalene)(2-methyl-4-(4'-tris(trifluoromethyl)methylphenylindenyl)methylzirconiummethylbis(pentafluorophenyl)pyrrolylborate dimethylsilanediyl(2-methyl-6-thiapentalene)(2-methyl-4-(4'-tris(trifluoromethyl)methylphenylindenyl)methylzirconiummethylbis(pentafluorophenyl)pyrrolylborate dimethylsilanediyl(2,5-dimethyl-4-thiapentalene)(2-methyl-4-(4'-tris(trifluoromethyl)methylphenylindenyl)methylzirconiummethylbis(pentafluorophenyl)pyrrolylborate dimethylsilanediyl(2,5-dimethyl-6-thiapentalene)(2-methyl-4-(4'-tris(trifluoromethyl)methylphenylindenyl)methylzirconiummethylbis(pentafluorophenyl)pyrrolylborate dimethylsilanediyl(2-methyl-4-oxapentalene)(2-methyl-4-(4'-tris(trifluoromethyl)methylphenylindenyl)methylzirconiummethylbis(pentafluorophenyl)pyrrolylborate dimethylsilanediyl(2-methyl-5-oxapentalene)(2-methyl-4-(4'-tris(trifluoromethyl)methylphenylindenyl)methylzirconiummethylbis(pentafluorophenyl)pyrrolylborate dimethylsilanediyl(2-methyl-6-oxapentalene)(2-methyl-4-(4'-tris(trifluoromethyl)methylphenylindenyl)methylzirconiummethylbis(pentafluorophenyl)pyrrolylborate dimethylsilanediyl(2,5-dimethyl-4-oxapentalene)(2-methyl-4-(4'-tris(trifluoromethyl)methylphenylindenyl)methylzirconiummethylbis(pentafluorophenyl)pyrrolylborate dimethylsilanediyl(2,5-dimethyl-6-oxapentalene)(2-methyl-4-(4'-tris(trifluoromethyl)methylphenylindenyl)methylzirconiummethylbis(pentafluorophenyl)pyrrolylborate dimethylsilanediyl(2-methyl-4-azapentalene)(2-ethyl-4-(4'-tert-butylphenylindenyl)methylzirconiummethylbis(pentafluorophenyl)pyrrolylborate dimethylsilanediyl(2-methyl-5,6-dihydro-4-azapentalene)(2-ethyl-4-(4'-tert-butylphenylindenyl)methylzirconiummethylbis(pentafluorophenyl)pyrrolylborate dimethylsilanediyl(2-methyl-4-azapentalene)(2-ethyl-4-(4'-tert-butylphenyltetrahydroindenyl)methylzirconiummethylbis(pentafluorophenyl)pyrrolylborate dimethylsilanediyl(2-methyl-5-azapentalene)(2-n-butyl-4-(4'-tert-butylphenylindenyl)methylzirconiummethylbis(pentafluorophenyl)pyrrolylborate ethylidene(2-methyl-6-azapentalene)(2-methyl-4-(4'-tert-butylphenylindenyl)methylzirconiummethylbis(pentafluorophenyl)pyrrolylborate dimethylsilanediyl(2-methyl-N-trimethylsilyl-4-azapentalene)(2-methyl-4-(4'-tertbutylphenylindenyl)methylzirconiummethylbis(pentafluorophenyl)pyrrolylborate dimethylsilanediyl(2-methyl-N-tolyl-5-azapentalene)(2-n-propyl-4-(4'-tert-butylphenylindenyl)methylzirconiummethylbis(pentafluorophenyl)pyrrolylborate dimethylgermyldiyl(2-methyl-N-phenyl-6-azapentalene)(2-methyl-4-(4'-tert-butylphenylindenyl)methylzirconiummethylbis(pentafluorophenyl)pyrrolylborate methylethylidene(2,5-dimethyl-4-azapentalene)(2-methyl-4-(4'-tert-butylphenylindenyl)methylzirconiummethylbis(pentafluorophenyl)pyrrolylborate dimethylsilanediyl(2,5-diisopropyl-6-azapentalene)(2-methyl-4-(4'-tert-butylphenylindenyl)methylzirconiummethylbis(pentafluorophenyl)pyrrolylborate dimethylsilanediyl(2,5-dimethyl-N-phenyl-4-azapentalene)(2,6-dimethyl-4-(4'-tert-butylphenylindenyl)methylzirconiummethylbis(pentafluorophenyl)pyrrolylborate dimethylsilanediyl(2,5-dimethyl-N-phenyl-6-azapentalene)(2-methyl-4-(6'-tert-butylnaphthylindenyl)methylzirconiummethylbis(pentafluorophenyl)pyrrolylborate dimethylsilanediyl(2,5-dimethyl-N-phenyl-6-azapentalene)(2-methyl-4-(6'-tert-butylanthracenylindenyl)methylzirconiummethylbis(pentafluorophenyl)pyrrolylborate dimethylsilanediyl(2-methyl-4-phosphapentalene)(2-methyl-4-(4'-tert-butylphenylindenyl)methylzirconiummethylbis(pentafluorophenyl)pyrrolylborate diphenylsilanediyl(2-methyl-5-thiapentalene)(2-methyl-4-(4'-tert-butylphenylindenyl)methylzirconiummethylbis(pentafluorophenyl)pyrrolylborate methylphenylsilanediyl(2-methyl-6-thiapentalene)(2-methyl-4-(4'-tert-butylphenylindenyl)methylzirconiummethylbis(pentafluorophenyl)pyrrolylborate methylidene(2,5-dimethyl-4-thiapentalene)(2-methyl-4-(4'-tert-butylphenylindenyl)methylzirconiummethylbis(pentafluorophenyl)pyrrolylborate dimethylmethylidene(2,5-dimethyl-6-thiapentalene)(2-methyl-4-(4'-tert-butylphenylindenyl)methylzirconiummethylbis(pentafluorophenyl)pyrrolylborate diphenylsilanediyl(2,5-dimethyl-4-oxapentalene)(2-methyl-4-(4'-tert-butylphenylindenyl)methylzirconiummethylbis(pentafluorophenyl)pyrrolylborate diphenylsilanediyl(2,5-dimethyl-6-oxapentalene)(2-methyl-4-(4'-tert-butylphenylindenyl)methylzirconiummethylbis(pentafluorophenyl)pyrrolylborate dimethylsilanediyl(2-methyl-4-azapentalene)(2-methylindenyl)methylzirconiummethylbis(pentafluorophenyl)pyrrolylborate dimethylsilanediyl(2-methyl-5-azapentalene)(2-methylindenyl)methylzirconiummethylbis(pentafluorophenyl)pyrrolylborate dimethylsilanediyl(2-methyl-6-azapentalene)(2-methylindenyl)methylzirconiummethylbis(pentafluorophenyl)pyrrolylborate dimethylsilanediyl(2-methyl-N-phenyl-4-azapentalene)(2-methylindenyl)methylzirconiummethylbis(pentafluorophenyl)pyrrolylborate dimethylsilanediyl(2-methyl-N-phenyl-5-azapentalene)(2-methylindenyl)methylzirconiummethylbis(pentafluorophenyl)pyrrolylborate dimethylsilanediyl(2-methyl-N-phenyl-6-azapentalene)(2-methylindenyl)methylzirconiummethylbis(pentafluorophenyl)pyrrolylborate dimethylsilanediyl(2,5-dimethyl-4-azapentalene)(2-methylindenyl)methylzirconiummethylbis(pentafluorophenyl)pyrrolylborate dimethylsilanediyl(2,5-dimethyl-6-azapentalene)(2-methylindenyl)methylzirconiummethylbis(pentafluorophenyl)pyrrolylborate dimethylsilanediyl(2,5-dimethyl-N-phenyl-4-azapentalene)(2-methylindenyl)methylzirconiummethylbis(pentafluorophenyl)pyrrolylborate dimethylsilanediyl(2,5-dimethyl-N-phenyl-6-azapentalene)(2-methylindenyl)methylzirconiummethylbis(pentafluorophenyl)pyrrolylborate dimethylsilanediyl(2-methyl-4-thiapentalene)(2-methylindenyl)methylzirconiummethylbis(pentafluorophenyl)pyrrolylborate dimethylsilanediyl(2-methyl-5-thiapentalene)(2-methylindenyl)methylzirconiummethylbis(pentafluorophenyl)pyrrolylborate dimethylsilanediyl(2-methyl-6-thiapentalene)(2-methylindenyl)methylzirconiummethylbis(pentafluorophenyl)pyrrolylborate dimethylsilanediyl(2,5-dimethyl-4-thiapentalene)(2-methylindenyl)methylzirconiummethylbis(pentafluorophenyl)pyrrolylborate dimethylsilanediyl(2,5-dimethyl-6-thiapentalene)(2-methylindenyl)methylzirconiummethylbis(pentafluorophenyl)pyrrolylborate dimethylsilanediyl(2-methyl-4-oxapentalene)(2-methylindenyl)methylzirconiummethylbis(pentafluorophenyl)pyrrolylborate dimethylsilanediyl(2-methyl-5-oxapentalene)(2-methylindenyl)methylzirconiummethylbis(pentafluorophenyl)pyrrolylborate dimethylsilanediyl(2-methyl-6-oxapentalene)(2-methylindenyl)methylzirconiummethylbis(pentafluorophenyl)pyrrolylborate dimethylsilanediyl(2,5-dimethyl-4-oxapentalene)(2-methylindenyl)methylzirconiummethylbis(pentafluorophenyl)pyrrolylborate dimethylsilanediyl(2,5-dimethyl-6-oxapentalene)(2-methylindenyl)methylzirconiummethylbis(pentafluorophenyl)pyrrolylborate dimethylsilanediyl(2-methyl-4-azapentalene)(indenyl)methylzirconiummethylbis(pentafluorophenyl)pyrrolylborate dimethylsilanediyl(2-methyl-5-azapentalene)(indenyl)methylzirconiummethylbis(pentafluorophenyl)pyrrolylborate dimethylsilanediyl(2-methyl-6-azapentalene)(indenyl)methylzirconiummethylbis(pentafluorophenyl)pyrrolylborate dimethylsilanediyl(2-methyl-N-phenyl-4-azapentalene)(indenyl)methylzirconiummethylbis(pentafluorophenyl)pyrrolylborate dimethylsilanediyl(2-methyl-N-phenyl-5-azapentalene)(indenyl)methylzirconiummethylbis(pentafluorophenyl)pyrrolylborate dimethylsilanediyl(2-methyl-N-phenyl-6-azapentalene)(indenyl)methylzirconiummethylbis(pentafluorophenyl)pyrrolylborate dimethylsilanediyl(2,5-dimethyl-4-azapentalene)(indenyl)methylzirconiummethylbis(pentafluorophenyl)pyrrolylborate dimethylsilanediyl(2,5-dimethyl-6-azapentalene)(indenyl)methylzirconiummethylbis(pentafluorophenyl)pyrrolylborate dimethylsilanediyl(2,5-dimethyl-N-phenyl-4-azapentalene)(indenyl)methylzirconiummethylbis(pentafluorophenyl)pyrrolylborate dimethylsilanediyl(2,5-dimethyl-N-phenyl-6-azapentalene)(indenyl)methylzirconiummethylbis(pentafluorophenyl)pyrrolylborate dimethylsilanediyl(2-methyl-4-thiapentalene)(indenyl)methylzirconiummethylbis (pentafluorophenyl)pyrrolylborate dimethylsilanediyl(2-methyl-5-thiapentalene)(indenyl)methylzirconiummethylbis(pentafluorophenyl)pyrrolylborate dimethylsilanediyl(2-methyl-6-thiapentalene)(indenyl)methylzirconiummethylbis(pentafluorophenyl)pyrrolylborate dimethylsilanediyl(2,5-dimethyl-4-thiapentalene)(indenyl)methylzirconiummethylbis(pentafluorophenyl)pyrrolylborate dimethylsilanediyl(2,5-dimethyl-6-thiapentalene)(indenyl)methylzirconiummethylbis(pentafluorophenyl)pyrrolylborate dimethylsilanediyl(2-methyl-4-oxapentalene)(indenyl)methylzirconiummethylbis(pentafluorophenyl)pyrrolylborate dimethylsilanediyl(2-methyl-5-oxapentalene)(indenyl)methylzirconiummethylbis(pentafluorophenyl)pyrrolylborate dimethylsilanediyl(2-methyl-6-oxapentalene)(indenyl)methylzirconiummethylbis(pentafluorophenyl)pyrrolylborate dimethylsilanediyl(2,5-dimethyl-4-oxapentalene)(indenyl)methylzirconiummethylbis(pentafluorophenyl)pyrrolylborate dimethylsilanediyl(2,5-dimethyl-6-oxapentalene)(indenyl)methylzirconiummethylbis(pentafluorophenyl)pyrrolylborate dimethylsilanediyl(2-methyl-4-azapentalene)(2-methyl-4-phenylindenyl)methylzirconiummethylbis(pentafluorophenyl)pyrrolylborate dimethylsilanediyl(2-methyl-5-azapentalene)(2-methyl-4-phenylindenyl)methylzirconiummethylbis(pentafluorophenyl)pyrrolylborate dimethylsilanediyl(2-methyl-6-azapentalene)(2-methyl-4-phenylindenyl)methylzirconiummethylbis(pentafluorophenyl)pyrrolylborate dimethylsilanediyl(2-methyl-N-phenyl-4-azapentalene)(2-methyl-4-phenylindenyl)methylzirconiummethylbis(pentafluorophenyl)pyrrolylborate dimethylsilanediyl(2-methyl-N-phenyl-5-azapentalene)(2-methyl-4-phenylindenyl)methylzirconiummethylbis(pentafluorophenyl)pyrrolylborate dimethylsilanediyl(2-methyl-N-phenyl-6-azapentalene)(2-methyl-4-phenylindenyl)methylzirconiummethylbis(pentafluorophenyl)pyrrolylborate dimethylsilanediyl(2,5-dimethyl-4-azapentalene)(2-methyl-4-phenylindenyl)methylzirconiummethylbis(pentafluorophenyl)pyrrolylborate dimethylsilanediyl(2,5-dimethyl-6-azapentalene)(2-methyl-4-phenylindenyl)methylzirconiummethylbis(pentafluorophenyl)pyrrolylborate dimethylsilanediyl(2,5-dimethyl-N-phenyl-4-azapentalene)(2-methyl-4-phenylindenyl)methylzirconiummethylbis(pentafluorophenyl)pyrrolylborate dimethylsilanediyl(2,5-dimethyl-N-phenyl-6-azapentalene)(2-methyl-4-phenylindenyl)methylzirconiummethylbis(pentafluorophenyl)pyrrolylborate dimethylsilanediyl(2-methyl-4-thiapentalene)(2-methyl-4-phenylindenyl)methylzirconiummethylbis(pentafluorophenyl)pyrrolylborate dimethylsilanediyl(2-methyl-5-thiapentalene)(2-methyl-4-phenylindenyl)methylzirconiummethylbis(pentafluorophenyl)pyrrolylborate dimethylsilanediyl(2-methyl-6-thiapentalene)(2-methyl-4-phenylindenyl)methylzirconiummethylbis(pentafluorophenyl)pyrrolylborate dimethylsilanediyl(2,5-dimethyl-4-thiapentalene)(2-methyl-4-phenylindenyl)methylzirconiummethylbis(pentafluorophenyl)pyrrolylborate dimethylsilanediyl(2,5-dimethyl-6-thiapentalene)(2-methyl-4-phenylindenyl)methylzirconiummethylbis(pentafluorophenyl)pyrrolylborate dimethylsilanediyl(2-methyl-4-oxapentalene)(2-methyl-4-phenylindenyl)methylzirconiummethylbis(pentafluorophenyl)pyrrolylborate dimethylsilanediyl(2-methyl-5-oxapentalene)(2-methyl-4-phenylindenyl)methylzirconiummethylbis(pentafluorophenyl)pyrrolylborate dimethylsilanediyl(2-methyl-6-oxapentalene)(2-methyl-4-phenylindenyl)methylzirconiummethylbis(pentafluorophenyl)pyrrolylborate dimethylsilanediyl(2,5-dimethyl-4-oxapentalene)(2-methyl-4-phenylindenyl)methylzirconiummethylbis(pentafluorophenyl)pyrrolylborate dimethylsilanediyl(2,5-dimethyl-6-oxapentalene)(2-methyl-4-phenylindenyl)methylzirconiummethylbis(pentafluorophenyl)pyrrolylborate dimethylsilanediyl(2-methyl-4-azapentalene)(2-methyl-4,5-benzindenyl)methylzirconiummethylbis(pentafluorophenyl)pyrrolylborate dimethylsilanediyl(2-methyl-5-azapentalene)(2-methyl-4,5-benzoindenyl)methylzirconiummethylbis(pentafluorophenyl)pyrrolylborate dimethylsilanediyl(2-methyl-6-azapentalene)(2-methyl-4,5-benzoindenyl)methylzirconiummethylbis(pentafluorophenyl)pyrrolylborate dimethylsilanediyl(2-methyl-N-phenyl-4-azapentalene)(2-methyl-4,5-benzindenyl)methylzirconiummethylbis(pentafluorophenyl)pyrrolylborate dimethylsilanediyl(2-methyl-N-phenyl-5-azapentalene)(2-methyl-4,5-benzindenyl)methylzirconiummethylbis(pentafluorophenyl)pyrrolylborate dimethylsilanediyl(2-methyl-N-phenyl-6-azapentalene)(2-methyl-4,5-benzindenyl)methylzirconiummethylbis(pentafluorophenyl)pyrrolylborate dimethylsilanediyl(2,5-dimethyl-4-azapentalene)(2-methyl-4,5-benzindenyl)methylzirconiummethylbis(pentafluorophenyl)pyrrolylborate dimethylsilanediyl(2,5-dimethyl-6-azapentalene)(2-methyl-4,5-benzindenyl)methylzirconiummethylbis(pentafluorophenyl)pyrrolylborate dimethylsilanediyl(2,5-dimethyl-N-phenyl-4-azapentalene)(2-methyl-4,5-benzindenyl)methylzirconiummethylbis(pentafluorophenyl)pyrrolylborate dimethylsilanediyl(2,5-dimethyl-N-phenyl-6-azapentalene)(2-methyl-4,5-benzindenyl)methylzirconiummethylbis(pentafluorophenyl)pyrrolylborate dimethylsilanediyl(2-methyl-4-thiapentalene)(2-methyl-4,5-benzindenyl)methylzirconiummethylbis(pentafluorophenyl)pyrrolylborate dimethylsilanediyl(2-methyl-5-thiapentalene)(2-methyl-4,5-benzindenyl)methylzirconiummethylbis(pentafluorophenyl)pyrrolylborate dimethylsilanediyl(2-methyl-6-thiapentalene)(2-methyl-4,5-benzindenyl)methylzirconiummethylbis(pentafluorophenyl)pyrrolylborate dimethylsilanediyl(2,5-dimethyl-4-thiapentalene)(2-methyl-4,5-benzindenyl)methylzirconiummethylbis(pentafluorophenyl)pyrrolylborate dimethylsilanediyl(2,5-dimethyl-6-thiapentalene)(2-methyl-4,5-benzindenyl)methylzirconiummethylbis(pentafluorophenyl)pyrrolylborate dimethylsilanediyl(2-methyl-4-oxapentalene)(2-methyl-4,5-benzoindenyl)methylzirconiummethylbis(pentafluorophenyl)pyrrolylborate dimethylsilanediyl(2-methyl-5-oxapentalene)(2-methyl-4,5-benzoindenyl)methylzirconiummethylbis(pentafluorophenyl)

pyrrolylborate dimethylsilanediyl(2-methyl-6-oxapentalene)(2-methyl-4,5-benzoindenyl)methylzirconiummethylbis(pentafluorophenyl)pyrrolylborate dimethylsilanediyl(2,5-dimethyl-4-oxapentalene)(2-methyl-4,5-benzindenyl)methylzirconiummethylbis(pentafluorophenyl)pyrrolylborate dimethylsilanediyl(2,5-dimethyl-6-oxapentalene)(2-methyl-4,5-benzindenyl)methylzirconiummethylbis(pentafluorophenyl)pyrrolylborate dimethylsilanediylbis(2-methyl-4-azapentalene)methylzirconiummethylbis(pentafluorophenyl)pyrrolylborate dimethylsilanediylbis(2-methyl-5-azapentalene)methylzirconiummethylbis(pentafluorophenyl)pyrrolylborate dimethylsilanediylbis(2-methyl-6-azapentalene)methylzirconiummethylbis(pentafluorophenyl)pyrrolylborate dimethylsilanediylbis(2-methyl-N-phenyl-4-azapentalene)methylzirconiummethylbis(pentafluorophenyl)pyrrolylborate dimethylsilanediylbis(2-methyl-N-phenyl-5-azapentalene)methylzirconiummethylbis(pentafluorophenyl)pyrrolylborate dimethylsilanediylbis(2-methyl-N-phenyl-6-azapentalene)methylzirconiummethylbis(pentafluorophenyl)pyrrolylborate dimethylsilanediylbis(2,5-dimethyl-4-azapentalene)methylzirconiummethylbis(pentafluorophenyl)pyrrolylborate dimethylsilanediylbis(2,5-dimethyl-6-azapentalene)methylzirconiummethylbis(pentafluorophenyl)pyrrolylborate dimethylsilanediylbis(2,5-dimethyl-N-phenyl-4-azapentalene)methylzirconiummethylbis(pentafluorophenyl)pyrrolylborate dimethylsilanediylbis(2,5-dimethyl-N-phenyl-6-azapentalene)methylzirconiummethylbis(pentafluorophenyl)pyrrolylborate dimethylsilanediylbis(2-methyl-4-thiapentalene)methylzirconiummethylbis(pentafluorophenyl)pyrrolylborate dimethylsilanediylbis(2-methyl-5-thiapentalene)methylzirconiummethylbis(pentafluorophenyl)pyrrolylborate dimethylsilanediylbis(2-methyl-6-thiapentalene)methylzirconiummethylbis(pentafluorophenyl)pyrrolylborate dimethylsilanediylbis(2,5-dimethyl-4-thiapentalene)methylzirconiummethylbis(pentafluorophenyl)pyrrolylborate dimethylsilanediylbis(2,5-dimethyl-6-thiapentalene)methylzirconiummethylbis(pentafluorophenyl)pyrrolylborate dimethylsilanediylbis(2,5-dimethyl-4-oxapentalene)methylzirconiummethylbis(pentafluorophenyl)pyrrolylborate dimethylsilanediylbis(2-methyl-5-oxapentalene)methylzirconiummethylbis(pentafluorophenyl)pyrrolylborate dimethylsilanediylbis(2-methyl-6-oxapentalene)methylzirconiummethylbis(pentafluorophenyl)pyrrolylborate dimethylsilanediylbis(2,5-dimethyl-4-oxapentalene)methylzirconiummethylbis(pentafluorophenyl)pyrrolylborate dimethylsilanediylbis(2,5-dimethyl-6-oxapentalene)methylzirconiummethylbis(pentafluorophenyl)pyrrolylborate The corresponding compounds in which the pyrrole was replaced by imidazoles, benzimidazoles and indoles are furthermore preferred.

The novel compounds of the formulae I and II may also be used in supported form.

The support component of the novel catalyst system may be any organic or inorganic, inert solid, in particular a porous support, such as talc, inorganic oxides and finely divided polymer powders (e.g. polyolefins).

Suitable inorganic oxides occur in groups 2, 3, 4, 5, 13, 14, 15 and 16 of the Periodic Table of the Elements. Examples of oxides preferred as supports include silica, alumina and mixed oxides of the two elements and corresponding oxide mixtures. Other inorganic oxides which may be used alone or in combination with the last-mentioned preferred oxide supports are, for example, MgO, $ZrO_2$, $TiO_2$ or $B_2O_3$, to mention but a few.

The support materials used have a specific surface area of from 10 to 1000 $m^2$/g, a pore volume of from 0.1 to 5 ml/g and a mean particle size of from 1 to 500 μm. Preferred supports are those having a specific surface area of from 50 to 500 μm, a pore volume of from 0.5 to 3.5 ml/g and a mean particle size of from 5 to 350 μm. Particularly preferred supports are those having a specific surface area of from 200 to 400 $m^2$/g, a pore volume of from 0.8 to 3.0 ml/g and a mean particle size of from 10 to 200 μm.

If the support material used has by its very nature a low moisture content or residual solvent content, dehydration or drying prior to use may be dispensed with. If this is not the case, as with the use of silica gel as support material, dehydration or drying is advisable. Thermal dehydration or drying of the support material can be carried out under reduced pressure with simultaneous blanketing with inert gas (e.g. nitrogen). The drying temperature is from 100 to 1000° C., preferably from 200 to 800° C. In this case, the pressure is not critical. The duration of the drying process may be from 1 to 24 hours. Shorter or longer drying periods are possible provided that, under the chosen conditions, equilibration with the hydroxyl groups on the support surface can be effected, which usually requires from 4 to 8 hours.

Dehydration or drying of the support material is also possible by chemical methods, by reacting the adsorbed water and the hydroxyl groups on the surface with suitable compositions which impart inertness. By reaction with the reagent imparting inertness, some or all of the hydroxyl groups can be converted into a form which does not lead to any adverse interaction with the catalytically active centers. Suitable compositions which impart inertness are, for example, silicon halides and silanes, such as silicon tetrachloride, chlorotrimethylsilane or dimethylaminotrichlorosilane, or organometallic compounds of aluminum, boron and magnesium, for example trimethylaluminum, triethylaluminum, triisobutylaluminum, triethylborane or dibutylmagnesium. The chemical dehydration of the support material or the imparting of inert properties to said material is effected, for example, by reacting a suspension of the support material in a suitable solvent, in the absence of air and moisture, with the reagent imparting inertness, in pure form or dissolved in a suitable solvent. Suitable solvents are, for example, aliphatic or aromatic hydrocarbons, such as pentane, hexane, heptane, toluene or xylene. Imparting inert properties is effected at from 25° C. to 120° C., preferably from 50 to 70° C. Higher and lower temperatures are possible. The duration of the reaction is from 30 minutes to 20 hours, preferably from 1 to 5 hours. After the chemical dehydration is complete, the support material is isolated by filtration under inert conditions, washed once or several times with suitable inert solvents as described above and then dried in an inert gas stream or under reduced pressure.

Organic support materials, such as finely divided polyolefin powders (e.g. polyethylene, polypropylene or polystyrene) may also be used and should likewise be freed from adhering moisture, solvent residues or other impurities by appropriate cleaning and drying operations before use.

The present invention also relates to a process for the preparation of a polyolefin by polymerization of one or more olefins in the presence of the novel catalyst systems, containing at least one transition metal component of the formula I. The term polymerization is understood as meaning homopolymerization as well as copolymerization.

Olefins of the formula $R_m$—CH=CH—$R_n$, where $R_m$ and $R_n$ are identical or different and are a hydrogen atom or a carbon-containing radical of 1 to 20, in particular 1 to 10, carbon atoms and $R_m$ and $R_n$, together with the atoms linking them, may form one or more rings, are preferably polymerized.

Examples of such olefins are 1-olefins of 2–40, preferably 2 to 10, carbon atoms, such as ethene, propene, 1-butene, 1-pentene, 1-hexene, 4-methyl-1-pentene or 1-octene, styrene, dienes, such as 1,3-butadiene, 1,4-hexadiene, vinylnorbornene, norbornadiene, ethylnorbornadiene and cyclic olefins, such as norbornene, tetracyclododecene or methylnorbornene. In the novel process, propene or ethene are preferably subjected to homopolymerization, or propene is copolymerized with ethene and/or with one or more 1-olefins of 4 to 20 carbon atoms, such as hexene and/or with one or more dienes of 4 to 20 carbon atoms, such as 1,4-butadiene, norbornadiene, ethylidenenorbornene or ethylnorbornadiene. Examples of such copolymers are ethene/propene copolymers or ethene/propene/1,4-hexadiene terpolymers.

The polymerization is carried out at from −60 to 300° C., preferably from 50 to 200° C., very particularly preferably from 50–80° C. The pressure is from 0.5 to 2000, preferably from 5 to 64, bar.

The polymerization can be carried out as a solution, mass, suspension or gas-phase polymerization, continuously or batchwise, in one or more stages.

The catalyst system prepared according to the invention can be used as the sole catalyst component for the polymerization of olefins of 2 to 20 carbon atoms, or preferably in combination with at least one alkyl compound of the elements of main groups I to III of the Periodic Table, such as an alkylaluminum, alkylmagnesium or alkyllithium or an aluminoxane. The alkyl compound is added to the monomer or suspending medium and serves for purifying the monomer by removing substances which may impair the catalyst activity. The amount of alkyl compound added depends on the quality of the monomers used.

If necessary, hydrogen is added as a molar mass regulator and/or for increasing the activity.

During the polymerization, an antistatic agent may additionally be metered into the polymerization system, together with or separately from the catalyst system used.

Mixtures of two or more transition metal compounds of the formula I and/or formula II may also be used. As a result, polyolefins having a broad or multimodal molecular weight distribution can be obtained.

In addition, further cocatalytically active compounds may be present during the polymerization.

The cocatalyst component which, according to the invention, may be present in the catalyst system contains at least one compound of the aluminoxane type or Lewis acid type or an anionic compound which, by reaction with a metallocene, converts the latter into a cationic compound.

A preferably used aluminoxane is a compound of the formula (III)

$$(R\,AlO)_n \qquad \text{(III)}.$$

Further suitable aluminoxanes may be, for example, cyclic, as in the formula (IV)

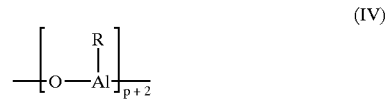

or linear, as in the formula (V)

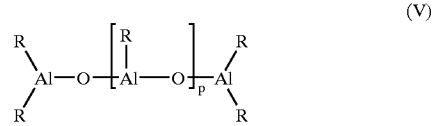

or of the cluster type, as in the formula (VI)

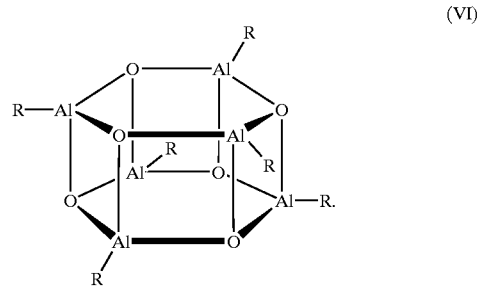

Such aluminoxanes are described, for example, in JACS 117 (1995), 6465–74, and Organometallics 13 (1994), 2957–2969.

The radicals R in the formulae (III), (IV), (V) and (VI) may be identical or different and are a $C_1$–$C_{20}$-hydrocarbon group, such as $C_1$–$C_6$-alkyl, $C_6$–$C_{18}$-aryl, benzyl or hydrogen, and p is an integer from 2 to 50, particularly from 10 to 35.

Preferably, the radicals R are identical and are methyl, isobutyl, n-butyl, phenyl or benzyl, particularly preferably methyl.

If the radicals R are different, they are preferably methyl and hydrogen, methyl and isobutyl or methyl and n-butyl, hydrogen and isobutyl or n-butyl preferably being present in an amount of 0.01–40% (number of radicals R).

The aluminoxane can be prepared in various ways by known processes. In one of the methods, for example, an aluminum-hydrocarbon compound and/or a hydridoaluminum-hydrocarbon compound is reacted with water (gaseous, solid, liquid or bound—for example as water of crystallization) in an inert solvent (e.g. toluene).

For the preparation of an aluminoxane having different alkyl groups R, two different trialkylaluminums ($R_3Al$+ $R'_3Al$), depending on the desired composition and reactivity, are reacted with water (cf. S. Pasynkiewicz, Polyhedron 9 (1990) 429 and EP-A-0,302,424).

Regardless of the method of preparation, a feature common to all aluminoxane solutions is that they have a varying content of unconverted aluminum starting compound, which is present in free form or as an adduct.

At least one organoboron or organoaluminum compound which contains $c_1$–$C_{20}$-carbon-containing groups, such as branched or straight-chain alkyl or haloalkyl, e.g. methyl, propyl, isopropyl, isobutyl, or trifluoromethyl, or unsaturated groups, such as aryl or haloaryl, e.g. phenyl, tolyl, benzyl, p-fluorophenyl, 3,5-difluorophenyl, pentachlorophenyl, pentafluorophenyl, 3,4,5-trifluorophenyl and 3,5-di(trifluoromethyl)phenyl, is preferably used as the Lewis acid.

Examples of Lewis acids are trimethylaluminum, triethylaluminum, triisobutylaluminum, tributylaluminum, trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane and/or tris(3,4,5-trifluorophenyl)borane. Tris(pentafluorophenyl)borane is particularly preferred.

The ionic cocatalysts used are preferably compounds which contain a noncoordinating anion, for example tetrakis(pentafluorophenyl)borates, tetraphenylborates, $SbF_6^-$, $CF_3SO_3^-$ or $ClO_4^-$. Lewis bases, e.g. methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene and triphenylcarbenium, are used as the cation.

Examples of such anionic compounds according to the invention are triethylammonium tetra(phenyl)borate, tributylammonium tetra(phenyl)borate, trimethylammonium tetra(tolyl)borate, tributylammonium tetra(tolyl)borate, tributylammonium tetra(pentafluorophenyl)borate, tributylammonium tetra(pentafluorophenyl)aluminate, tripropylammonium tetra(dimethylphenyl)borate, tributylammonium tetra(trifluoromethylphenyl)borate, tributylammonium tetra(4-fluorophenyl)borate, N,N-dimethylanilinium tetra(phenyl)borate, N,N-diethylanilinium tetra(phenyl)borate, N,N-dimethylanilinium tetrakis(pentafluorophenyl)borate, N,N-dimethylanilinium tetrakis(pentafluorophenyl)aluminate, di(propyl)ammonium tetrakis(pentafluorophenyl)borate, di(cyclohexyl)ammonium tetrakis(pentafluorophenyl)borate, triphenylphosphonium tetrakis(phenyl)borate, triethylphosphonium tetrakis(phenyl)borate, diphenylphosphonium tetrakis(phenyl)borate, tri(methylphenyl)phosphonium tetrakis(phenyl)borate, tri(dimethylphenyl)phosphonium tetrakis(phenyl)borate, triphenylcarbenium tetrakis(pentafluorophenyl)borate, triphenylcarbenium tetrakis(pentafluorophenyl)aluminate, triphenylcarbenium tetrakis(phenyl)aluminate, ferrocenium tetrakis(pentafluorophenyl)borate and/or ferrocenium tetrakis(pentafluorophenyl)aluminate, triphenylcarbenium tetrakis(pentafluorophenyl)borate and/or N,N-dimethylanilinium tetrakis(pentafluorophenyl)borate.

Mixtures of at least one Lewis acid and at least one ionic compound may also be used.

Other important cocatalyst components are borane and carborane compounds, e.g.

7,8-dicarbaundecaborane(13), undecahydrido-7,8-dimethyl-7,8-dicarbaundecaborane, dodecahydrido-1-phenyl-1,3-dicarbanonaborane, tri(butyl)ammonium undecahydrido-8-ethyl-7,9-dicarbaundecaborate, 4-carbanonaborane(14)bis(tri(butyl)ammonium)nonaborate, bis(tri(butyl)ammonium)undecaborate, bis(tri(butyl)ammonium)dodecaborate, bis(tri(butyl)ammonium)decachlorodecaborate, tri(butyl)ammonium 1-carbadecaborates, tri(butyl)ammonium 1-carbadodecaborates, tri(butyl)ammonium 1-trimethylsilyl-1-carbadecaborates, tri(butyl)ammonium bis(nonahydrido-1,3-dicarbononaborate)cobaltates(III), tri(butyl)ammonium bis(undecahydrido-7,8-dicarbaundecaborate)ferrate(III).

A prepolymerization can be carried out with the aid of the compounds of the formulae I and II. The (or one of the) olefin(s) used in the polymerization is employed for the prepolymerization.

The examples which follow illustrate the invention.

General information: Preparation and handling of the compounds were carried out in the absence of air and moisture under an inert argon atmosphere (Schlenk technique). All solvents required were converted into absolute form prior to use by boiling for several hours over suitable drying agents and subsequent distillation under argon.

The butadiene complexes are synthesized according to G. Erker, K. Engel, Ch. Sarter in R. B. King, J. J. Eisch, Organometallic Synthesis 3 (1986), 529, Academic Press, New York.

Pyrrolidinylboron dichloride is prepared according to K. Niederzu, J. Am. Chem. Soc. 81 (1959), 5553. The (pentafluorophenyl)boron fluoride ether complex is synthesized according to M. Bochmann, Organometallics 16 (1997), 4995. Tris($\eta^5$-cyclopentadienyl)methylzirconium is synthesized according to Brackemeyer, G. Erker, R. Fröhlich, Organometallics 16, (1997), 531.

The compounds were characterized by $^1$H-NMR, $^{13}$C-NMR and IR spectroscopy.

EXAMPLE 1

Synthesis of bis(Pentafluorophenyl)pyrrolylborane

A suspension of 5.316 g (72.8 mmol) of pyrrolyllithium in 50 ml of ether is carefully added in portions to 140 ml (72.8 mmol) of a freshly prepared 0.52M bis(pentafluorophenyl)boron fluoride ether complex/ether solution at $-78°$ C. The reaction mixture is slowly heated to room temperature and stirred for a further 14 hours. Thereafter, the solvent is changed from ether to pentane. The precipitate is filtered off and the solid is washed twice with 20 ml of pentane. The yellowish, clear pentane phase is evaporated down until the first crystallization nuclei are detectable and is kept at 8° C. The product is obtained as colorless crystals by fractional crystallization at 8° C. Yield: 15.6 g (38.0 mmol, 52%).

Elemental analysis (%) $C_{16}H_4NBF_{10}$ ($M_r$=411.0): calculated: C 46.76, H 0.98, N 3.41; found: C 46.58, 1.25, N 3.30. $^1$H-NMR (200.13 MHz, $C_6D_6$, 300 K): $\delta$=6.59 (m, 2H, H(2,5)), 6.23 (m, 2H, H(3,4)). 13C-NMR (75.47 MHz, $C_6D_6$, 300 K): $\delta$=147.1 (dm, 1J(F,C)=256.7 Hz, $ArF_{ortho}$), 143.4 (dm, 1J(F,C)=239.6 Hz, $ArF_{para}$), 138.1 (dm, 1J(F,C)=254.3 Hz, $ArF_{meta}$), 127.7 (C(2,5)), 118.3 (C(3,4)), 110.0 (broad, Cipso). 11B-NMR (64.21 MHz, $C_6D_6$, 300K): $\delta$=40.8 (v½=480 Hz). 14N-NMR (14.47 MHz, $C_6D_6$, 300K): $\delta$=–176 (v½=510 Hz). 19F-NMR (282.41 MHz, $C_6D_6$, 300K): $\delta$=–130.5 (m, 2F, $F_{meta}$), –148.4 (t, 1F, $F_{para}$), –160.0 (m, 2F, $F_{ortho}$).

EXAMPLE 2

Synthesis of bis($\eta^5$-Cyclopentadienyl)methylzirconiummethylbis(pentafluorophenyl)pyrrolylborate 0.133 g (0.529 mmol) of bis($\eta^5$-cyclopentadienyl)dimethylzirconium and 0.217 g (0.529 mmol) of bis(pentafluorophenyl)pyrrolylborane are dissolved in 10 ml of toluene at room temperature and stirred for 5 minutes. The solvent is then removed under reduced pressure. The remaining precipitate is taken up with 20 ml of pentane and stirred for 10 minutes. After filtration of the yellow suspension and washing of the residue with two 5 ml portions of pentane, the product is obtained as a yellow powder. Yield: 0.217 g (0.284 mmol; 62%).

1H-NMR (200.13 MHz, $C_6D_6$, 300 K): $\delta$=7.22 (m, 2H, H(2,5)), 5.22 (m, 2H, H(3,4)), 5.15 (s, 10H, Cp), 1.11 (broad m, 3H, BMe), −0.03 (s, 3H, ZrMe). 1H-NMR (599.9 MHz, C$_7$D$_8$, 298 K): δ=7.15 (m, 2H, H(2,5)), 5.14 (m, 2H, H(3,4)), 5.14 (s, 10H, Cp), 0.99 (broad m, 3H, BMe), −0.10 (s, 3H, ZrMe). 1H-NMR (599.9 MHz, C$_7$D$_8$, 253 K): δ=7.20 (m, 2H, H(2,5)), 5.05 (m, 2H, H(3,4)), 5.04 (s, 10H, Cp), 1.10 (broad m, 3H, BMe), −0.11 (s, 3H, ZrMe). 13C-NMR (75.47 MHz, C$_6$D$_6$, 300 K): δ=n.o. (ArF$_{ortho}$, ArF$_{meta}$, ArF$_{para}$), n.o. (C$_{ipso}$), 139.0 (C(2,5)), 112.4 (Cp), 99.6 (C(3,4)), 37.5 (ZrMe), 10.9 (broad, BMe). 13C-NMR (125.9 MHz, C$_7$D$_8$, 298 K): δ=148.6 (dm, 1J(F,C)=248 Hz, ArF$_{ortho}$), 139.3 (dm, 1J(F,C)=250 Hz, ArF$_{para}$), 139.2 (C(2,5)), 137.7 (dm, 1J(F, C)=246 Hz, ArF$_{meta}$), no. (C$_{ipso}$), 112.5 (Cp), 99.4 (C(3,4)), 37.3 (ZrMe), 10.5 (broad, BMe). 13C-NMR (125.9 MHz, C$_7$D$_8$, 253 K): δ=148.3 (dm, 1J(F,C)=242 Hz, ArF$_{ortho}$), 139.1 (dm, 1J(F,C)=239 Hz, ArF$_{para}$), 139.8 (C(2,5)), 137.5 (dm, 1J(F,C)=248 Hz, ArF$_{meta}$), n.o. (C$_{ipso}$), 112.1 (Cp), 98.4 (C(3,4)), 36.4 (ZrMe), 10.5 (broad, BMe). 11B-NMR (64.21 MHz, C$_6$D$_6$, 300K): δ=−6.7 (η½=192 Hz). 19F-NMR (282.41 MHz, C$_6$D$_6$, 300K,): δ=−132.5 (m, 2F, F$_{meta}$), −159.6 (t, 1F, F$_{para}$), −163.9 (m, 2F, F$_{ortho}$).

EXAMPLE 3

Synthesis of tris(η$^5$-Cyclopentadienyl) zirconiummethylbis(pentafluorophenyl) pyrrolylborate 0.132 g (0.438 mmol) of tris(η$^5$-cyclopentadienyl) methylzirconium and 0.180 g (0.438 mmol) of bis(pentafluorophenyl)pyrrolylborane are dissolved in 10 ml of toluene at room temperature and stirred for 1.5 hours. The solvent is then removed under reduced pressure. The remaining precipitate is taken up with 30 ml of pentane and stirred for 3 hours. After filtration of the yellow suspension and washing of the residue with two 10 ml portions of pentane, the product is obtained as a yellow powder. Yield: 0.223 g (0.313 mmol; 71%).

Crystallization from benzene gives single crystals for X-ray structure analysis.

1H-NMR (200.13 MHz, C$_6$D$_6$, 300 K): δ=7.65 (m, 2H, H(2,5)), 5.58 (m, 2H, H(3,4)), 4.94 (s, 15H, Cp), 1.28 (broad m, 3H, BMe). 1H-NMR (599.2 MHz, C$_6$D$_6$, 298 K): δ=7.65 (broad, 2H, H(2,5)), 5.58 (broad, 2H, H(3,4)), 4.94 (s, 15H, Cp), 1.27 (broad m, 3H, BMe). 13C-NMR (125.9 MHz, C$_6$D$_6$, 298 K): δ=148.7 (dm, 1J(F,C)=236 Hz, ArF$_{ortho}$), 142.5 (broad C(2,5)), 139.3 (dm, 1J(F,C=239 Hz, ArF$_{para}$), 137.6 (dm, 1J(F,C)=249 Hz, ArF$_{meta}$), n.b. (C$_{ipso}$), 113.5 (Cp), 113.4 (slightly broadened, C(3,4)), 10.9 (broad, BMe). 11B-NMR (64.21 MHz, C$_6$D$_6$, 300K): δ=−6.8 (η½=188 Hz). 19F-NMR (282.41 MHz, C$_6$D$_6$, 300K): δ=−132.4 (m, 2F, F$_{meta}$), −159.9 (t, 1F, F$_{para}$), −164.1 (m, 2F, F$_{ortho}$).

EXAMPLE 4

Synthesis of bis(η$^5$-Cyclopentadienyl)zirconium-CH$_2$CHCHCH$_2$bis(pentafluorophenyl)pyrrolylborate 0.120 g (0.436 mmol) of (s-cis/s-trans-η$^4$-butadiene)bis(η$^5$-cyclopentadienyl)zirconium and 0.179 g (0.436 mmol) of bis(pentafluorophenyl)pyrrolylborane are dissolved in 10 ml of toluene at room temperature and stirred for 1 hour. The solvent is then removed under reduced pressure. The remaining precipitate is taken up with 30 ml of pentane and stirred for 3 hours. After filtration of the yellow suspension and washing of the yellow residue with two 10 ml portions of pentane, the product is obtained as a yellow powder. Yield: 0.195 g (0.284 mmol; 65%).

1H-NMR (599.2 MHz, CD$_2$Cl$_2$, 298 K): δ=7.63 (broad, 1H, H(α)), 7.22 (broad, 1H, H(β)), 6.46 (broad, 1H, H(β')), 5.89 (s, 5H, Cp'), 5.57 (broad, 1H, H(α')), 5.54 (ddd, 3J(H,H)=16.0 Hz 3J(H,H)=12.7 Hz 3J(H,H)=8.0 Hz, 1H, H(2)), 5.24 (s, 5H, Cp), 4.34 (dd, 3J(H,H)=16.0 Hz 3J(H, H)=10.5 Hz, 1H, H(3)), 2.71 (d, 2J(H,H)=16.0 Hz, 1H, H(4')), 2.60 (dd, 2J(H,H)=4.9 Hz 3J(H,H)=8.0 Hz, 1H, H(1')), 2.29 (dd, 2J(H,H)=16.0 Hz, 3J(H,H)=10.5 Hz, 1H, H(4)), 1.90 (dd, 2J(H,H)=4.9 Hz 3J(H,H)=12.7 Hz, 1H, H(1)). 13C-NMR (150.7 MHz, CD$_2$Cl$_2$, 298 K): δ=147.4 (broad, C(α')), 133.1 (broad, C(α)),120.8 (C(2)), 114.0 (C(3)), 110.5 (Cp), 108.0 (Cp'), 95.0 (broad, C(β)), 47.8 (C(1)), 28.3 (broad, C(4)). 13C-NMR (150.7 MHz, CD$_2$Cl2, 213 K): δ=147.0 (dm, 1J(F,C)=232 Hz, ArF$_{ortho}$) 144.1 (C(α')), 137.8 (dm, 1J(F,C)=240 Hz, ArF$_{para}$), 136.5 (dm, 1J(F,C)=248 Hz, ArF$_{meta}$), 133.2 (C(α)), 121.0 (C(2)), 112.9 (broad, C$_{ipso}$), 110.0 (C(3)), 109.8 (Cp), 20 109.4 (C(β)), 107.1 (Cp'), 92.1 (C(β)), 47.0 (C(1)), 26.6 (broad, C(4)). 11B-NMR (64.21 MHz, C$_6$D$_6$, 300 K): δ=−7.3 (η½=185 Hz). 19F-NMR (282.41 MHz, C$_7$D$_8$, 300 K): δ=−131.2 (m, 2F, F$_{meta}$), −133.4 (m, 2F, F$_{meta}$), −158.7 (t, 1F, F$_{para}$), −160.0 (t, 1F, F$_{para}$), −163.4 (m, 2F, F$_{ortho}$), −164.0 (m, 2F, F$_{ortho}$).

EXAMPLE 5

Homogeneous Polymerization of Ethene with bis (η$^5$-Cyclopentadienyl)methylzirconiummethylbis (pentafluorophenyl)pyrrolylborate 16 mg (0.06 mmol) of bis(η$^5$-cyclopentadienyl) dimethylzirconium and 26 mg (0.06 mmol) of bis (pentafluorophenyl)pyrrolylborane are dissolved in 10 of toluene at room temperature, 3.5 ml of TIBA are added and stirring is carried out for 10 minutes. This solution is then introduced into a 300 ml polymerization autoclave (Parr 4560) for polymerization. Polymerization is carried out at 25° C. and under an ethene pressure of 10 bar for 60 minutes. The polymer is dried in a vacuum drying oven. 12 g of polyethylene result. The catalyst activity is 0.75 kg of PE per g of metallocene per h.

EXAMPLE 6

Homogeneous Polymerization of Ethene with bis (η$^5$-Cyclopentadienyl)zirconiumCH$_2$CHCHCH$_2$bis (pentafluorophenyl)pyrrolylborate 14 mg (51 μmol) of (s-cis/s-trans-η$^4$-butadiene)bis(η$^5$-cyclopentadienyl)zirconium are reacted with 21 mg (51 μmol) of bis(pentafluorophenyl)pyrrolylborane in 15 ml of toluene, and 5 ml of TIBA are added. Stirring is carried out for 15 minutes. This solution is then introduced into a 1.5 dm$^3$ stirred reactor for polymerization. Polymerization is carried out at room temperature and an ethene pressure of 35 bar for 60 minutes. The polymer is dried in a vacuum drying oven. 16 g of polyethylene result. The catalyst activity is 1.14 kg of PE per g of metallocene per h.

EXAMPLE 7

Homogeneous Polymerization of Propene with bis (η$^5$-Cyclopentadienyl)zirconiumCH$_2$CHCHCH$_2$bis (pentafluorophenyl)pyrrolylborate 42 mg (153 μmol) of (s-cis/s-trans-η$^4$-butadiene)bis(η$^5$-cyclopentadienyl)zirconium are reacted with 63 mg (153 μmol) of bis(pentafluorophenyl)pyrrolylborane in 15 ml of toluene and stirred for 15 minutes. At the same time, a dry 2 1 reactor is flushed first with nitrogen and then with propylene and is filled with 1.5 1 of liquid propylene. 5 ml of TIBA (20% strength in Varsol) are added to this and stirring is carried out for 15 minutes. The prepared catalyst solution is then introduced into the reactor. The reaction mixture is heated to the polymerization temperature of 60° C. and polymerization is carried out for 1 hour. The polymerization is stopped by expelling the remaining propylene gas. The polymer is dried in a vacuum drying oven. 172 g of polypropylene result. The catalyst activity is 4.1 kg of PP per g of metallocene per h.

EXAMPLE 8

Heterogeneous Polymerization of Propene with bis ($\eta^5$-Cyclopentadienyl)zirconium$CH_2CHCHCH_2$bis (pentafluorophenyl)pyrrolylborate 3 g of $SiO_2$ (MS 3030, from PQ, dried at 600° C. in an argon stream) are suspended in 15 ml of toluene, and a solution of 147 mg (0.535 mmol) of (s-cis/s-trans-$\eta^4$-butadiene)bis($\eta^5$-cyclopentadienyl)zirconium and 221 mg (0.535 mmol) of bis(pentafluorophenyl)pyrrolylborane in 5 ml of toluene is slowly added dropwise while stirring. Stirring is continued for 1 hour at room temperature, and the solvent is then removed under reduced pressure from an oil pump until the weight remains constant. For the introduction into the polymerization system, 1 g of the supported catalyst is resuspended in 30 $cm^3$ of Exxsol.

Polymerization

At the same time, a dry 16 $dm^3$ reactor is flushed first with nitrogen and then with propylene and is filled with 10 $dm^3$ of liquid propylene. Thereafter, 0.5 $cm^3$ of a 20% strength triisobutylaluminum solution in Varsol, diluted with 30 $cm^3$ of Exxsol, is introduced into the reactor and the batch is stirred at 30° C. for 15 minutes. The catalyst suspension is then introduced into the reactor. The reaction mixture is heated to the polymerization temperature of 60° C. (4° C./min) and the polymerization system is kept at 60° C. for 1 hour by cooling. The polymerization is stopped by expelling the remaining propylene gas. The polymer is dried in a vacuum drying oven. 182 g of polypropylene powder result. The reactor has no deposits on the inner surface or stirrer. The catalyst activity is 3.7 kg of PP per g of metallocene per h.

We claim:

1. A zwitterionic transition metal compound of the formula I

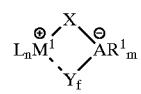

where $M^1$ is titanium, zirconium of hafnium, n is 2 or 3,

L is a substituted cyclopentadienyl ring or a substituted indenyl ring, it also being possible for two or more substituents of the indenyl ring together to form a ring system and for the cyclopentadienyl and indenyl rings to be unbridged or bridged by Z, with Z bridging groups of the formula $M^2R^2R^3$, where $M^2$ is carbon, silicon, germanium or tin and $R^2$ and $R^3$ are identical or different $C_1$–$C_{10}$-alkyl, $C_6$–$C_{14}$-aryl or trimethylsilyl, X is an aromatic or nonaromatic heterocyclic structure, Y is a $C_1$–$C_{40}$-hydrocarbon radical which may be halogenated with halogens, f is 1, A is boron, $R^1$ are identical or different and are each a perfluorinated $C_1$–$C_{40}$-alkyl or aryl group, and m is 2.

2. The compound of formula I of claim 1, wherein $M^1$ is zirconium, n is 3,

L are identical or different and are each a substituted cyclopentadienyl group, where two radicals L are linked to one another via a bridge Z, Z being a substituted carbon or silicon atom, X is an unsaturated heterocyclic structure with N as a heteroatom, which is bonded to M by a coordinate bond, and $R^1$ are identical and are each a pentafluorophenyl group.

3. The compound of formula I of claim 1, wherein

Y is of the formula

and g is an integer from 0 to 37, it also being possible for individual hydrogen atoms to be substituted by alkyl groups.

4. A catalyst containing at least one compound as claimed in claim 1, and a cocatalyst.

5. A process for the preparation of a polyolefin in the presence of a as claimed in claim 1.

6. A process for the preparation of a polyolefin in the presence of a catalyst in claim 4.

7. The compound of claim 4, wherein

X is an unsaturated heterocyclic structure with N as heteroatom, which is bonded to M by a coordinate bond;

g is 1;

$R^1$ are identical and are each a pentafluorophenyl group.

* * * * *

UNITED STATES PATENT AND TRADEMARK OFFICE
CERTIFICATE OF CORRECTION

PATENT NO. : 6,486,277 B1
DATED : November 26, 2002
INVENTOR(S) : Erker et al.

It is certified that error appears in the above-identified patent and that said Letters Patent is hereby corrected as shown below:

Column 78,
Line 49, "claim 4, wherein" should be -- claim 3, wherein --.

Signed and Sealed this

Twenty ninth Day of April, 2003

JAMES E. ROGAN
*Director of the United States Patent and Trademark Office*